(12) United States Patent
Karperien et al.

(10) Patent No.: US 9,340,605 B2
(45) Date of Patent: May 17, 2016

(54) VHH FOR APPLICATION IN TISSUE REPAIR, ORGAN REGENERATION, ORGAN REPLACEMENT AND TISSUE ENGINEERING

(75) Inventors: Hermanus Bernardus Johannes Karperien, Eibergen (NL); Cornelis Theodorus Verrips, Houten (NL); Mohamed El Khattabi, Amersfoort (NL); Emilie Dooms Rodrigues, Utrecht (NL); Jan De Boer, Zeist (NL); Clemens Antoni Van Blitterswijk, Ruigahuizen (NL); Renee De Bruin, Utrecht (NL)

(73) Assignee: UNIVERSITEIT TWENTE, Enschede (NL)

( * ) Notice: Subject to any disclaimer, the term of this patent is extended or adjusted under 35 U.S.C. 154(b) by 789 days.

(21) Appl. No.: 13/503,355

(22) PCT Filed: Oct. 21, 2010

(86) PCT No.: PCT/NL2010/050700
§ 371 (c)(1),
(2), (4) Date: Jul. 16, 2012

(87) PCT Pub. No.: WO2011/049449
PCT Pub. Date: Apr. 28, 2011

(65) Prior Publication Data
US 2012/0276103 A1 Nov. 1, 2012

(30) Foreign Application Priority Data
Oct. 22, 2009 (EP) ..................................... 09173832

(51) Int. Cl.
| | | |
|---|---|---|
| A61K 39/00 | (2006.01) | |
| C07K 16/22 | (2006.01) | |
| C12P 21/08 | (2006.01) | |
| C07K 16/18 | (2006.01) | |
| A61L 27/22 | (2006.01) | |
| A61L 27/54 | (2006.01) | |
| A61L 31/04 | (2006.01) | |
| A61L 31/16 | (2006.01) | |
| C07K 16/44 | (2006.01) | |

(52) U.S. Cl.
CPC .............. *C07K 16/18* (2013.01); *A61L 27/227* (2013.01); *A61L 27/54* (2013.01); *A61L 31/047* (2013.01); *A61L 31/16* (2013.01); *C07K 16/22* (2013.01); *C07K 16/44* (2013.01); *A61L 2300/25* (2013.01); *A61L 2300/432* (2013.01); *C07K 2317/22* (2013.01); *C07K 2317/569* (2013.01)

(58) Field of Classification Search
None
See application file for complete search history.

(56) References Cited

U.S. PATENT DOCUMENTS

| 2006/0115470 A1 | 6/2006 | Silence et al. | |
| 2010/0120681 A1 * | 5/2010 | Merchiers et al. | .............. 514/12 |

FOREIGN PATENT DOCUMENTS

| WO | WO-01/44301 | 6/2001 |
| WO | WO 0144301 A1 * | 6/2001 |
| WO | WO 03072542 A2 * | 9/2003 |
| WO | WO-2005/095461 | 10/2005 |

OTHER PUBLICATIONS

Database WPI, Accession No. 2008-N53963, Sep. 24, 2008.
DeFrance et al., "Human interferon-γ acts as a B cell growth factor in the anti-IgM antibody co-stimulatory assay but has no direct B cell differentiation activity", The Journal of Immunology (1986) 137(12):3861-3867.
De Ranieri et al., "Local application of rhTGF-β2 enhances peri-implant bone volume and bone-implant contact in rat model", Bone (2005) 37:55-62.
Fillit et al., "Induction of antibodies to hyaluronic acid by immunization of rabbits with encapsulated streptococci", J. Exp. Med. (1986) 164:762-776.
International Search Report for PCT/NL2010/050700, mailed Apr. 6, 2011, 8 pages.
Saerens et al., "Identification of a Universal VHH Framework to Graft Non-canonical Antigen-binding Loops of Camel Single-domain Antibodies", J. Mol. Biol. (2005) 352:597-607.
Schmidmaier et al., "Collective Review: Bioactive Implants Coated with Poly(D,L-lactide) and Growth Factors IGF-I, TGF-β1, or BMP-2 for Stimulation of Fracture Healing", Journal of Long-term Effects of Medical Implants (2006) 16(1):61-69.
Various authors, "N. Bionanomaterials", Journal of Biological Inorganic Chemistry (2009) 14(1):S95-S100.

\* cited by examiner

*Primary Examiner* — Vanessa L Ford
*Assistant Examiner* — Sandra Dillahunt
(74) *Attorney, Agent, or Firm* — Morrison & Foerster LLP

(57) ABSTRACT

The present invention relates to a VHH which binds to a growth factor or is an antagonist for a growth factor, or binds to an implant.

4 Claims, 16 Drawing Sheets

SEQUENCE LISTING

```
<160> NUMBER OF SEQ ID NOS: 61

<210> SEQ ID NO 1
<211> LENGTH: 12
<212> TYPE: PRT
<213> ORGANISM: Artificial Sequence
<220> FEATURE:
<223> OTHER INFORMATION: synthetic construct

<400> SEQUENCE: 1

Val Thr Lys His Leu Asn Gln Ile Ser Gln Ser Tyr
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: synthetic construct

<400> SEQUENCE: 2

Ala Pro Trp His Leu Ser Ser Gln Tyr Ser Arg Thr
 1               5                  10

<210> SEQ ID NO 3
<211> LENGTH: 118
<212> TYPE: PRT
<213> ORGANISM: Artificial Sequence
<220> FEATURE:
<223> OTHER INFORMATION: synthetic construct

<400> SEQUENCE: 3

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Arg Asp
                20                  25                  30

Val Met Gly Trp Phe Arg Gln Ala Pro Gly Lys Val Arg Glu Val Val
            35                  40                  45

Gly Ser Ile Thr Trp Ser Gly Ser Thr Tyr Tyr Ala Asp Ser Val
        50                  55                  60

Lys Gly Arg Phe Thr Ile Ser Arg Asp Asn Ala Lys Asn Thr Met Tyr
 65                  70                  75                  80

Leu Gln Met Asn Ser Leu Lys Pro Glu Asp Thr Gly Val Tyr Tyr Cys
                85                  90                  95

Ala Val Ala Glu Leu Gly Ser Thr Tyr Asn Asp Trp Gly Gln Gly Thr
            100                 105                 110

Gln Val Thr Val Ser Ser
        115

<210> SEQ ID NO 4
<211> LENGTH: 126
<212> TYPE: PRT
<213> ORGANISM: Artificial Sequence
<220> FEATURE:
```

<223> OTHER INFORMATION: synthetic construct

<400> SEQUENCE: 4

```
Glu Val Gln Leu Val Glu Ser Gly Gly Gly Leu Val Gln Ala Gly Gly
1               5                   10                  15

Ser Leu Arg Leu Ser Cys Ala Gly Ser Gly Phe Ala Phe Asp Asp Tyr
            20                  25                  30

Ala Ile Gly Trp Phe Arg Gln Gly Pro Gly Lys Glu Arg Glu Gly Val
        35                  40                  45

Ala Cys Ile Ser Gly Lys Asp Gly Ser Thr Tyr Tyr Thr Asp Ser Val
    50                  55                  60

Lys Ala Arg Phe Thr Ile Ser Ser Glu Asn Ala Lys Asn Thr Ala Tyr
65                  70                  75                  80

Leu Gln Met Asn Asn Leu Lys Pro Glu Asp Thr Gly Arg Tyr Phe Cys
                85                  90                  95

Val Ala Asp Pro Asp Gly Gly Cys Asp Ser Phe Thr Gly Ala Thr Met
            100                 105                 110

Met Gly Tyr Trp Ala Arg Gly Thr Gln Val Thr Val Ser Ser
        115                 120                 125
```

<210> SEQ ID NO 5
<211> LENGTH: 118
<212> TYPE: PRT
<213> ORGANISM: Artificial Sequence
<220> FEATURE:
<223> OTHER INFORMATION: synthetic construct

<400> SEQUENCE: 5

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Val Met Gly Trp Phe Arg Gln Ala Pro Gly Lys Val Arg Glu Val Val
        35                  40                  45

Gly Ser Ile Lys Trp Ser Asp Ala Asn Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Gly Val Tyr Tyr Cys
                85                  90                  95

Ala Ala Ala Ile Ile Gly Gly Thr Tyr Asn Asp Trp Gly Gln Gly Thr
            100                 105                 110

Gln Val Thr Val Ser Ser
        115
```

<210> SEQ ID NO 6
<211> LENGTH: 128
<212> TYPE: PRT
<213> ORGANISM: Artificial Sequence
<220> FEATURE:
<223> OTHER INFORMATION: synthetic construct

<400> SEQUENCE: 6

```
Glu Val Gln Leu Val Glu Ser Gly Gly Gly Leu Val His Ala Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
```

```
            35                  40                  45
Ser His Ile Asn Ser Gly Gly Ser Thr Ser Tyr Ala Asp Ser Val
    50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Lys Leu Arg Glu Gly Ala Asp Tyr Ser Gly Ser Tyr Tyr Tyr Leu
                100                 105                 110
Tyr Glu Tyr Asp Tyr Trp Gly Gln Gly Thr Gln Val Thr Val Ser Ser
                115                 120                 125

<210> SEQ ID NO 7
<211> LENGTH: 128
<212> TYPE: PRT
<213> ORGANISM: Artificial Sequence
<220> FEATURE:
<223> OTHER INFORMATION: synthetic construct

<400> SEQUENCE: 7

Glu Val Gln Leu Val Glu Ser Gly Gly Gly Leu Val His Ala Gly Gly
  1               5                  10                  15
Ser Leu Arg Leu Ser Cys Ala Ala Ser Gly Phe Thr Phe Ser Ser Tyr
                 20                  25                  30
Ala Met Ser Trp Val Arg Gln Ala Pro Gly Lys Gly Pro Glu Trp Val
                 35                  40                  45
Ser His Ile Asn Ser Gly Gly Ser Thr Ser Tyr Ala Asp Ser Val
    50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
Ala Lys Leu Arg Glu Gly Ala Asp Tyr Ser Gly Ser Tyr Tyr Tyr Leu
                100                 105                 110
Tyr Glu Tyr Asp Tyr Trp Gly Gln Gly Thr Gln Val Thr Val Ser Ser
                115                 120                 125

<210> SEQ ID NO 8
<211> LENGTH: 128
<212> TYPE: PRT
<213> ORGANISM: Artificial Sequence
<220> FEATURE:
<223> OTHER INFORMATION: synthetic construct

<400> SEQUENCE: 8

Glu Val Gln Leu Val Glu Ser Gly Gly Gly Leu Val His Ala Gly Gly
  1               5                  10                  15
Ser Leu Arg Leu Ser Cys Ala Ala Ser Gly Phe Thr Phe Ser Ser Tyr
                 20                  25                  30
Ala Met Ser Trp Val Arg Gln Ala Pro Gly Lys Gly Pro Glu Trp Val
                 35                  40                  45
Ser His Ile Asn Ser Gly Gly Ser Thr Ser Tyr Ala Asp Ser Val
    50                  55                  60
Lys Gly Arg Phe Thr Ile Ser Arg Asp Asn Ala Lys Asn Thr Leu Tyr
 65                  70                  75                  80
Leu Gln Met Asn Ser Leu Lys Pro Glu Asp Thr Ala Val Tyr Tyr Cys
                 85                  90                  95
```

```
Ala Lys Leu Arg Glu Gly Ala Asp Tyr Ser Gly Ser Tyr Tyr Tyr Leu
            100                 105                 110

Tyr Glu Tyr Asp Tyr Trp Gly Gln Gly Thr Gln Val Thr Val Ser Ser
            115                 120                 125

<210> SEQ ID NO 9
<211> LENGTH: 128
<212> TYPE: PRT
<213> ORGANISM: Artificial Sequence
<220> FEATURE:
<223> OTHER INFORMATION: synthetic construct

<400> SEQUENCE: 9

Glu Val Gln Leu Val Glu Ser Gly Gly Gly Leu Val His Ala Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
            35                  40                  45

Ser His Ile Asn Ser Gly Gly Gly Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Ala Lys Leu Arg Glu Gly Ala Asp Tyr Ser Gly Ser Tyr Tyr Tyr Leu
            100                 105                 110

Tyr Glu Tyr Asp Tyr Trp Gly Gln Gly Thr Gln Val Thr Val Ser Ser
            115                 120                 125

<210> SEQ ID NO 10
<211> LENGTH: 128
<212> TYPE: PRT
<213> ORGANISM: Artificial Sequence
<220> FEATURE:
<223> OTHER INFORMATION: synthetic construct

<400> SEQUENCE: 10

Glu Val Gln Leu Val Glu Ser Gly Gly Gly Leu Val His Ala Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
            35                  40                  45

Ser His Ile Asn Ser Gly Gly Gly Ser Thr Ser Tyr Ala Asp Ser Val
        50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                85                  90                  95

Ala Lys Leu Arg Glu Gly Ala Asp Tyr Ser Gly Ser Tyr Tyr Tyr Leu
            100                 105                 110

Tyr Glu Tyr Asp Tyr Trp Gly Gln Gly Thr Gln Val Thr Val Ser Ser
            115                 120                 125

<210> SEQ ID NO 11
<211> LENGTH: 126
<212> TYPE: PRT
<213> ORGANISM: Artificial Sequence
```

```
<220> FEATURE:
<223> OTHER INFORMATION: synthetic construct

<400> SEQUENCE: 11

Glu Val Gln Leu Val Glu Ser Gly Gly Gly Leu Val Gln Ala Gly Gly
  1               5                  10                  15

Ser Leu Arg Leu Ser Cys Ala Ala Ser Gly Ser Ile Phe Ser Ile Leu
             20                  25                  30

Thr Met Gly Trp Tyr Arg Gln Ala Pro Gly Arg Gln Arg Glu Met Val
         35                  40                  45

Ala Thr Ile Thr Thr Ser Gly Gly Leu Thr Asn Tyr Thr Asp Ser Val
     50                  55                  60

Lys Gly Arg Phe Ser Ile Ser Arg Asp Asn Asn Lys Asn Thr Val Tyr
 65                  70                  75                  80

Leu Gln Met Asn Ser Leu Lys Pro Glu Asp Thr Ala Val Tyr Tyr Cys
                 85                  90                  95

Asn Ala Ala Met Val Gly Gly Val Gly Leu Gly Arg Arg Pro Ser
            100                 105                 110

Phe Ser Tyr Trp Gly Gln Gly Thr Gln Val Thr Val Ser Ser
        115                 120                 125

<210> SEQ ID NO 12
<211> LENGTH: 119
<212> TYPE: PRT
<213> ORGANISM: Artificial Sequence
<220> FEATURE:
<223> OTHER INFORMATION: synthetic construct

<400> SEQUENCE: 12

Glu Val Gln Leu Val Glu Ser Gly Gly Gly Leu Val Gln Ser Gly Gly
  1               5                  10                  15

Ser Leu Arg Leu Ser Cys Ala Ala Ser Gly Arg Thr Phe Ser Thr Asp
             20                  25                  30

Phe Met Gly Trp Phe Arg Gln Ala Pro Gly Lys Glu Arg Glu Phe Val
         35                  40                  45

Ala Thr Ile Asp Trp Arg Ser Gly Ser Ala Tyr Ala Asp Ser Val
     50                  55                  60

Gln Gly Arg Phe Thr Ile Ser Lys Asp Asn Ala Lys Asn Thr Val Tyr
 65                  70                  75                  80

Leu Gln Met Met Asn Leu Gln Pro Gly Asp Thr Gly Val Tyr Tyr Cys
                 85                  90                  95

Ala Ala Gln Met Ile Gly Ala Ser Ser Tyr Gly Tyr Trp Gly Arg Gly
            100                 105                 110

Thr Gln Val Thr Val Ser Ser
        115

<210> SEQ ID NO 13
<211> LENGTH: 126
<212> TYPE: PRT
<213> ORGANISM: Artificial Sequence
<220> FEATURE:
<223> OTHER INFORMATION: synthetic construct

<400> SEQUENCE: 13

Glu Val Gln Leu Val Glu Ser Gly Gly Gly Leu Val Gln Ala Gly Gly
  1               5                  10                  15

Ser Leu Arg Leu Ser Cys Ala Gly Ser Gly Phe Ala Phe Asp Asp Tyr
             20                  25                  30
```

-continued

```
Ala Ile Gly Trp Phe Arg Gln Gly Pro Gly Lys Glu Arg Glu Gly Val
         35                  40                  45

Ala Cys Ile Ser Gly Lys Asp Gly Ser Thr Tyr Tyr Thr Asp Ser Val
 50                  55                  60

Lys Ala Arg Phe Thr Ile Ser Ser Glu Asn Ala Lys Asn Thr Ala Tyr
 65                  70                  75                  80

Leu Gln Met Asn Asn Leu Lys Pro Glu Asp Thr Gly Arg Tyr Phe Cys
                 85                  90                  95

Val Ala Asp Pro Asp Gly Gly Cys Asp Ser Phe Thr Gly Ala Thr Met
                100                 105                 110

Met Gly Tyr Trp Ala Gln Gly Thr Gln Val Thr Val Ser Ser
            115                 120                 125

<210> SEQ ID NO 14
<211> LENGTH: 118
<212> TYPE: PRT
<213> ORGANISM: Artificial Sequence
<220> FEATURE:
<223> OTHER INFORMATION: synthetic construct

<400> SEQUENCE: 14

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Arg Asp
                20                  25                  30

Val Met Gly Trp Phe Arg Gln Ala Pro Gly Lys Val Arg Glu Glu Val
             35                  40                  45

Gly Ser Ile Lys Trp Ser Asp Ala Asn Thr Tyr Tyr Ala Asp Ser Val
 50                  55                  60

Lys Gly Arg Phe Thr Ile Ser Arg Asp Asn Ala Lys Asn Thr Met Tyr
 65                  70                  75                  80

Leu Gln Met Asn Ser Leu Lys Pro Glu Asp Thr Gly Val Tyr Tyr Cys
                 85                  90                  95

Ala Ala Ala Ile Ile Gly Gly Thr Tyr Asn Asp Trp Gly Gln Gly Thr
                100                 105                 110

Gln Val Thr Val Ser Ser
            115

<210> SEQ ID NO 15
<211> LENGTH: 119
<212> TYPE: PRT
<213> ORGANISM: Artificial Sequence
<220> FEATURE:
<223> OTHER INFORMATION: synthetic construct

<400> SEQUENCE: 15

Glu Val Gln Leu Val Glu Ser Gly Gly Gly Leu Val Gln Ser Gly Gly
 1               5                  10                  15

Ser Leu Arg Leu Ser Cys Ala Ala Ser Gly Arg Thr Phe Ser Thr Asp
                20                  25                  30

Phe Met Gly Trp Phe Arg Gln Ala Pro Gly Lys Glu Arg Glu Phe Val
             35                  40                  45

Ala Thr Ile Asp Trp Arg Ser Gly Ser Ala Gly Tyr Ala Asp Ser Val
 50                  55                  60

Gln Gly Arg Phe Thr Ile Ser Lys Asp Asn Ala Lys Asn Thr Val Tyr
 65                  70                  75                  80

Leu Gln Met Asn Ser Leu Lys Pro Glu Asp Thr Gly Val Tyr Tyr Cys
                 85                  90                  95
```

```
Ala Ala Gln Met Ile Gly Ala Ser Ser Tyr Gly Tyr Trp Gly Arg Gly
            100                 105                 110

Thr Gln Val Thr Val Ser Ser
        115

<210> SEQ ID NO 16
<211> LENGTH: 128
<212> TYPE: PRT
<213> ORGANISM: Artificial Sequence
<220> FEATURE:
<223> OTHER INFORMATION: synthetic construct

<400> SEQUENCE: 16

Glu Val Gln Leu Val Glu Ser Gly Gly Gly Leu Val His Ala Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Pro Glu Trp Val
         35                  40                  45

Ser His Ile Asn Ser Gly Gly Gly Ser Thr Ser Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Leu Arg Glu Gly Ala Asp Tyr Ser Gly Ser Tyr Tyr Tyr Leu
            100                 105                 110

Tyr Glu Tyr Asp Tyr Trp Gly Gln Gly Thr Gln Val Thr Val Ser Ser
        115                 120                 125

<210> SEQ ID NO 17
<211> LENGTH: 115
<212> TYPE: PRT
<213> ORGANISM: Artificial Sequence
<220> FEATURE:
<223> OTHER INFORMATION: synthetic construct

<400> SEQUENCE: 17

Glu Val Gln Leu Val Glu Ser Gly Gly Gly Leu Val Gln Ala Gly Gly
  1               5                  10                  15

Ser Leu Thr Leu Ser Cys Ala Ala Ser Glu Ile Ile Ser Ser Ile Asn
             20                  25                  30

Ala Met Gly Trp Tyr Arg Gln Ala Pro Gly Lys Gln Arg Glu Leu Val
         35                  40                  45

Ala Leu Ile Gly Ser Gly Gly Thr Thr Lys Tyr Gly Asp Cys Ala Lys
     50                  55                  60

Gly Arg Phe Thr Ile Ser Arg Asp Asn Ala Lys Asn Thr Val Thr Leu
 65                  70                  75                  80

Gln Met Asn Ser Leu Lys Pro Glu Asp Thr Ala Val Tyr Tyr Cys Tyr
                 85                  90                  95

Val His Asp Tyr Asp His Lys Ala Trp Gly Gln Gly Thr Gln Val Thr
            100                 105                 110

Val Ser Ser
        115

<210> SEQ ID NO 18
<211> LENGTH: 115
<212> TYPE: PRT
```

<213> ORGANISM: Artificial Sequence
<220> FEATURE:
<223> OTHER INFORMATION: synthetic construct

<400> SEQUENCE: 18

```
Glu Val Gln Leu Val Glu Ser Gly Gly Gly Leu Val Gln Ala Gly Gly
 1               5                  10                  15

Ser Leu Thr Leu Ser Cys Ala Ala Ser Glu Ile Ile Ser Ser Ile Asn
            20                  25                  30

Ala Met Gly Trp Tyr Arg Gln Ala Pro Gly Lys Gln Arg Glu Leu Val
        35                  40                  45

Ala Leu Ile Gly Ser Gly Gly Thr Thr Lys Tyr Gly Asp Cys Ala Lys
    50                  55                  60

Gly Arg Phe Thr Ile Ser Arg Asp Asn Ala Lys Asn Thr Val Thr Leu
65                  70                  75                  80

Gln Met Asn Ser Leu Lys Pro Glu Asp Thr Ala Val Tyr Tyr Cys Tyr
                85                  90                  95

Val His Asp Tyr Asp His Lys Ala Trp Gly Gln Gly Thr Gln Val Thr
            100                 105                 110

Val Ser Ser
        115
```

<210> SEQ ID NO 19
<211> LENGTH: 130
<212> TYPE: PRT
<213> ORGANISM: Artificial Sequence
<220> FEATURE:
<223> OTHER INFORMATION: synthetic construct

<400> SEQUENCE: 19

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
            20                  25                  30

Gly Met Gly Trp Phe Arg Gln Ala Pro Gly Lys Glu Arg Asp Phe Val
        35                  40                  45

Ala Ala Val Ser Arg Ser Gly Gly Asn Thr Tyr Tyr Thr Ala Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Ala Ala Gly Arg Trp Glu Ser Gly Ser Arg Leu Gly Ser Thr Trp Tyr
            100                 105                 110

Gly Glu Arg Thr Tyr Asp Tyr Trp Gly Gln Gly Thr Gln Val Thr Val
        115                 120                 125

Ser Ser
    130
```

<210> SEQ ID NO 20
<211> LENGTH: 131
<212> TYPE: PRT
<213> ORGANISM: Artificial Sequence
<220> FEATURE:
<223> OTHER INFORMATION: synthetic construct

<400> SEQUENCE: 20

```
Glu Val Gln Leu Val Glu Ser Gly Gly Gly Leu Val Gln Val Gly Gly
 1               5                  10                  15
```

```
Ser Leu Arg Leu Ser Cys Ala Ala Ser Gly Arg Thr Ser Ser Met Tyr
            20                  25                  30

Ser Met Gly Trp Phe Arg Gln Ala Pro Gly Lys Glu Arg Glu Phe Val
                35                  40                  45

Ala Ala Ile Gly Trp Arg Phe Gly Glu Lys Tyr Tyr Thr Asn Ser Val
     50                  55                  60

Lys Gly Arg Phe Thr Ile Ser Arg Asp Gly Ala Glu Asn Thr Asn Thr
 65                  70                  75                  80

Val Tyr Leu Gln Met Asn Ser Leu Lys Pro Asp Asp Thr Ala Val Tyr
                 85                  90                  95

Tyr Cys Ala Ala Asp Pro Asp Asp Ala Ser Gln Tyr Tyr Ser Asp Trp
            100                 105                 110

Met Lys Gly Tyr Gly Met Asp Tyr Trp Gly Lys Gly Thr Leu Val Thr
                115                 120                 125

Val Ser Ser
        130

<210> SEQ ID NO 21
<211> LENGTH: 130
<212> TYPE: PRT
<213> ORGANISM: Artificial Sequence
<220> FEATURE:
<223> OTHER INFORMATION: synthetic construct

<400> SEQUENCE: 21

Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Phe Ser Ser Tyr
            20                  25                  30

Gly Met Gly Trp Phe Arg Gln Ala Pro Gly Lys Glu Arg Asp Phe Val
                35                  40                  45

Ala Ala Val Ser Lys Ser Gly Gly Ser Thr Tyr Tyr Thr Ala Ser Val
     50                  55                  60

Lys Gly Arg Phe Thr Val Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Gly Arg Trp Glu Ser Gly Ser Arg Pro Gly Ser Thr Trp Tyr
            100                 105                 110

Gly Glu Arg Thr Tyr Asp Tyr Trp Gly Gln Gly Thr Gln Val Thr Val
                115                 120                 125

Ser Ser
    130

<210> SEQ ID NO 22
<211> LENGTH: 116
<212> TYPE: PRT
<213> ORGANISM: Artificial Sequence
<220> FEATURE:
<223> OTHER INFORMATION: synthetic construct

<400> SEQUENCE: 22

Glu Val Gln Leu Val Glu Ser Gly Gly Gly Leu Val Gln Ala Gly Gly
  1               5                  10                  15

Ser Leu Arg Leu Ser Cys Ala Ala Ser Arg Arg Ile Ser Gly Ile Tyr
            20                  25                  30

Ala Met Gly Trp Tyr Arg Gln Ser Pro Gly Lys Glu Arg Glu Leu Val
```

```
            35                  40                  45

Ala Ala Ile Thr Thr Ser Asp His Thr Asn Tyr Ala Asp Phe Val Lys
    50                  55                  60

Gly Arg Phe Thr Ile Ser Arg Asp Lys Val Asn Asn Thr Val Tyr Leu
65                  70                  75                  80

Glu Met Asn Thr Leu Lys Pro Glu Asp Thr Ala Val Tyr Tyr Cys Lys
                85                  90                  95

Gln Ser Ala Trp Gly Arg Asn Asp Tyr Trp Gly Gln Gly Thr Arg Val
            100                 105                 110

Thr Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: synthetic construct

<400> SEQUENCE: 23

Glu Val Gln Leu Val Glu Ser Gly Gly Gly Leu Val Gln Ala Gly Gly
1               5                   10                  15

Ser Leu Lys Leu Ser Cys Ala Ala Ser Arg Arg Ile Ser Gly Ile Tyr
            20                  25                  30

Ala Met Gly Trp Tyr Arg Gln Thr Pro Gly Lys Glu Arg Glu Leu Val
            35                  40                  45

Ala Ala Ile Thr Thr Ser Asp His Thr Asn Tyr Ala Asp Phe Val Lys
    50                  55                  60

Gly Arg Phe Thr Ile Ser Arg Asp Lys Val Asn Asn Thr Val Tyr Leu
65                  70                  75                  80

Glu Met Asn Thr Leu Lys Pro Glu Asp Thr Ala Val Tyr Tyr Cys Lys
                85                  90                  95

Gln Ser Ala Trp Gly Arg Asn Asp Tyr Trp Gly Gln Gly Thr Arg Val
            100                 105                 110

Thr Val Ser Ser
        115

<210> SEQ ID NO 24
<211> LENGTH: 124
<212> TYPE: PRT
<213> ORGANISM: Artificial Sequence
<220> FEATURE:
<223> OTHER INFORMATION: synthetic construct

<400> SEQUENCE: 24

Glu Val Gln Leu Val Glu Ser Gly Gly Gly Phe Val Gln Ala Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
            35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ser
                85                  90                  95
```

```
Ala Val Thr Ile Leu Leu Thr Ser Gly Gly Trp Gly Ser Gly Asn Asp
            100                 105                 110

Tyr Trp Gly Gln Gly Thr Gln Val Thr Val Ser Ser
        115                 120

<210> SEQ ID NO 25
<211> LENGTH: 123
<212> TYPE: PRT
<213> ORGANISM: Artificial Sequence
<220> FEATURE:
<223> OTHER INFORMATION: synthetic construct

<400> SEQUENCE: 25

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Asp Phe Val
        35                  40                  45

Ala Ala Ile Ser Trp Ser Gly Ser Thr Tyr Tyr Thr Gly Ser Val
    50                  55                  60

Lys Gly Arg Phe Asn Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gly Pro Arg Ser Ala Tyr Tyr Asp Asp Tyr Gly Tyr Asp Tyr
            100                 105                 110

Trp Gly Gln Gly Thr Gln Val Thr Val Ser Ser
        115                 120

<210> SEQ ID NO 26
<211> LENGTH: 121
<212> TYPE: PRT
<213> ORGANISM: Artificial Sequence
<220> FEATURE:
<223> OTHER INFORMATION: synthetic construct

<400> SEQUENCE: 26

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Val
            20                  25                  30

Ser Met Gly Trp Tyr Arg Gln Val Pro Gly Lys Gln Arg Glu Leu Val
        35                  40                  45

Ala Ala Ile Thr Ser Ala Gly Ser Thr Asn Tyr Gly Asp Ser Ala Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ser Tyr Gly Leu Gly Tyr Pro Gly Asp Tyr Gly Ile Asp Tyr Trp Gly
            100                 105                 110

Lys Gly Thr Leu Val Thr Val Ser Ser
        115                 120

<210> SEQ ID NO 27
<211> LENGTH: 121
<212> TYPE: PRT
<213> ORGANISM: Artificial Sequence
```

<220> FEATURE:
<223> OTHER INFORMATION: synthetic construct

<400> SEQUENCE: 27

Glu Val Gln Leu Val Glu Ser Gly Gly Gly Leu Val Arg Ala Gly Gly
1               5                   10                  15

Ser Leu Arg Leu Ser Cys Ala Ala Ser Gly Arg Thr Phe Ser Gly Tyr
            20                  25                  30

Val Ala Gly Trp Phe Arg Gln Ala Pro Gly Lys Glu Arg Glu Phe Val
        35                  40                  45

Ala Ala Ile Ser Trp Ser Gly Ile Thr Tyr Tyr Gly Asp Ser Val Lys
    50                  55                  60

Gly Arg Phe Thr Ile Ala Arg Asp Asn Ser Lys Asn Gly Val Tyr Leu
65                  70                  75                  80

Gln Met Asn Ser Leu Lys Pro Glu Asp Thr Ala Val Tyr Tyr Cys Gly
                85                  90                  95

Ala Gly Lys Gly Tyr Tyr Lys Asp Tyr Arg Gly Tyr Asp Tyr Trp Gly
            100                 105                 110

Gln Gly Thr Gln Val Thr Val Ser Ser
        115                 120

<210> SEQ ID NO 28
<211> LENGTH: 116
<212> TYPE: PRT
<213> ORGANISM: Artificial Sequence
<220> FEATURE:
<223> OTHER INFORMATION: synthetic construct

<400> SEQUENCE: 28

Glu Val Gln Leu Val Glu Ser Gly Gly Gly Ser Val Gln Ala Gly Gly
1               5                   10                  15

Ser Leu Arg Leu Ser Cys Ala Ala Ser Arg Arg Ile Ser Gly Ile Tyr
            20                  25                  30

Ala Met Gly Trp Tyr Arg Gln Ser Pro Gly Lys Glu Arg Glu Leu Val
        35                  40                  45

Ala Ala Ile Thr Thr Ser Asp His Thr Asn Tyr Ala Asp Phe Val Lys
    50                  55                  60

Gly Arg Phe Thr Ile Ser Arg Asp Lys Val Asn Asn Thr Val Tyr Leu
65                  70                  75                  80

Glu Met Asn Thr Leu Lys Pro Glu Asp Thr Ala Val Tyr Tyr Cys Lys
                85                  90                  95

Gln Ser Ala Trp Gly Arg Asn Asp Tyr Trp Gly Gln Gly Thr Arg Val
            100                 105                 110

Thr Val Ser Ser
        115

<210> SEQ ID NO 29
<211> LENGTH: 121
<212> TYPE: PRT
<213> ORGANISM: Artificial Sequence
<220> FEATURE:
<223> OTHER INFORMATION: synthetic construct

<400> SEQUENCE: 29

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

```
Val Ala Gly Trp Phe Arg Gln Ala Pro Gly Lys Glu Arg Glu Phe Val
        35                  40                  45

Ala Ala Ser Ser Trp Ser Gly Ile Thr Tyr Tyr Gly Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Gly
                 85                  90                  95

Ala Gly Lys Gly Tyr Tyr Lys Asp Tyr Arg Gly Tyr Asp Tyr Trp Gly
            100                 105                 110

Gln Gly Thr Gln Val Thr Val Ser Ser
            115                 120

<210> SEQ ID NO 30
<211> LENGTH: 124
<212> TYPE: PRT
<213> ORGANISM: Artificial Sequence
<220> FEATURE:
<223> OTHER INFORMATION: synthetic construct

<400> SEQUENCE: 30

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ser Ala Phe Ser Ile Asn
            20                  25                  30

Ala Met Gly Trp Tyr Arg Gln Gly Pro Gly Lys Gln Arg Thr Leu Val
        35                  40                  45

Ala Arg Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Tyr
                 85                  90                  95

Ala Val His Ser Lys Leu Ser Thr Thr Gly Trp Gly Thr Ile Gly Asp
            100                 105                 110

Tyr Trp Gly Gln Gly Thr Gln Val Thr Val Ser Ser
            115                 120

<210> SEQ ID NO 31
<211> LENGTH: 130
<212> TYPE: PRT
<213> ORGANISM: Artificial Sequence
<220> FEATURE:
<223> OTHER INFORMATION: synthetic construct

<400> SEQUENCE: 31

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Asp Asp Tyr
            20                  25                  30

Ile Ile Gly Trp Phe Arg Gln Ala Pro Gly Lys Glu Arg Glu Gly Ile
        35                  40                  45

Ser Cys Ile Ser Ser Ser Asp Gly Ser Thr Tyr Tyr Ala Asp Ser Val
 50                  55                  60

Thr Gly Arg Phe Thr Ile Ser Ser Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

Ala Ala His Ala Lys Trp Pro Tyr Gly Thr Tyr Ser Phe Arg Arg Cys
                100                 105                 110

Arg Arg Ala Ser Phe Asp Ser Trp Gly Gln Gly Thr Gln Val Thr Val
            115                 120                 125

Ser Ser
    130

<210> SEQ ID NO 32
<211> LENGTH: 121
<212> TYPE: PRT
<213> ORGANISM: Artificial Sequence
<220> FEATURE:
<223> OTHER INFORMATION: synthetic construct

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Val Ala Gly Trp Phe Arg Gln Ala Pro Gly Lys Glu Arg Glu Phe Val
        35                  40                  45

Val Ala Leu Ser Trp Ser Gly Ile Thr Tyr Tyr Gly Asp Ser Val Lys
    50                  55                  60

Gly Arg Phe Thr Ile Ser Arg Asp Asn Gly Lys Asn Thr Val Tyr Leu
65                  70                  75                  80

Gln Met Asn Ser Leu Lys Pro Glu Asp Thr Ala Val Tyr Tyr Cys Gly
                85                  90                  95

Ala Gly Lys Gly Tyr Tyr Lys Asp Tyr Arg Gly Tyr Asp Tyr Trp Gly
            100                 105                 110

Gln Gly Thr Gln Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: synthetic construct

<400> SEQUENCE: 33

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Gly Tyr
            20                  25                  30

Val Ala Gly Trp Phe Arg Gln Ala Pro Gly Lys Glu Arg Glu Phe Val
        35                  40                  45

Ala Ala Ile Ser Trp Ser Gly Ile Thr Tyr Ala Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Lys Pro Glu Asp Thr Ala Val Tyr Tyr Cys Gly
                85                  90                  95

Ala Gly Lys Gly Tyr Tyr Lys Asp Tyr Arg Gly Tyr Glu Tyr Trp Gly
            100                 105                 110

Gln Gly Thr Gln Val Thr Val Ser Ser
        115                 120

```
<210> SEQ ID NO 34
<211> LENGTH: 124
<212> TYPE: PRT
<213> ORGANISM: Artificial Sequence
<220> FEATURE:
<223> OTHER INFORMATION: synthetic construct

<400> SEQUENCE: 34

Glu Val Gln Leu Val Glu Ser Gly Gly Gly Leu Val Gln Ala Gly Gly
 1               5                  10                  15

Ser Leu Arg Leu Ala Cys Ala Ala Ser Gly Arg Thr Phe Ser Asn Tyr
            20                  25                  30

Arg Met Gly Trp Phe Arg Gln Ala Pro Gly Gln Glu Arg Glu Phe Val
        35                  40                  45

Ala Ala Ile Ser Gly Ser Gly Ser Phe Thr Tyr Tyr Ala Asp Ser Val
    50                  55                  60

Lys Gly Arg Ser Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Gly Ala Gly Val His Leu Gly Ala Ala Thr Ser Tyr Thr Arg Tyr Asp
            100                 105                 110

Phe Trp Gly Gln Gly Thr Gln Val Thr Val Ser Ser
        115                 120

<210> SEQ ID NO 35
<211> LENGTH: 132
<212> TYPE: PRT
<213> ORGANISM: Artificial Sequence
<220> FEATURE:
<223> OTHER INFORMATION: synthetic construct

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Val Val Ser Gly Phe Thr Ile Ser Asn Tyr
            20                  25                  30

Gly Met Ser Trp Val Arg Gln Ala Pro Gly Lys Gly Pro Glu Trp Glu
        35                  40                  45

Trp Val Ser Ala Ile Asn Ser Gly Gly Asp Ser Thr Arg Tyr Ala Asp
    50                  55                  60

Ser Val Lys Gly Arg Phe Thr Ile Ser Arg Asp Asn Ala Lys Asn Thr
65                  70                  75                  80

Leu Tyr Leu Gln Met Asn Ser Leu Lys Pro Glu Asp Ala Ala Val Tyr
                85                  90                  95

Phe Cys Thr Arg Glu Lys Thr Ala Tyr Tyr Cys Ser Gly Ser Gly Cys
            100                 105                 110

Tyr Asp Pro Arg Tyr Glu Phe Asp Tyr Trp Gly Arg Gly Thr Gln Val
        115                 120                 125

Thr Val Ser Ser
    130

<210> SEQ ID NO 36
<211> LENGTH: 126
<212> TYPE: PRT
<213> ORGANISM: Artificial Sequence
<220> FEATURE:
<223> OTHER INFORMATION: synthetic construct

<400> SEQUENCE: 36
```

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Ser Ile Ser Leu Tyr
            20                  25                  30

Ala Met Ala Trp Phe Arg Gln Ala Ala Gly Lys Glu Arg Glu Phe Val
        35                  40                  45

Ala Ala Ile Asn Trp Ser Gly Gly Ser Thr Arg Tyr Ala Asp Ser Val
    50                  55                  60

Lys Gly Arg Phe Ser Ile Ser Arg Asp Thr Ala Lys Asn Thr Val Tyr
65                  70                  75                  80

Leu Thr Met Asn Ser Leu Lys Pro Glu Asp Thr Ala Val Tyr Tyr Cys
                85                  90                  95

Ala Thr Asp Ser Ser Thr Thr Val Val Phe Tyr Ser Ser Asn Ser
                100                 105                 110

Leu Arg Tyr Trp Gly Gln Gly Thr Gln Val Thr Val Ser Ser
            115                 120                 125
```

<210> SEQ ID NO 37
<211> LENGTH: 119
<212> TYPE: PRT
<213> ORGANISM: Artificial Sequence
<220> FEATURE:
<223> OTHER INFORMATION: synthetic construct

<400> SEQUENCE: 37

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Gly Ala Met Ala
            20                  25                  30

Trp Phe Arg Gln Ala Pro Gly Lys Glu Arg Asp Leu Val Ala Ser Ile
        35                  40                  45

Ser Arg Ser Gly Val Ser Thr Tyr Tyr Ala Asp Ser Val Lys Val Arg
    50                  55                  60

Phe Thr Ile Ser Arg Asp Asn Ala Lys Asn Thr Val Phe Leu Gln Met
65                  70                  75                  80

Asn Asn Leu Lys Pro Glu Asp Thr Gly Val Tyr Tyr Cys Ala Ala Gly
                85                  90                  95

Pro Thr Phe Arg Gln Ser Arg Ala Thr Tyr Thr Asp Trp Gly Gln Gly
            100                 105                 110

Thr Gln Val Thr Val Ser Ser
        115
```

<210> SEQ ID NO 38
<211> LENGTH: 125
<212> TYPE: PRT
<213> ORGANISM: Artificial Sequence
<220> FEATURE:
<223> OTHER INFORMATION: synthetic construct

<400> SEQUENCE: 38

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ala Leu Ser Arg Ser
            20                  25                  30

Pro Met Ala Trp Phe Arg Gln Ala Pro Gly Lys Glu Arg Glu Phe Val
        35                  40                  45

Val His Trp Ile Ser Gly Ser Thr Tyr Tyr Ala Asp Ser Val Lys Gly
```

```
Arg Phe Thr Thr Ser Arg Asp Asn Ala Glu Asn Thr Val Tyr Leu Gln
 65                  70                  75                  80

Met Asn Ser Leu Lys Pro Glu Asp Thr Ala Val Tyr Tyr Cys Ala Ala
                 85                  90                  95

Gly Phe Ala Pro Asp Thr Pro Ser Ile Phe Thr Ser Pro Arg Thr Tyr
            100                 105                 110

Tyr Tyr Trp Gly Gln Gly Thr Gln Val Thr Val Ser Ser
        115                 120                 125
```

<210> SEQ ID NO 39
<211> LENGTH: 119
<212> TYPE: PRT
<213> ORGANISM: Artificial Sequence
<220> FEATURE:
<223> OTHER INFORMATION: synthetic construct

<400> SEQUENCE: 39

```
Glu Val Gln Leu Val Glu Ser Gly Gly Gly Leu Val Gln Ala Gly Gly
 1               5                  10                  15

Ser Leu Arg Leu Ser Cys Ala Ala Ser Gly Ser Thr Gly Ala Met Ala
                20                  25                  30

Trp Phe Arg Gln Ala Pro Gly Lys Glu Arg Asp Leu Val Ala Ser Ile
            35                  40                  45

Ser Arg Ser Gly Val Ser Thr Tyr Tyr Ala Asp Ser Val Lys Val Arg
 50                  55                  60

Phe Thr Ile Ser Arg Asp Asn Ala Lys Asn Thr Val Phe Leu Gln Met
 65                  70                  75                  80

Asn Asn Leu Lys Pro Glu Asp Thr Gly Val Tyr Tyr Cys Ala Ala Gly
                85                  90                  95

Pro Thr Phe Arg Gln Ser Arg Ala Thr Tyr Thr Asp Trp Gly Gln Gly
            100                 105                 110

Thr Gln Val Thr Val Ser Ser
        115
```

<210> SEQ ID NO 40
<211> LENGTH: 122
<212> TYPE: PRT
<213> ORGANISM: Artificial Sequence
<220> FEATURE:
<223> OTHER INFORMATION: synthetic construct

<400> SEQUENCE: 40

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Asn Ser Gly Gly Gly Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Arg Cys
                85                  90                  95

Ala Lys Tyr Tyr Glu Ala Asp Pro Ala Lys Asn Glu Tyr Asp Tyr Trp
            100                 105                 110
```

Gly Gln Gly Thr Gln Val Thr Val Ser Ser
        115                 120

<210> SEQ ID NO 41
<211> LENGTH: 121
<212> TYPE: PRT
<213> ORGANISM: Artificial Sequence
<220> FEATURE:
<223> OTHER INFORMATION: synthetic construct

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Val Thr Phe Asn
            20                  25                  30

Pro Met Gly Trp Tyr Arg Gln Ala Pro Gly Asn Gln Arg Glu Leu Val
        35                  40                  45

Ala Ser Ile Thr Ser Gly Gly Ala Asn Tyr Val Asp Ser Val Lys
    50                  55                  60

Gly Arg Phe Thr Ile Ser Val Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ile Phe Ser Ser Arg Leu Ser Trp Asp Asn Tyr Trp Gly
            100                 105                 110

Gln Gly Thr Gln Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: synthetic construct

<400> SEQUENCE: 42

Gly Gly Gly Gly Ser
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic construct

<400> SEQUENCE: 43

Lys Gly Pro Glu Trp
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic construct

<400> SEQUENCE: 44

Lys Glu Arg Glu Leu
1               5

<210> SEQ ID NO 45
<211> LENGTH: 5

```
<212> TYPE: PRT
<213> ORGANISM: Artificial Sequence
<220> FEATURE:
<223> OTHER INFORMATION: synthetic construct

<400> SEQUENCE: 45

Lys Gln Arg Glu Leu
 1               5

<210> SEQ ID NO 46
<211> LENGTH: 5
<212> TYPE: PRT
<213> ORGANISM: Artificial Sequence
<220> FEATURE:
<223> OTHER INFORMATION: synthetic construct

<400> SEQUENCE: 46

Lys Glu Arg Glu Phe
 1               5

<210> SEQ ID NO 47
<211> LENGTH: 5
<212> TYPE: PRT
<213> ORGANISM: Artificial Sequence
<220> FEATURE:
<223> OTHER INFORMATION: synthetic construct

<400> SEQUENCE: 47

Lys Val Arg Glu Leu
 1               5

<210> SEQ ID NO 48
<211> LENGTH: 5
<212> TYPE: PRT
<213> ORGANISM: Artificial Sequence
<220> FEATURE:
<223> OTHER INFORMATION: synthetic construct

<400> SEQUENCE: 48

Gln Gln Arg Glu Leu
 1               5

<210> SEQ ID NO 49
<211> LENGTH: 124
<212> TYPE: PRT
<213> ORGANISM: Artificial Sequence
<220> FEATURE:
<223> OTHER INFORMATION: synthetic construct

<400> SEQUENCE: 49

Gln Val Gln Leu Gln Glu Ser Gly Gly Gly Leu Val Gln Pro Gly Gly
 1               5                  10                  15

Ser Leu Arg Leu Ser Cys Ser Ala Ser Gly Phe Ser Leu Asp Ile Tyr
                20                  25                  30

Ala Ile Gly Trp Phe Arg Gln Ala Pro Gly Lys Glu Arg Glu Gly Val
            35                  40                  45

Ser Cys Ile Asn Ser Ser Gly Ser Ser Thr Tyr Tyr Ala Asp Ser Val
        50                  55                  60

Lys Gly Arg Phe Thr Ile Ser Arg Asp Asn Ala Lys Asn Thr Ile Tyr
65                  70                  75                  80

Leu Gln Met Asn Ser Leu Lys Pro Glu Asp Thr Ala Val Tyr Tyr Cys
                85                  90                  95

Ala Thr Gly Gly Cys Ser Pro Phe Gly Gly Val Ala Gly Val Lys Asp
               100                 105                 110
```

```
Tyr Trp Gly Gln Gly Thr Gln Val Thr Val Ser Ser
            115                 120

<210> SEQ ID NO 50
<211> LENGTH: 122
<212> TYPE: PRT
<213> ORGANISM: Artificial Sequence
<220> FEATURE:
<223> OTHER INFORMATION: synthetic construct

<400> SEQUENCE: 50

Gln Val Lys Leu Glu Glu Ser Gly Gly Gly Leu Val Gln Ala Gly Gly
  1               5                  10                  15

Ser Leu Arg Leu Ser Cys Ala Ala Ser Gly Arg Thr Phe Ser Thr Tyr
             20                  25                  30

Ser Met Gly Trp Phe Arg Arg Ala Pro Gly Lys Glu Arg Glu Phe Val
         35                  40                  45

Ala Ala Ile Ser Trp Ser Gly Gly Thr Thr Arg Tyr Thr Asn Ser Val
     50                  55                  60

Lys Gly Arg Phe Thr Ile Ser Lys Asp Asn Phe Gly Asn Thr Val Tyr
 65                  70                  75                  80

Leu Gln Met Asn Asn Leu Lys Pro Glu Asp Thr Ala Val Tyr Tyr Cys
                 85                  90                  95

Ala Thr Arg Tyr Ser Tyr Ser Thr Thr Pro Glu Glu Tyr Asp Leu Trp
            100                 105                 110

Gly Gln Gly Asn Gln Val Thr Val Ser Ser
            115                 120

<210> SEQ ID NO 51
<211> LENGTH: 123
<212> TYPE: PRT
<213> ORGANISM: Artificial Sequence
<220> FEATURE:
<223> OTHER INFORMATION: synthetic construct

<400> SEQUENCE: 51

Gln Val Gln Leu Gln Glu Ser Gly Gly Gly Leu Val Gln Ala Gly Gly
  1               5                  10                  15

Ser Leu Arg Leu Ser Cys Val Ala Ser Gly Gly Thr Phe Ser Gly Tyr
             20                  25                  30

Ala Met Ala Trp Phe Arg Gln Arg Pro Gly Lys Val Arg Glu Phe Val
         35                  40                  45

Ala Thr Ile Ser Arg Ser Ala Ser Thr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ala Lys Leu Gly Val Thr Ser Phe Tyr Arg Ser Tyr Ser Tyr
            100                 105                 110

Trp Gly Gln Gly Ile Gln Val Thr Val Ser Ser
            115                 120

<210> SEQ ID NO 52
<211> LENGTH: 124
<212> TYPE: PRT
<213> ORGANISM: Artificial Sequence
<220> FEATURE:
<223> OTHER INFORMATION: synthetic construct
```

<400> SEQUENCE: 52

```
Gln Val Gln Leu Gln Glu Ser Gly Gly Gly Leu Val Gln Pro Gly Gly
  1               5                  10                  15
Ser Leu Arg Leu Ser Cys Val Ala Ser Gly Asn Ile Phe Ser Ile Ser
             20                  25                  30
Ala Met Gly Trp Tyr Arg Gln Ala Pro Gly Gln Gln Arg Glu Leu Val
         35                  40                  45
Ala Ser Met Thr Asn Glu Gly Asn Thr Asn Tyr Ala Asp Ser Val Lys
     50                  55                  60
Gly Arg Phe Thr Ile Ser Arg Asp Asn Ala Lys Asn Thr Val Tyr Leu
 65                  70                  75                  80
Gln Met Asp Ser Leu Lys Pro Glu Asp Thr Ala Val Tyr Tyr Cys Asn
                 85                  90                  95
Ala Tyr Tyr Tyr Tyr Asn Glu Tyr Asp Pro Asp Ser Asp Ala Met Asp
            100                 105                 110
Tyr Trp Gly Lys Gly Thr Leu Val Thr Val Ser Ser
            115                 120
```

<210> SEQ ID NO 53
<211> LENGTH: 251
<212> TYPE: PRT
<213> ORGANISM: Artificial Sequence
<220> FEATURE:
<223> OTHER INFORMATION: synthetic construct

<400> SEQUENCE: 53

```
Glu Val Gln Leu Val Glu Ser Gly Gly Gly Phe Val Gln Ala Gly Gly
  1               5                  10                  15
Ser Leu Arg Leu Ser Cys Ala Ala Ser Gly Ser Ile Phe Ser Ile Asn
             20                  25                  30
Ala Met Gly Trp Tyr Arg Gln Ala Pro Gly Lys Gln Arg Glu Leu Val
         35                  40                  45
Ala Ala Ile Thr Ser Gly Gly Ser Thr Asn Tyr Ala Asp Ser Val Lys
     50                  55                  60
Gly Arg Phe Thr Ile Ser Arg Asp Asn Ala Lys Asn Thr Leu Tyr Leu
 65                  70                  75                  80
Gln Met Asn Ser Leu Lys Pro Glu Asp Thr Ala Val Tyr Tyr Cys Ser
                 85                  90                  95
Ala Val Thr Ile Leu Leu Thr Ser Gly Gly Trp Gly Ser Gly Asn Asp
            100                 105                 110
Tyr Trp Gly Gln Gly Thr Gln Val Thr Val Ser Ser Gly Gly Gly Gly
            115                 120                 125
Ser Glu Val Gln Leu Val Glu Ser Gly Gly Gly Leu Val Gln Ala Gly
        130                 135                 140
Gly Ser Leu Arg Leu Ser Cys Ala Ala Ser Gly Arg Thr Phe Ser Thr
145                 150                 155                 160
Tyr Ser Met Gly Trp Phe Arg Arg Ala Pro Gly Lys Glu Arg Glu Phe
                165                 170                 175
Val Ala Ala Ile Ser Trp Ser Gly Gly Thr Thr Arg Tyr Thr Asn Ser
            180                 185                 190
Val Lys Gly Arg Phe Thr Ile Ser Lys Asp Asn Phe Gly Asn Thr Val
        195                 200                 205
Tyr Leu Gln Met Asn Asn Leu Lys Pro Glu Asp Thr Ala Val Tyr Tyr
    210                 215                 220
```

```
Cys Ala Thr Arg Tyr Ser Tyr Ser Thr Thr Pro Glu Glu Tyr Asp Leu
225                 230                 235                 240

Trp Gly Gln Gly Asn Gln Val Thr Val Ser Ser
            245                 250
```

<210> SEQ ID NO 54
<211> LENGTH: 259
<212> TYPE: PRT
<213> ORGANISM: Artificial Sequence
<220> FEATURE:
<223> OTHER INFORMATION: synthetic construct

<400> SEQUENCE: 54

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ile Ile Gly Trp Phe Arg Gln Ala Pro Gly Lys Glu Arg Glu Gly Ile
        35                  40                  45

Ser Cys Ile Ser Ser Ser Asp Gly Ser Thr Tyr Tyr Ala Asp Ser Val
    50                  55                  60

Thr Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Ala Lys Trp Pro Tyr Gly Thr Tyr Ser Phe Arg Arg Cys
            100                 105                 110

Arg Arg Ala Ser Phe Asp Ser Trp Gly Gln Gly Thr Gln Val Thr Val
        115                 120                 125

Ser Ser Gly Gly Gly Gly Ser Glu Val Gln Leu Val Glu Ser Gly Gly
130                 135                 140

Gly Leu Val Gln Pro Gly Gly Ser Leu Arg Leu Ser Cys Val Ala Ser
145                 150                 155                 160

Gly Asn Ile Phe Ser Ile Ser Ala Met Gly Trp Tyr Arg Gln Ala Pro
                165                 170                 175

Gly Gln Gln Arg Glu Leu Val Ala Ser Met Thr Asn Glu Gly Asn Thr
            180                 185                 190

Asn Tyr Ala Asp Ser Val Lys Gly Arg Phe Thr Ile Ser Arg Asp Asn
        195                 200                 205

Ala Lys Asn Thr Val Tyr Leu Gln Met Asp Ser Leu Lys Pro Glu Asp
    210                 215                 220

Thr Ala Val Tyr Tyr Cys Asn Ala Tyr Tyr Tyr Asn Glu Tyr Asp
225                 230                 235                 240

Pro Asp Ser Asp Ala Met Asp Tyr Trp Gly Lys Gly Thr Leu Val Thr
                245                 250                 255

Val Ser Ser
```

<210> SEQ ID NO 55
<211> LENGTH: 253
<212> TYPE: PRT
<213> ORGANISM: Artificial Sequence
<220> FEATURE:
<223> OTHER INFORMATION: synthetic construct

<400> SEQUENCE: 55

```
Glu Val Gln Leu Val Glu Ser Gly Gly Gly Leu Val Gln Ala Gly Asp
1               5                   10                  15
```

```
Ser Leu Arg Leu Ser Cys Ala Ala Ser Gly Arg Ser Ile Ser Leu Tyr
            20                  25                  30

Ala Met Ala Trp Phe Arg Gln Ala Ala Gly Lys Glu Arg Glu Phe Val
        35                  40                  45

Ala Ala Ile Asn Trp Ser Gly Gly Ser Thr Tyr Ala Asp Ser Val
    50                  55                  60

Lys Gly Arg Phe Ser Ile Ser Arg Asp Thr Ala Lys Asn Thr Val Tyr
65                  70                  75                  80

Leu Thr Met Asn Ser Leu Lys Pro Glu Asp Thr Ala Val Tyr Tyr Cys
                85                  90                  95

Ala Thr Asp Ser Ser Thr Thr Val Val Phe Tyr Ser Ser Asn Ser
                100                 105                 110

Leu Arg Tyr Trp Gly Gln Gly Thr Gln Val Thr Val Ser Ser Gly Gly
            115                 120                 125

Gly Gly Ser Glu Val Gln Leu Val Glu Ser Gly Gly Leu Val Gln
    130                 135                 140

Ala Gly Gly Ser Leu Arg Leu Ser Cys Ala Ala Ser Gly Arg Thr Phe
145                 150                 155                 160

Ser Thr Tyr Ser Met Gly Trp Phe Arg Arg Ala Pro Gly Lys Glu Arg
                165                 170                 175

Glu Phe Val Ala Ala Ile Ser Trp Ser Gly Gly Thr Thr Arg Tyr Thr
            180                 185                 190

Asn Ser Val Lys Gly Arg Phe Thr Ile Ser Lys Asp Asn Phe Gly Asn
                195                 200                 205

Thr Val Tyr Leu Gln Met Asn Asn Leu Lys Pro Glu Asp Thr Ala Val
            210                 215                 220

Tyr Tyr Cys Ala Thr Arg Tyr Ser Tyr Ser Thr Thr Pro Glu Glu Tyr
225                 230                 235                 240

Asp Leu Trp Gly Gln Gly Asn Gln Val Thr Val Ser Ser
                245                 250

<210> SEQ ID NO 56
<211> LENGTH: 247
<212> TYPE: PRT
<213> ORGANISM: Artificial Sequence
<220> FEATURE:
<223> OTHER INFORMATION: synthetic construct

<400> SEQUENCE: 56

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Arg Asp
            20                  25                  30

Val Met Gly Trp Phe Arg Gln Ala Pro Gly Lys Val Arg Glu Val Val
        35                  40                  45

Gly Ser Ile Thr Trp Ser Gly Gly Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Gly Val Tyr Tyr Cys
                85                  90                  95

Ala Val Ala Glu Leu Gly Ser Thr Tyr Asn Asp Trp Gly Gln Gly Thr
                100                 105                 110

Gln Val Thr Val Ser Ser Gly Gly Gly Gly Ser Glu Val Gln Leu Val
            115                 120                 125
```

Glu Ser Gly Gly Gly Leu Val Gln Pro Gly Gly Ser Leu Arg Leu Ser
                130                 135                 140

Cys Ser Ala Ser Gly Phe Ser Leu Asp Ile Tyr Ala Ile Gly Trp Phe
145                 150                 155                 160

Arg Gln Ala Pro Gly Lys Glu Arg Glu Gly Val Ser Cys Ile Asn Ser
                    165                 170                 175

Ser Gly Ser Ser Thr Tyr Tyr Ala Asp Ser Val Lys Gly Arg Phe Thr
                180                 185                 190

Ile Ser Arg Asp Asn Ala Lys Asn Thr Ile Tyr Leu Gln Met Asn Ser
                195                 200                 205

Leu Lys Pro Glu Asp Thr Ala Val Tyr Tyr Cys Ala Thr Gly Gly Cys
210                 215                 220

Ser Pro Phe Gly Gly Val Ala Gly Val Lys Asp Tyr Trp Gly Gln Gly
225                 230                 235                 240

Thr Gln Val Thr Val Ser Ser
                245

<210> SEQ ID NO 57
<211> LENGTH: 179
<212> TYPE: PRT
<213> ORGANISM: Artificial Sequence
<220> FEATURE:
<223> OTHER INFORMATION: synthetic construct

<400> SEQUENCE: 57

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
                20                  25                  30

Ile Ile Gly Trp Phe Arg Gln Ala Pro Gly Lys Glu Arg Glu Gly Ile
            35                  40                  45

Ser Cys Ile Ser Ser Ser Asp Gly Ser Thr Tyr Tyr Ala Asp Ser Val
        50                  55                  60

Thr Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Ala Lys Trp Pro Tyr Gly Thr Tyr Ser Phe Arg Arg Cys
            100                 105                 110

Arg Arg Ala Ser Phe Asp Ser Trp Gly Gln Gly Thr Gln Val Thr Val
        115                 120                 125

Ser Ser Ala Ala Ala Gly Pro Gln Gly Ile Trp Gly Gln Ala Ala Ala
    130                 135                 140

Val Thr Lys His Leu Asn Gln Ile Ser Gln Ser Tyr Val Asp Ala Asp
145                 150                 155                 160

Tyr Lys Asp Asp Asp Asp Lys Ser Ala Ala His His His His His His
                165                 170                 175

Ser Ala Ala

<210> SEQ ID NO 58
<211> LENGTH: 171
<212> TYPE: PRT
<213> ORGANISM: Artificial Sequence
<220> FEATURE:
<223> OTHER INFORMATION: synthetic construct

<400> SEQUENCE: 58

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Asp Phe Val
        35                  40                  45

Ala Ala Ile Ser Trp Ser Gly Ser Thr Tyr Tyr Thr Gly Ser Val
    50                  55                  60

Lys Gly Arg Phe Asn Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Gly Pro Arg Ser Ala Tyr Tyr Asp Asp Tyr Gly Tyr Asp Tyr
            100                 105                 110

Trp Gly Gln Gly Thr Gln Val Thr Val Ser Ser Ala Ala Ala Gly Pro
        115                 120                 125

Gln Gly Ile Trp Gly Gln Ala Ala Ala Pro Trp His Leu Ser Ser Gln
    130                 135                 140

Tyr Ser Arg Thr Val Asp Ala Asp Tyr Lys Asp Asp Asp Lys Ser
145                 150                 155                 160

Ala Ala His His His His His His Ser Ala Ala
            165                 170

<210> SEQ ID NO 59
<211> LENGTH: 121
<212> TYPE: PRT
<213> ORGANISM: Artificial Sequence
<220> FEATURE:
<223> OTHER INFORMATION: synthetic construct

<400> SEQUENCE: 59

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Ile Ser Ser Ser Tyr
            20                  25                  30

Asp Met Gly Trp Phe Arg Gln Ala Pro Gly Lys Glu Arg Glu Phe Val
        35                  40                  45

Ala Ala Ile Ser Trp Ser Gly Gly Thr Thr Asp Tyr Ala Asp Ser Val
    50                  55                  60

Lys Gly Arg Phe Ala Ile Ser Lys Asp Asn Lys Asn Ala Val Tyr
65                  70                  75                  80

Leu Gln Met Asn Ser Leu Lys Pro Glu Asp Thr Ala Val Tyr Tyr Cys
                85                  90                  95

Ala Ala Val Thr Lys His Leu Asn Gln Ile Ser Gln Tyr Trp Gly
            100                 105                 110

Gln Gly Thr Gln Val Thr Val Ser Ser
        115                 120

<210> SEQ ID NO 60
<211> LENGTH: 130
<212> TYPE: PRT
<213> ORGANISM: Artificial Sequence
<220> FEATURE:
<223> OTHER INFORMATION: synthetic construct

<400> SEQUENCE: 60

Glu Val Gln Leu Val Glu Ser Gly Gly Gly Leu Val Gln Ala Gly Gly
1               5                   10                  15

-continued

```
Ser Leu Arg Leu Ser Cys Ala Ala Ser Gly Phe Thr Phe Asp Asp Tyr
            20                  25                  30

Ile Ile Gly Trp Phe Arg Gln Ala Pro Gly Lys Glu Arg Glu Gly Ile
        35                  40                  45

Ser Cys Ile Ser Ser Ser Asp Gly Ser Thr Tyr Tyr Ala Asp Ser Val
    50                  55                  60

Thr Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Ala Lys Trp Pro Tyr Gly Thr Tyr Ser Phe Arg Arg Cys
            100                 105                 110

Arg Arg Ala Ser Phe Asp Ser Trp Gly Gln Gly Thr Gln Val Thr Val
        115                 120                 125

Ser Ser
    130

<210> SEQ ID NO 61
<211> LENGTH: 130
<212> TYPE: PRT
<213> ORGANISM: Artificial Sequence
<220> FEATURE:
<223> OTHER INFORMATION: synthetic construct

<400> SEQUENCE: 61

Glu Val Gln Leu Val Glu Ser Gly Gly Gly Leu Val Gln Ala Gly Gly
 1               5                  10                  15

Ser Leu Arg Leu Ser Cys Ala Ala Ser Gly Phe Thr Phe Asp Asp Tyr
            20                  25                  30

Ile Ile Gly Trp Phe Arg Gln Ala Pro Gly Lys Glu Arg Glu Gly Ile
        35                  40                  45

Ser Cys Ile Ser Ser Ser Asp Gly Ser Thr Tyr Tyr Ala Asp Ser Val
    50                  55                  60

Thr Gly Arg Phe Thr Ile Ser Ser Asp Asn Ala Asn Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Ala Lys Trp Pro Tyr Gly Thr Tyr Ser Phe Arg Arg Cys
            100                 105                 110

Arg Arg Ala Ser Phe Asp Ser Trp Gly Gln Gly Thr Gln Val Thr Val
        115                 120                 125

Ser Ser
    130
```

VHH FOR APPLICATION IN TISSUE REPAIR, ORGAN REGENERATION, ORGAN REPLACEMENT AND TISSUE ENGINEERING

CROSS-REFERENCE TO RELATED APPLICATIONS

This application is the national phase of PCT application PCT/NL2010/050700 having an international filing date of 21 Oct. 2010, which claims benefit of European patent application No. 09173832.8 filed 22 Oct. 2009. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 313632014000Seqlist.txt | Jul. 12, 2012 | 65,564 bytes |

TECHNICAL FIELD OF THE INVENTION

The present invention relates to single heavy chain variable domain antibodies (VHHs) which have been functionalized and can be used for tissue engineering. These VHHs can provide a characteristic that functions to promote tissue growth and improve the attachment of an implant to surrounding tissue.

BACKGROUND OF THE INVENTION

Medical implants or prostheses function to replace or augment various structures and tissues in the body. Medical implants include, for example, intervertebral disc replacement devices, spinal fixation systems, facet arthroplasty devices, artificial hips, bone screws, bone plates and rods, prosthetic knee replacements, arterial stents, pacemakers, heart valves, artificial hearts, artificial sphincters, etc. The effectiveness of medical implants sometimes is highly dependent upon the implant's interactions with surrounding tissues. For example, in the case of bone implants, it may be desirable that tissue attachment from adjacent bony structures occur at the bone implant's surface in order to integrate the bone implant with the rest of the skeletal system.

In a biological system, several elements are primordial for survival. The dissection of the different elements of biological systems is translated in tissue engineering by three general ingredients; the cells, biological active factors such as growth factors or growth factor antagonists and scaffolds. The cells (I) are extracted from a donor, who is the patient himself, another person, preferably a close relative of the patient (preferably having the same germ lines) or an animal (autogenic, allogenic and xenogenic transplantation, respectively). The cells can either be a stem cell, a tissue progenitor cells or a differentiated tissue specific cell; the biological active factors (II) attract tissue forming cells at the site of implantation, and/or promote cell adhesion, stimulate proliferation, and guide differentiation of progenitor cells in the desired cell type to reconstitute a functional tissue; the scaffolds (III) are made of a biocompatible material being either synthetic or natural in origin. The scaffold creates the optimal microenvironment in which the various cell types can mature into a functional tissue. Maturation of the constructs can occur in vitro or in vivo after implantation of the scaffold at the desired location in the body. The integration/interaction of these elements leads to the creation of new tissues.

Cell life depends on chemical interactions and reactions, which are extremely well coordinated in time and space and are under the influence of genetic instructions as well as the environment. The aim of a scaffold material, selected for a tissue engineering application, is to create an optimal microenvironment for de novo tissue formation for example by mimicking the natural extracellular matrix (ECM). The ECM is a net of secreted products that surround and support cells in tissue. The ECM consists of a mixture of structural and functional molecules organized in a three-dimensional structure that is specific for each tissue type. Most of these molecules are well known; they form a complex mixture of proteins and polysaccharides. The ECM functions as a reservoir of bioactive molecules such as growth factors and growth factor antagonists. The bioactive molecules that reside in the ECM and their spatial distribution provide a cocktail of biological signals. The balance in activation of biological processes by arrays of growth factors and the inhibition of their activity by respective antagonists determines all biological response such as cell proliferation, cell differentiation, cell maturation, cell death and the formation of a functional organ. The ECM is a reservoir for growth factors and antagonists. Since cellular functions are regulated by cell-cell communication, cell-substratum interactions, and soluble factors, it is of prior importance to select an adequate biomaterial, and select an adequate set of growth factors and/or growth factor antagonists to incorporate in the scaffold for optimal tissue formation. Each tissue requires its own set of conditions. Viewing the biomaterials as units to interact with biological systems rather than inert substances, innovative designs in the field of biomaterials are needed to optimize the constructs for functional tissue formation.

The adsorption/incorporation of proteins onto/into biomaterials can influence material properties and degradation. The kind of interactions between proteins and an implant is determined by the properties of both (e.g. size, charge, structural stability, topography or chemical composition).

There is a need for a method that more fully regulates the interactions between medical implants and surrounding tissues and that discourages disadvantageous interactions of medical implants and surrounding tissues. Additionally, there is a need for a method to guide tissue attachment to medical implants. There also is a need for a method that stimulates advantageous interactions of medical implants and surrounding tissues.

The challenge faced by researchers in the field is to make implants with improved properties such as better attachment to the surrounding tissue, improved growth, differentiation and migration of cells responsible for wound healing. It is therefore an object of the present invention to substantially overcome or ameliorate one or more disadvantages of the prior art.

SUMMARY OF THE INVENTION

The present invention provides a VHH which binds to a growth factor or to an antagonist of said growth factor.

In a further aspect the invention provides the VHH according to the invention for use as a medicament. Preferably said VHH is used for the treatment of a patient in need of an implant.

Advantageously, in accordance with the invention use is made of a functionalized VHH. A VHH which is functionalized according to the invention can bind to an implant. An advantage thereof is that by increasing the affinity of said VHH for an implant, the presence of said VHH in an implant can be controlled in space specific manner. In addition, the affinity of said VHH for said implant also allows the release of said VHH in a time specific manner, thereby resulting in a controlled release of said VHH. Preferably, said implant comprises a biomaterial. Preferably, said biomaterial comprises a hyaluronic acid, chitosan, dextran, hyaluronic acid, heparin or heparan starch. Preferably, said cells are selected from the group of natural biological tissues including bone tissue and cartilage tissue. Preferably, said biomaterial comprises poly lactic acid (PLA), a polyalkyleneoxide-polyalkyle-terephtalate block copolymer, (preferably polyethylene oxide-polybutylene terephtalate block copolymers), poly-L-lactic acid (PLLA), polyglycolic lactic acid (PGLA), polyglycolic acid (PGA), poly(amido amine)s, poly(caprolactone), polyethylene; a gel based on alginate, a Poly-N-isopropylacrylamid gel or PEG-PBT. In another preferred embodiment, said biomaterial comprises a biocompatible ceramic, a biocompatible glass, a biocompatible metal or a biocompatible polymer. Preferably, said metal is titanium. In a preferred embodiment, said metal is coated with hydroxyapatite or calciumphosphate.

One preferred way of accomplishing the binding between the VHH according to the invention and the implant is by providing the VHH with a functional group which can bind to an implant via chemical crosslinking. Another preferred way is by incorporating into said VHH an amino acid sequence which binds to an implant. Preferably, said amino acid sequence which binds to an implant is selected from the group consisting of VTKHLNQISQSY (SEQ ID NO:1) and APWHLSSQYSRT (SEQ ID NO:2) in case the surface of the implant contains hydroxyapatite.

An advantage is that the integration of a VHH which binds to a growth factor or a growth factor antagonist improves cell attachment or growth of cells at the implants or of the surrounding tissue or it accelerates differentiation and migration of relevant cells in the implant or in the surrounding tissue and said use increases the successful regeneration, reconstruction and replacement of lost and worn out tissues. Without being bound by theory, it is believed that as a result of binding between said VHH and said growth factor or said antagonist, the balance between factors that stimulate and factors that inhibit cell proliferation, cell differentiation, cell maturation, cell death and the formation of a functional organ cell growth is altered such that a better regeneration is achieved. Highly preferred are VHHs comprising the amino acid sequence selected from the sequences as listed in Table 8.

In a preferred embodiment, said VHH comprises the amino acid sequence selected from the sequences as listed in Table 1, Table 2 and Table 3.

The invention further provides a VHH which binds to an implant.

Preferably, said VHH according to the invention is provided with a functional group which binds to an implant or can be bound to an implant via chemical cross linking. Preferably, said functional group is a glycosyl group present at one of the VHH's short loops 1, 2, 3, 5 [FIG. 5], a peptide bound to said functionalized VHH via a cysteine or methionine residue present in the last 10 amino acids of the C terminal end of said VHH, with the exception of the last amino acid, or an unnatural amino acid, preferably a Tyr-azide or Tyr-alkyn, capable of chemical cross linking to respective residues in an implant or through NHS chemistry.

Preferably, said VHH comprises the amino sequence selected from the sequences listed in Table 9.

The growth factor preferably comprises a Transforming growth factor beta (TGFbeta), Hedgehog, Wnt, Epidermal growth factor (EGF), a Bone Morphogenic Protein (BMPs), or a Fibroblast growth factor (FGF).

Preferably, said antagonist comprises a BMP antagonist, preferably Noggin or Gremlin, a Wnt-antagonist, preferably Dkk1, or FrzB.

Preferably said antagonist comprises a dual antagonist of BMP and Wnt, preferably Cerberus or sclerostin.

Preferably, said VHH comprises the amino acid sequence selected from the sequences as listed in Table 1, Table 2 and Table 3.

The invention further provides VHH which binds to a biomaterial. These VHH can suitably be used as a linking protein to bind a biomolecule to a biomaterial. Said VHH which binds to a biomaterial is therefore very suitable for binding the VHH according to the invention to an implant. In a preferred embodiment, said VHH comprises the amino acid sequence selected from the sequences as listed in Table 4, Table 5 and Table 6.

Further provided is the use of a fusion protein comprising at least two VHHs according to the invention. Preferably, said fusion protein comprises at least one VHH is a VHH which binds to a growth factor and/or an antagonist of such growth factor according to the invention. Preferably, said fusion protein comprises at least one VHH is a VHH which binds to an implant according to the invention. In one embodiment, said fusion protein comprises a first and a second VHH which binds to an implant. In a further preferred embodiment said first VHH binds to a first epitope and said second VHH binds to a second epitope of the same molecule present in said implant.

In a preferred embodiment, said fusion protein comprises the amino acid sequence selected from the sequences as listed in Table 7.

Further provided is a multimer composed of polymerized monomers, wherein said monomers comprise said fusion protein or a VHH according to the invention. Preferably, said multimer comprises less than 5 monomers.

Further provided is a protein complex comprising the VHH which binds to a growth factor or a growth factor antagonist according to the invention, or the fusion protein according to the invention and a growth factor or antagonist to a growth factor which binds to said VHH or said fusion protein. These protein complexes can suitably be used in implants. Preferably, said protein complexes are attached to an implant.

The invention further provides an implant comprising the VHH which binds to a growth factor or a growth factor antagonist according to the invention, the fusion protein according to the invention and/or the protein complex according to the invention.

Further provided is a method for the preparation of said implant comprising steps of loading said implant with the VHH which binds to a growth factor or a growth factor antagonist according to the invention, the fusion protein according to the invention and/or the protein complex according to the invention.

In a preferred embodiment, said loading is performed using microcontact printing.

The invention further provides the implant obtainable by said method.

Further provided is a method of treatment of a patient suffering from a tissue defect comprising providing the patient with the implant according to the invention to repair said tissue defect.

Also provided is a method of repairing a tissue defect in a patient in need thereof comprising the step of providing the patient with an implant and with the VHH which binds to a growth factor or a growth factor antagonist according to the invention, the fusion protein according to the invention and/or the protein complex according to the invention.

BRIEF DESCRIPTION OF THE DRAWINGS

FIG. 7B shows that binding between the fusion protein and hydroxyapatite takes place in a dose-response manner. For this experiment, three plates of hydroxyapatite of a homogeneous size range (1 mm$^2$) were incubated with 2% BSA in PBS to achieve blocking of non specific binding sites, and subsequently incubated with a serial dilution of the F fusion protein in the absence or presence of 1 µg or 5 µg of the VHH binding to hydroxyapatite (MA). After washing, bound F fusion proteins were detected via the FLAG tag (as described in the examples), which differentiate them from the MA VHH, which contains a myc tag. Competition between the MA VHH and the F bispecific fusion protein resulted in a reduction of about 50% of binding compared to binding with only the F fusion protein. No difference in competition was noticed between different concentrations of 1 µg and 5 µg of the MA VHH. This result confirms that binding of the fusion proteins to biomaterials is effective through binding between the anti-hydroxyapatite VHH (MA) and hydroxyapatite.

DETAILED DESCRIPTION OF THE INVENTION

Definitions

Figure 1A:
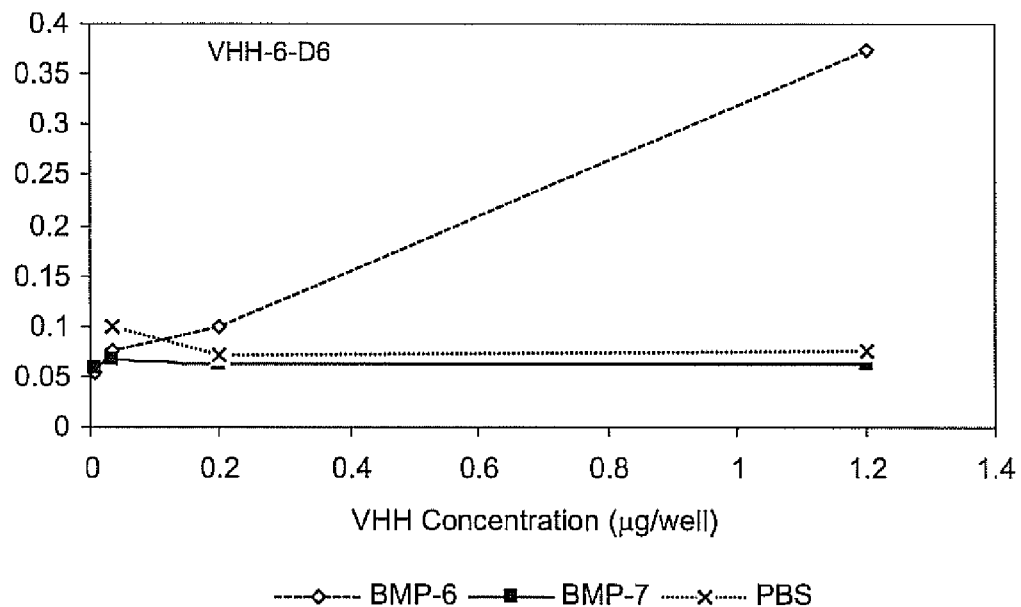
FIG. 1 shows the binding specificity of the VHH selected against BMPs as determined by solid phage ELISA. The indicated amounts of VHHs were incubated with wells coated with ~200 ng BMP6, 200 ng BMP7 or no BMPs (PBS). After several washes, bound VHHs were detected with a rabbit anti-VHH serum and a Donkey anti-rabbit antibody coupled to a peroxidase. The amount of converted OPD (Absorbance at 490 nm; A 490 nm) is proportional to the amount of bound VHHs. ELISA showed that some VHHs selected against a certain target have specific binding to the target antigen (VHH-6-D6, VHH-6-C1, VHH-7-B8, VHH-7-F11), whereas other VHH showed cross-reactivity to two antigens (VHH-6-C2).
Figure 1B:
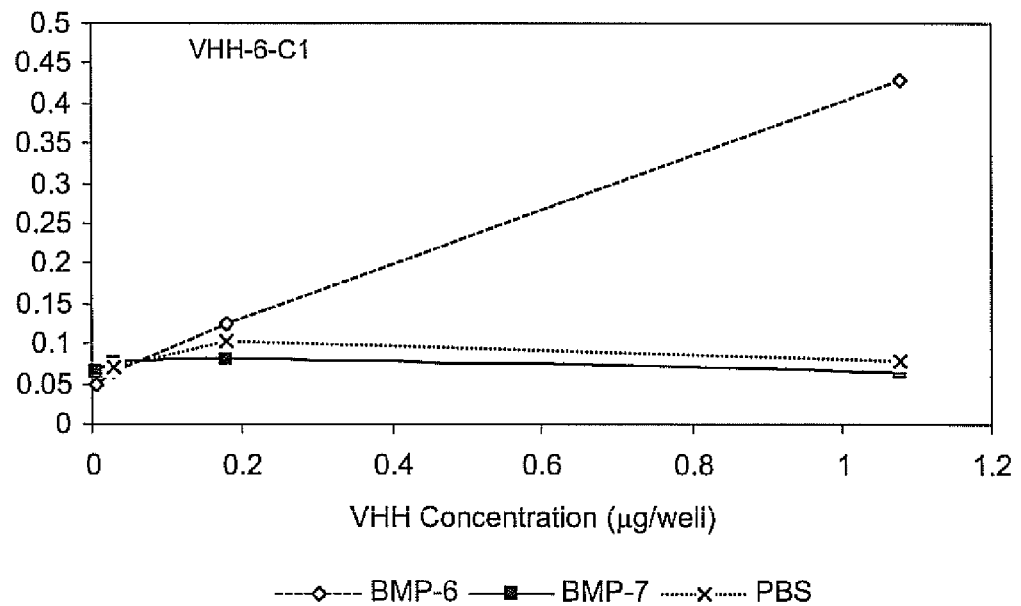
Figure 1C:
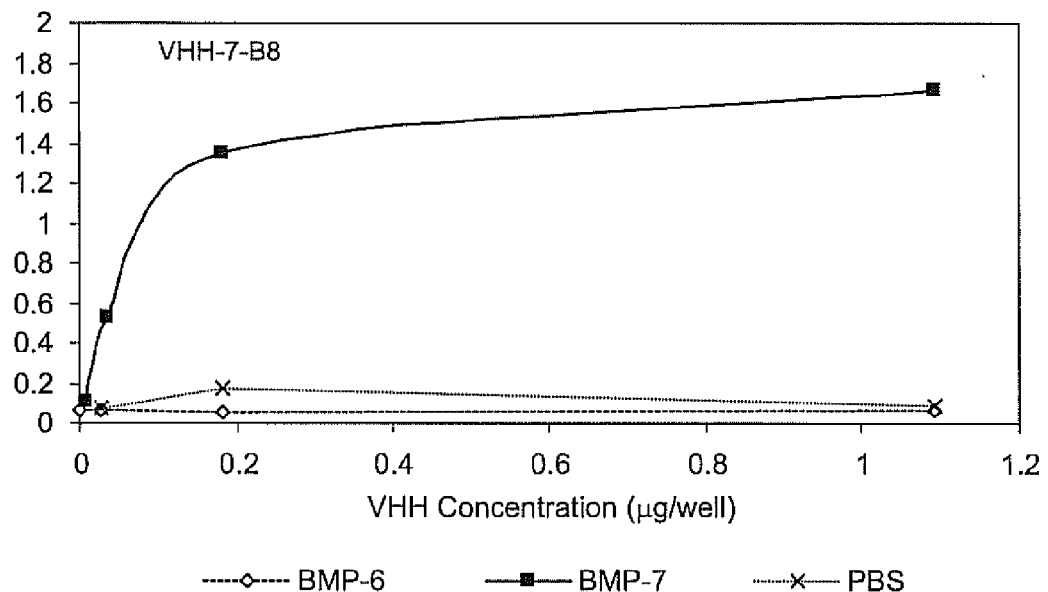
Figure 1D:
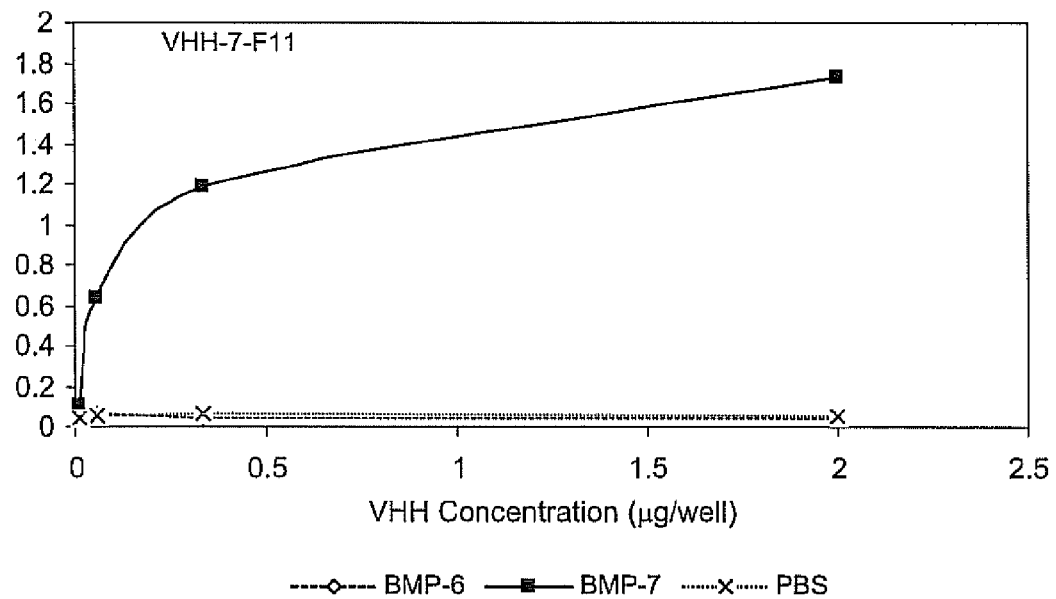
Figure 1E:
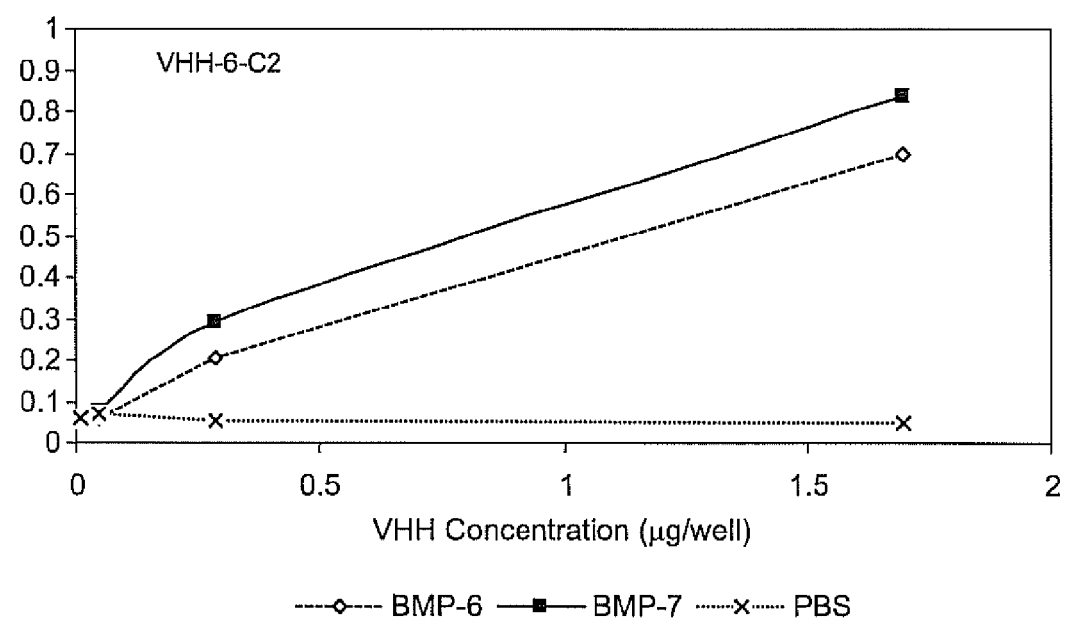
Figure 2A:
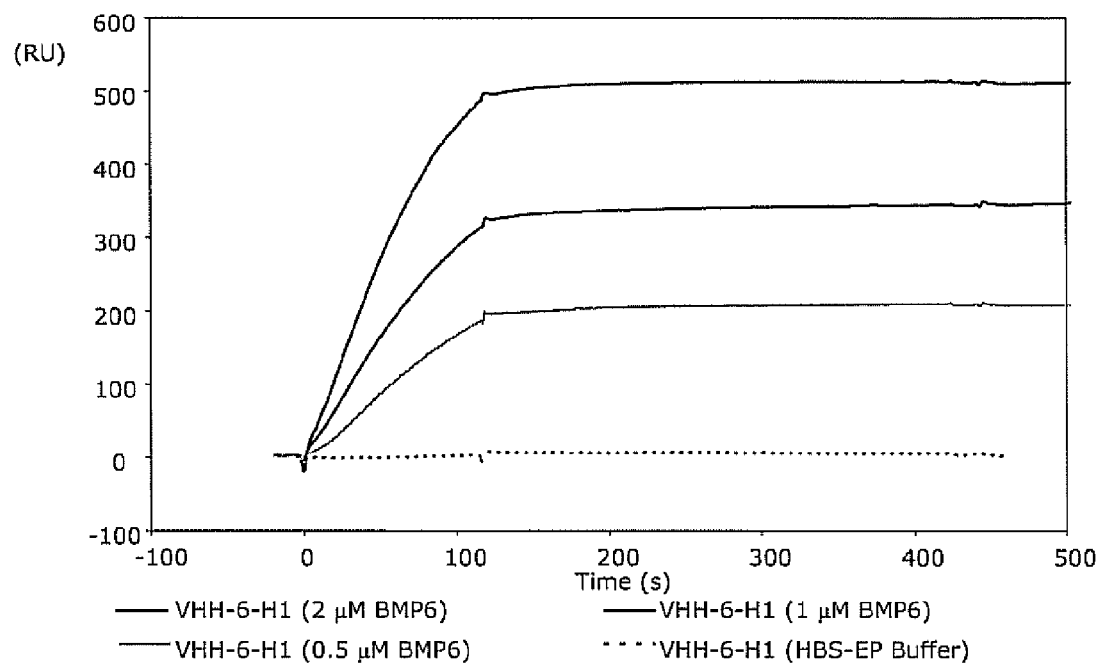
FIG. 2 shows the results of Surface Plasmon Resonance (SPR) of the VHHs after immobilization to a solid surface (CM5 biacore sensor chip). The VHH was coupled to the CM5 chip in an unspecific manner using NHS-chemistry. Binding of the VHH to the antigen is measured by the increase in response units after the end of antigen injection (~2 min). VHH-6-H1 shows affinity to the cognate antigen BMP6 and cross affinity to BMP7. BMP7 could still bind to VHH loaded with BMP6 indicating that the VHH binds the two morphogens by different sites. VHH-7-F11 shows specific affinity to the cognate antigen BMP7, and no cross reactivity to BMP6 in accordance with the solid phase VHH ELISA results. An irrelevant VHH (VHH-NR) directed against integrin did not show any binding to the two BMPs.
Figure 2B:
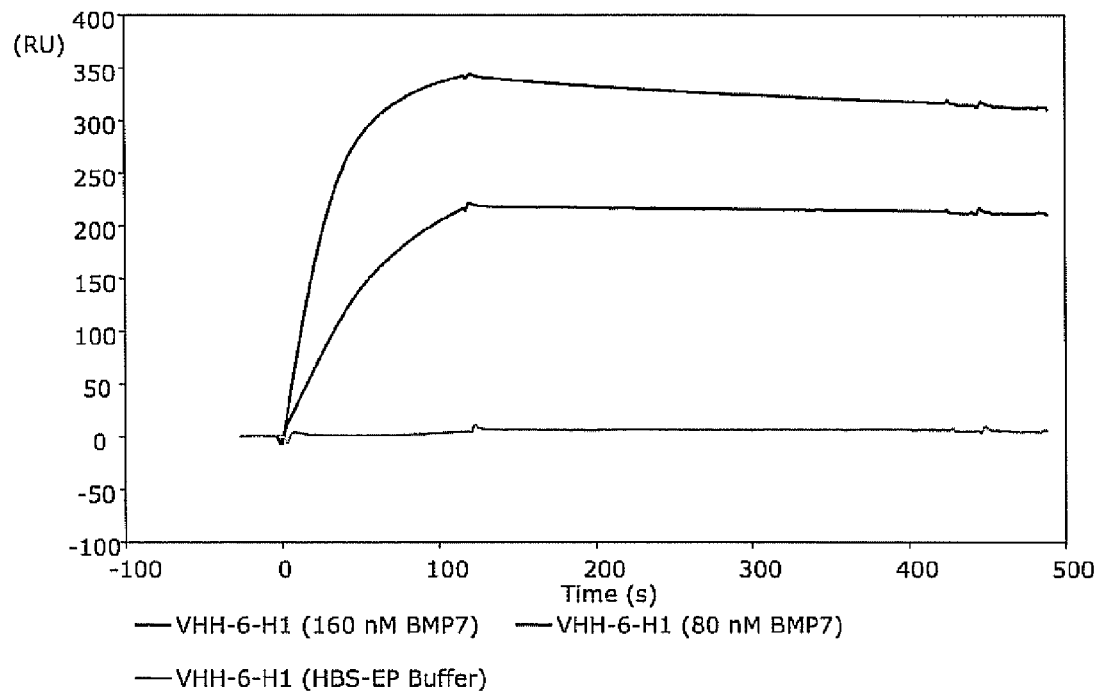
Figure 2C:
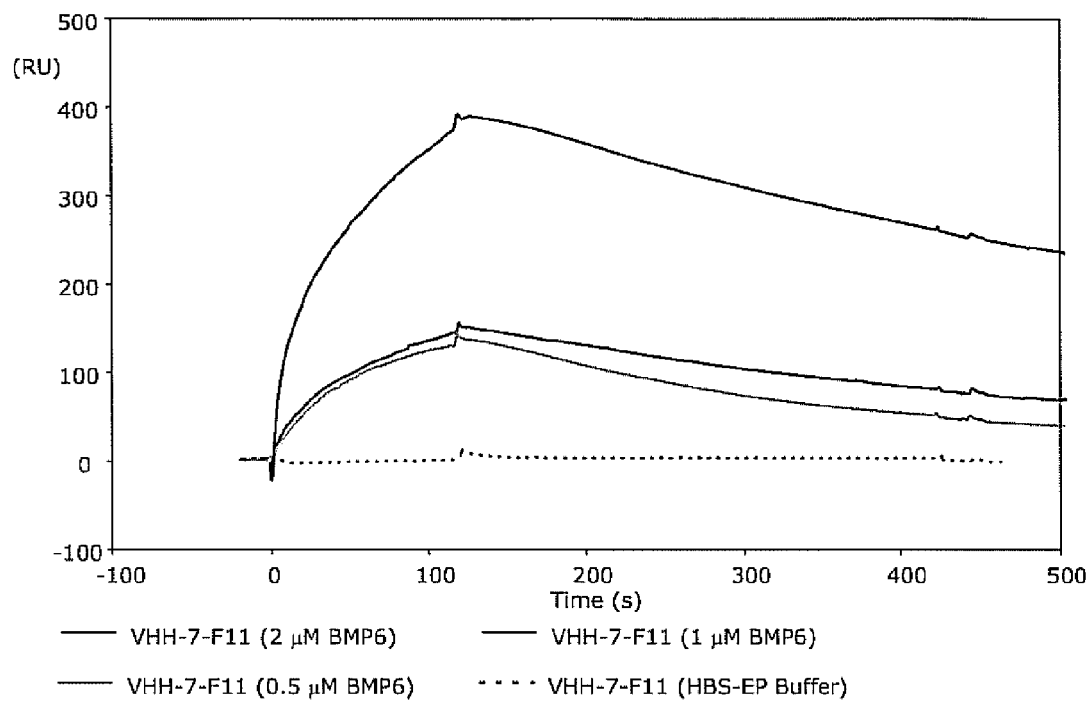
Figure 2D:
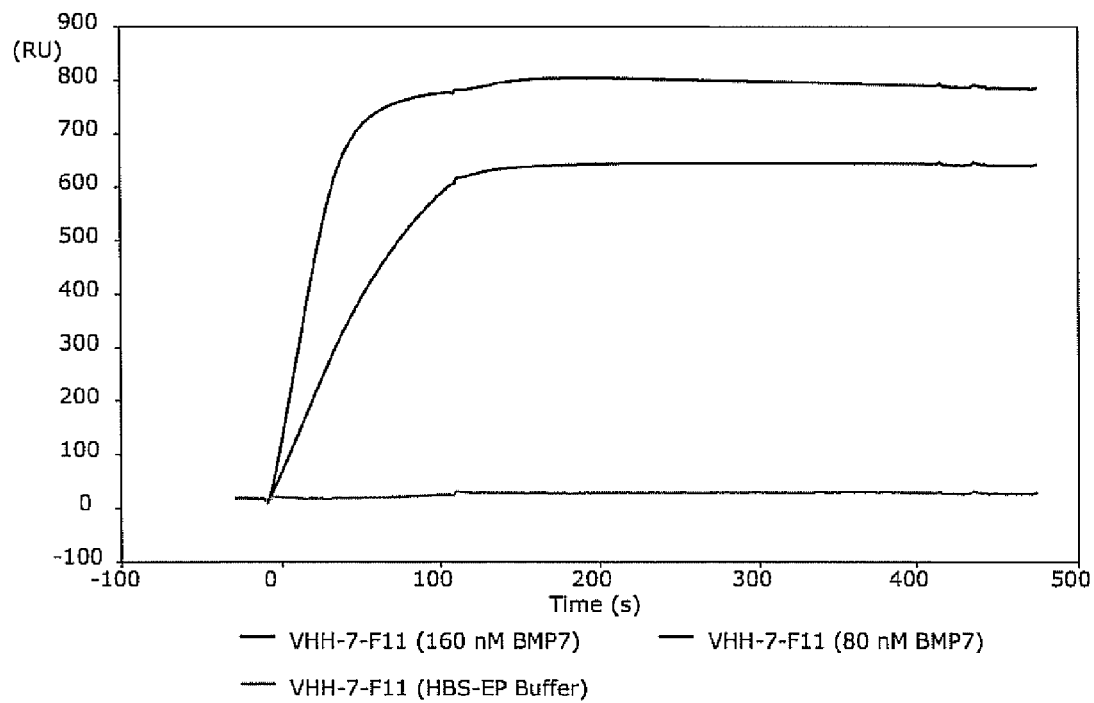
Figure 2E:
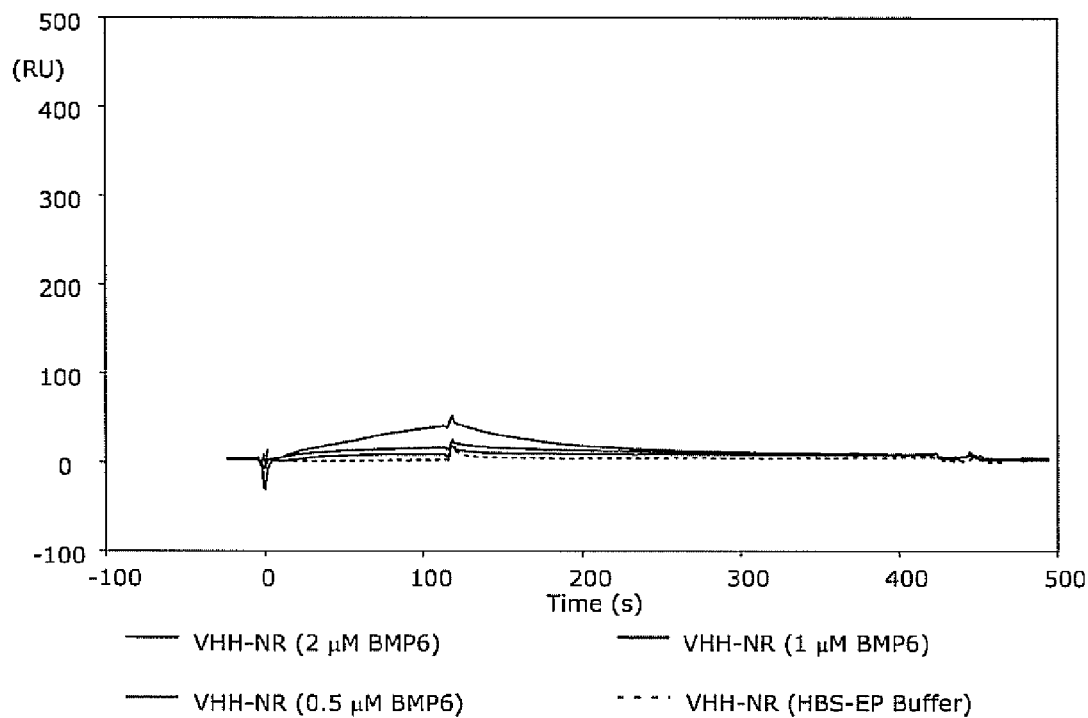
Figure 2F:
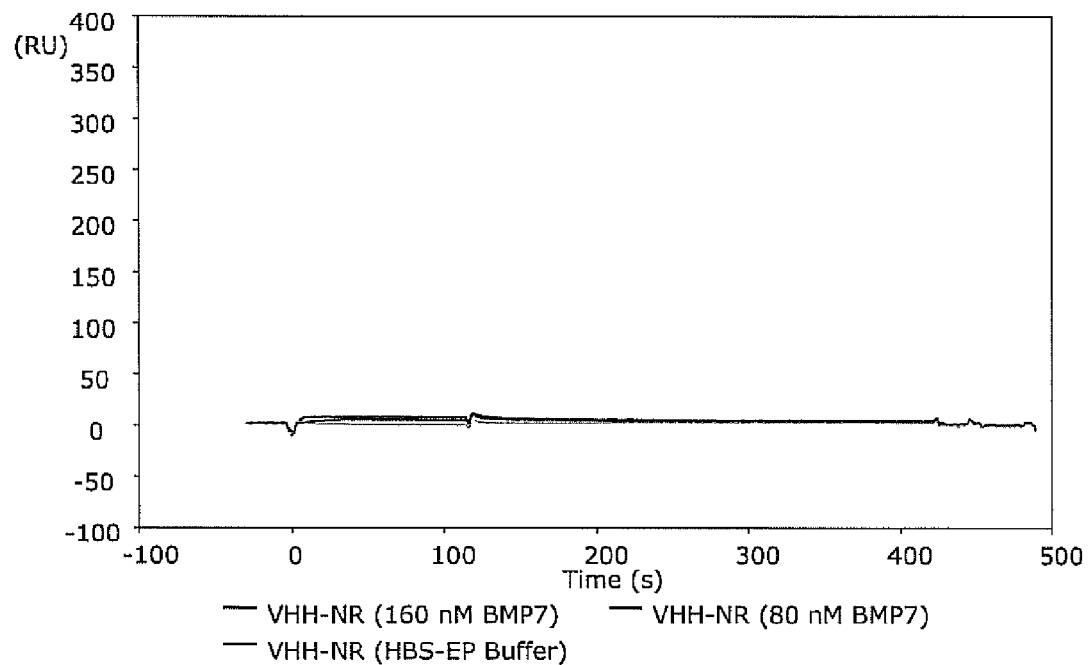
Figure 3:
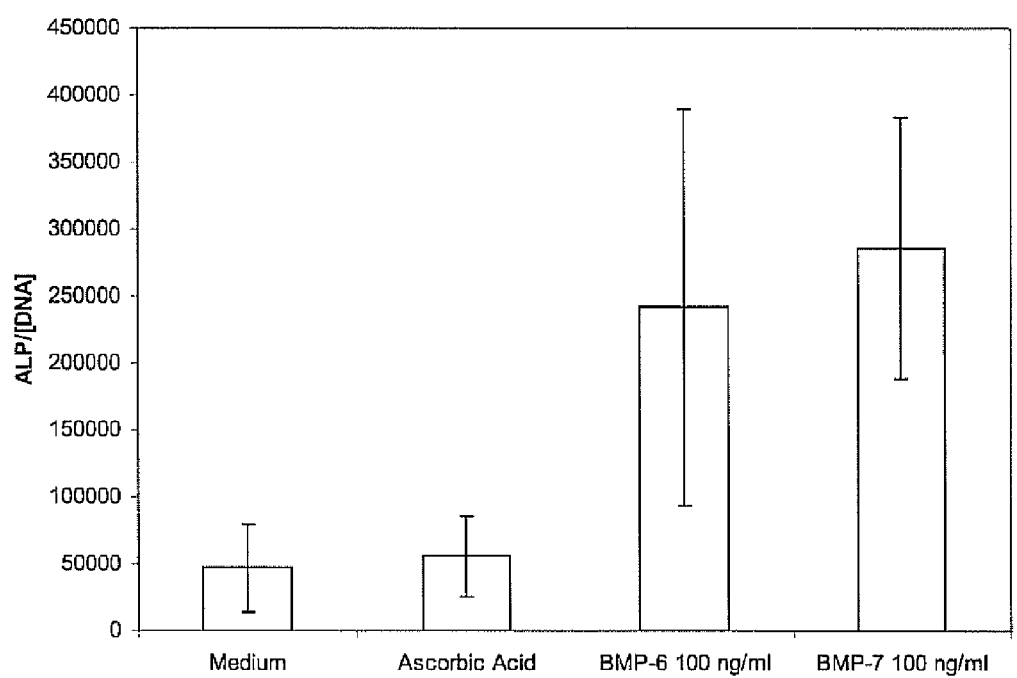
FIG. 3 shows the stimulation of Alkaline Phosphatase (ALP) in KS483 cells by BMP6. KS483 cells were stimulated with BMP6 (100 ng/ml) of BMP7 (100 ng/ml) in the presence of ascorbic acid. After 72 hours, ALP activity was measured. Both BMP6 and BMP7 induced ALP activity.
Figure 4A:
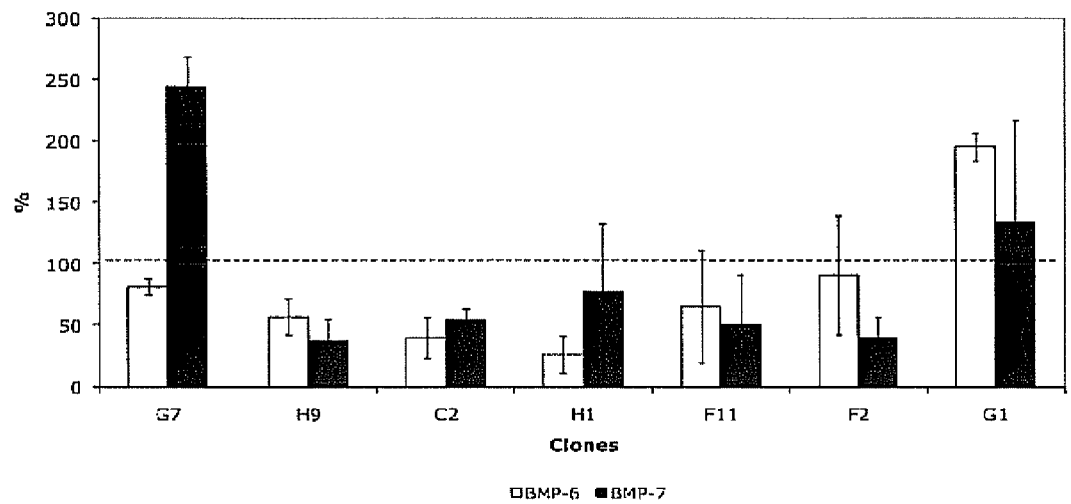
FIG. 4A shows the biological activity of selected VHHs against BMP6 and BMP7 in a bioassay. KS483 cells were stimulated with BMP6 or BMP7 in the presence of ascorbic acid and 1 µg of VHH clones 7-G7, 7-H9, 6-C2, 6-H1, 7-F11, 6-F2 and 6-G2. After 3 days ALP activity was measured and expressed relative to control cultures treated with either BMP6 or BMP7 in the absence of VHH. Values are expressed as % change relative to control which was set at 100%. Thus VHH 7-G7 potentiates the activity of BMP7 without affecting the activity of BMP6. VHH-7-H9 and VHH-6-C2 block the activity of BMP6 and BMP7. VHH-6-H1 only blocks the activity of BMP6 and VHH-6-F2 only blocks activity of BMP7. VHH-6-G1 potentiates the effects of BMP6 leaving BMP7 activity unaffected.
Figure 4B:
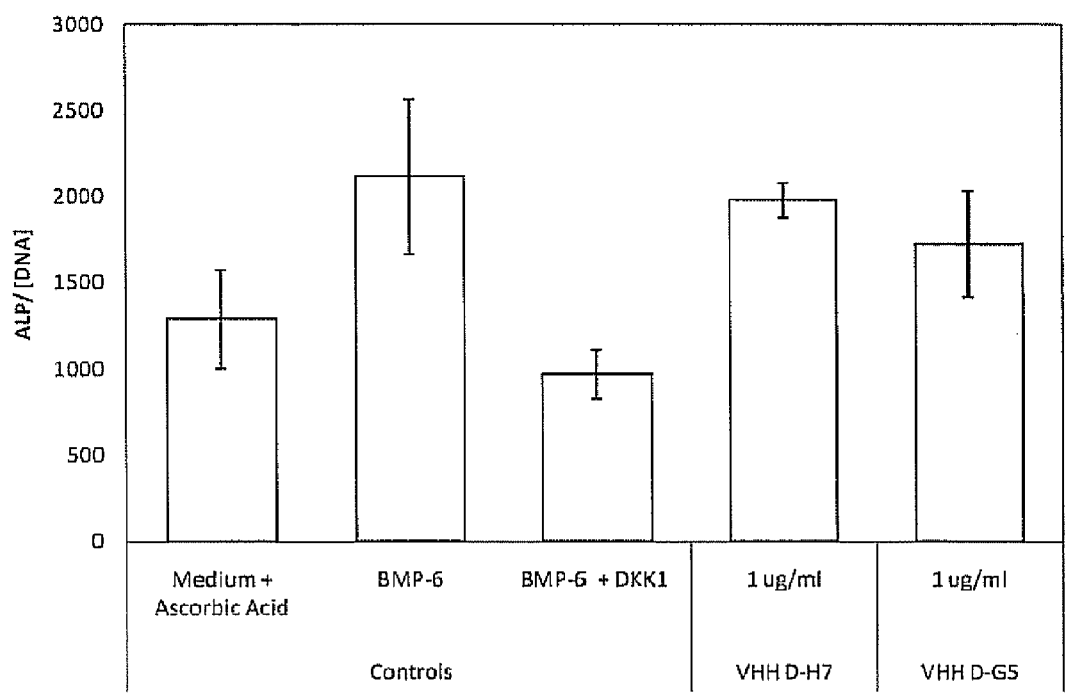
FIG. 4B shows the biological activity of selected VHHs against DKK1 in a bioassay. KS483 cells were stimulated with 100 ng BMP6 in the presence of ascorbic acid and 300 ng DKK1 and 1 µg of VHH clone D-H7 or D-G5. After 3 days ALP activity was measured and expressed as relative enzyme activity corrected for DNA. As expected BMP6 stimulates ALP activity, which was inhibited by DKK1. Co-incubation with VHH which binds to DKK1 according to the invention reverses DKK1 mediated inhibition of BMP6 induced ALP activity demonstrating effective binding and neutralization of DKK1 by said VHH.
Figure 5:
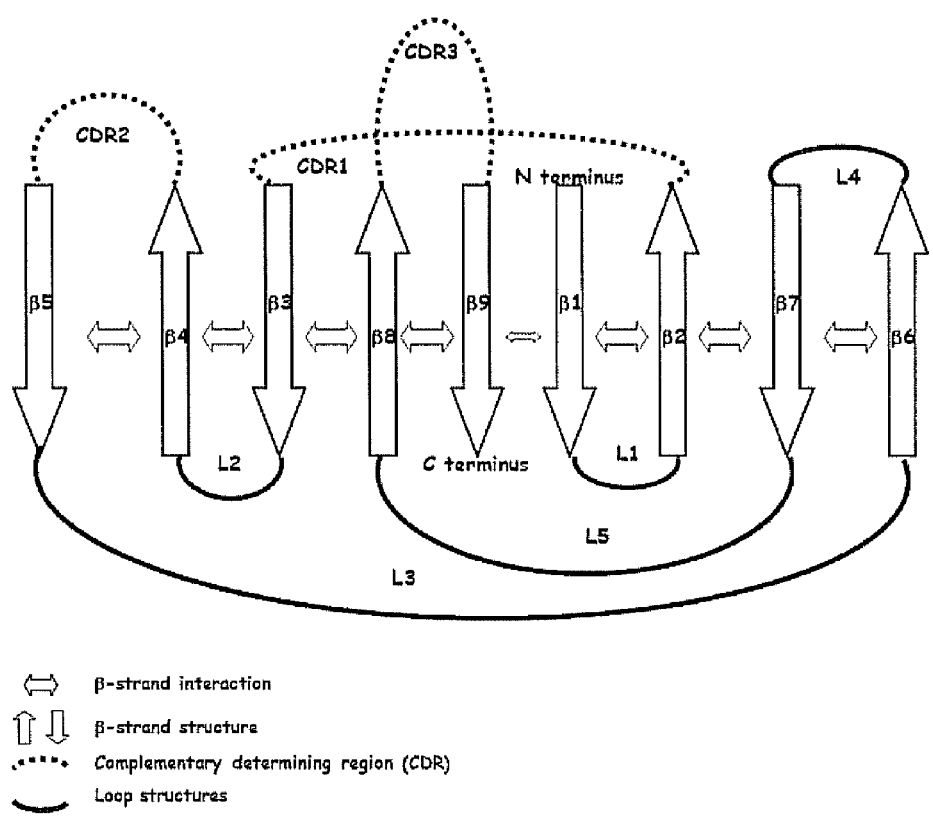
FIG. 5 shows a structural model of llama VHH. VHH is organized in 9 anti-parallel β-stands connected with loops. Three of these loops form the complementary determining regions (CDR1, CDR2 and CDR3). Loops 1, 2, 3 and 5 are located away from the CDRs and are suited for the introduction of glycosylation sites and incorporation of glycosyl groups without interference with binding of the VHH to its antigen. Loop 4 is located close to the CDRs and its manipulation may affect the binding of the VHH to its antigen.

The term 'VHH' refers to the single heavy chain variable domain antibodies devoid of light chains. Preferably a VHH is an antibody of the type that can be found in Camelidae or cartilaginous fish which are naturally devoid of light chains or to a synthetic and non immunized VHH which can be constructed accordingly. Each heavy chain comprises a variable region encoded by V-, D- and J exons. Said VHH may be a natural VHH antibody, preferably a Camelid antibody, or a recombinant protein comprising a heavy chain variable domain.

A 'V exon' in the context of the present invention describes a naturally occurring V coding sequence such as those found in Camelids. VHH exons may be derived from naturally occurring sources or they may be synthesised using methods familiar to those skilled in the art and described herein.

Likewise in the context of the present invention the terms 'a D exon' and 'a J exon' include naturally occurring sequences of D and J exons which are found in Camelids or other species of mammals. D and J exons may be derived from naturally occurring sources or they may be synthesised using methods familiar to those skilled in the art and described As further described herein, the amino acid sequence and structure of a VHH can be considered—without however being limited thereto—to be comprised of four framework regions or 'FR' s', which are referred to in the art and herein as 'Framework region 1' or 'FR1'; as 'Framework region 2' or 'FR2'; as 'Framework region 3' or 'FR3'; and as 'Framework region 4' or 'FR4', respectively; which framework regions are interrupted by three complementary determining regions or 'CDR' s', which are referred to in the art as 'Complementarity Determining Region 1' or 'CDR1'; as 'Complementarity Determining Region 2' or 'CDR2'; and as 'Complementarity Determining Region 3' or 'CDR3', respectively;

The term 'CDR' refers to the complementary determining region of the antibody structure.

The term 'framework region' is used herein to refer to the nucleic acid sequence regions of an antibody molecule that encode the structural elements of the molecule.

As also further described herein, the total number of amino acid residues in a VHH is typically in the region of 110-120, is preferably 112-115, and is most preferably 113. In another embodiment, said VHH according to the invention is preferably longer than 75, 80, 85, 90 amino acids. In another embodiment, said VHH is preferably not longer than 500, 450, 400, 350, 300, 250, 200, 150, 140, 130 or 120 amino acids. The amino acid residues of a VHH are numbered according to the general numbering for VH domains given by Lutje Hulsik, (Ph.D. thesis, Utrecht University, 2009).

The term 'binding' as used herein in the context of binding between a VHH and a target, refers to the process of a non-covalent interaction between molecules. Preferably, said binding takes place between said VHH and an epitope of the above mentioned targets. Preferably, said epitope comprises an amino acid sequence (such as a growth factor or an antagonist thereto that can bind to, that has affinity for and/or that has specificity for a specific epitope, antigen or protein (or for at least one part, fragment or epitope thereof) is said to be 'against' or 'directed against' said antigenic determinant, epitope, antigen or protein.

Preferably, said binding is specific. The terms 'specific' or 'specificity' or grammatical variations thereof refer to the number of different types of antigens or their epitopes to which a particular antigen-binding molecule (such as a VHH of the invention) molecule can bind. The specificity of an antigen-binding protein can be determined based on affinity.

The term 'treatment of a patient in need of an implant' as used herein refers to a treatment aiming to restore or to replace the function of a missing tissue and wherein the use of a VHH according to the invention is aimed at improving regeneration of a damaged tissue wherein said implant is implanted, ingrowth of surrounding tissue into said implant or attachment of said implant in the body of said patient.

With the term 'VHH which binds to a growth factor or an antagonist thereto' and the term 'VHH which binds to an implant' as used herein is meant that said VHH has an affinity for a growth factor or an antagonist thereto or to an implant which is better than the affinity of an irrelevant VHH for these targets. The affinity of a VHH for its target is a quality defined by a dissociation constant ($K_D$). Preferably said $K_D<10^{-5}$, preferably $<10^{-7}$, even more preferbly $<10^{-9}$ and most preferably $<10^{40}$. In another preferred embodiment, an affinity for a growth factor or an antagonist thereto is used with a dissociation constant in a range between 0.1-1001-nM. Methods of determining affinity are known in the art. Preferably, a method is used as described in Johnson et al. Journal of Molecular Biology 368 (2): 434-449

With the term 'VHH which binds to an implant' as used herein is further meant that said VHH has specificity and/or affinity for an epitope present on the surface of an implant or to an accessible (accessible for said VHH) epitope present in said implant. The term VHH which binds to an implant refers to a VHH which is functionalized. The term VHH and functionalized VHH as used herein in the context of a VHH which binds to an implant therefore can be used interchangeably.

The term 'tissue engineering' as used herein refers to a multidisciplinary approach aimed at repairing, reconstructing, regenerating or replacing lost or worn out tissue to restore its function.

The term 'implant' as used herein refers to a medical device, a biomaterial that is meant to at least partially be inserted into a mammal including humans for a period lasting at least long enough for tissue attachment to take place. Preferably an implant is meant to replace and act as a missing biological structure or to repair or support a damaged organ or tissue.

Preferred implants include devices that are placed over or within bones to hold a fracture reduction. Other preferred implants replace a part or whole of a defunct joint. Other preferred implants are placed within or outside the body. Other preferred implants include dental implants. Preferably, said implant comprises demineralised bone. Preferably said implant comprises a scaffold.

The term 'scaffold' refers to a material upon which a cell or a functionalized VHH can attach in a two- or three-dimensional configuration. The term encompasses artificial constructs known in the art as well a basic homogeneous composition to which cells can attach. In an aspect the scaffold itself is biocompatible, or coated with a material that makes the scaffold biocompatible. Scaffolds typically serve at least one of the following purposes:

Allow cell attachment and migration

Deliver and retain cells and biochemical factors

Enable diffusion of vital cell nutrients and expressed products

Exert certain mechanical and biological influences to modify the behaviour of the cell phase The scaffold typically creates the optimal microenvironment in which the various cell types can mature into a functional tissue. Maturation of the implant can occur in vitro or in vivo after implantation of the scaffold at the desired location in the body. The integration/interaction of these elements leads to the creation of new tissues.

The term 'biomaterial' as used herein refers to a natural or synthetic material used to replace part of a living system or to function in living tissue. Preferred synthetic biomaterials include metals, glasses, ceramics and polymers. Preferred polymers are of a natural origin, preferably collagen gels, chitosan, dextran, hyaluronic acid, heparin, heparan and starch or combinations of these materials. In another preferred embodiment, said polymers are of a synthetic orgin, preferably polyactive, poly lactic acid (PLA), a polyalkyleneoxide-polyalkyle-terephtalate block copolymer, (preferably polyethylene oxide-polybutylene terephtalate block copolymers), poly-L-lactic acid (PLLA), polyglycolic lactic acid (PGLA), polyglycolic acid (PGA), poly(amido amine)s, poly(caprolactone), polyethylene; a gel based on alginate, a Poly-N-isopropylacrylamid gel or copolymers of polyethylene glycol terephthalte and polybutylene terephthalate (PEG-PBT, or Polyactive®). Preferably said biomaterials are biocompatible. Biocompatible in this context means that a material does not elicit a pathological response of the body against said biomaterial or that said material is harmful to the patient. More preferably, said implant comprises a human cell membrane and/or and a non-natural or natural polymer. In another preferred embodiment, said implant comprises a calcium phosphate coating, a membrane of a synthetic polymer or an electrospun fiber.

The term 'patient' as used herein refers to a mammalian animal, preferably a human. The term 'patient in need of an implant' refers to a patient who has a missing tissue, which is replaced by an implant.

The term 'growth factor' as used herein refers to a molecule that elicits a biological response to improve tissue regeneration, tissue growth and organ function. Preferred growth factors are morphogens. The term 'morphogen' as used herein refers to a substance governing the pattern of tissue development and, preferably, the positions of the various specialized cell types within a tissue. Preferably, it spreads from a localized source and forms a concentration gradient across a developing tissue.

In preferred embodiments, a morphogen is a signaling molecule that acts directly on cells (preferably not through serial induction) to produce specific cellular responses dependent on morphogen concentration. Preferred morphogens include: a Decapentaplegic/Transforming growth factor beta (TGFbeta), Hedgehog/Sonic Hedgehog, Wingless/Wnt, an Epidermal growth factor (EGF), a Bone Morphogenic Protein (BMPs), and a Fibroblast growth factor (FGF). Preferably, said FGF comprises FGF2, KFG and FGF18. Preferrably, said BMP comprises BMP2, BMP4, BMP6 and BMP7. Preferred TGFbeta's include TGFbeta1 and TGFbeta3. In some preferred embodiments, said growth factor comprises a protein of the extracellular matrix.

The term 'growth factor antagonist' as used herein refers to secreted growth factor antagonists (BMP antagonists (noggin, gremlin), Wnt-antagonists (Dkk1, FrzB) and dual antagonists of both BMP and Wnt (Cerberus, Sclerostin).

The term 'antagonist to a growth factor' as used herein refers to a molecule which acts against and blocks an action of said growth factor.

The term 'dual antagonist' as used herein refers to a molecule which acts as an antagonist against two growth factors.

The term 'fusion protein' as used herein refers to proteins created through the joining of two or more genes which originally coded for separate proteins.

The term 'protein complex' as used herein refers to a group of two or more proteins joined by a non-covalent bond.

The term 'unnatural amino acid' as used herein refers to an amino acid not encountered in a living organism. The natural amino acids are the L isomers of Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Serine, Tyrosine, Arginine and Histidine. Preferably, said unnatural amino acid comprises a chemically modified Tyrosine or Lysine. Preferably said modified Tyrosine or Lysine comprises an azide or alkyn Group. Highly preferred unnatural amino acids comprise Tyr-alkyn, Tyr-azide, Lys-alkyn or Lys-azide.

As used herein, the term 'antibody' refers to an immunoglobulin which may be derived from natural sources or synthetically produced, in whole or in part. The terms 'antibody' and 'immunoglobulin' are used synonymously throughout the specification unless indicated otherwise.

An 'antibody fragment' is a portion of a whole antibody which retains the ability to exhibit antigen binding activity.

The term 'library' refers to a collection of nucleic acid sequences encoding VHHs. Preferably, said nucleic acid sequences encoding VHHs are cloned in a phagemid or phage or yeast.

The term 'non immunized library' refers to a collection of nucleic acid sequences encoding the naturally occurring VHH repertoire from a non-immunised source.

The term 'synthetic library' refers to a collection of nucleic acid sequences herein referred to as synthetic nucleic acid sequences, encoding single heavy chain antibodies or fragments thereof in which all CDR regions have undergone some form of rearrangement.

The term 'semi-synthetic library' refers to a collection of nucleic acid sequences encoding single heavy chain antibodies or fragments thereof in which at least one CDR region retains natural variability and at least one CDR region has undergone some form of controlled rearrangement. Preferably in the semi-synthetic library the CDR to be randomised or mutagenised is the CDR-3.

The term 'micro contact printing' as used herein refers to a printing technique which uses the relief pattern on a predesigned stamp to form patterns of a solution comprising the VHH, fusion protein or protein complex according to the invention on the surface of a implant substrate through contact.

VHH which Binds to a Growth Factor or an Antagonist.

The present invention relates to a specific class of antibodies, namely VHH antibodies for improving the regeneration of an implant. VHHs according to the invention bind growth factors or antagonists to a growth factor and in this way act as a reservoir of biological active factors that can be presented to cells. An advantage is that the integration of a VHH which binds to a growth factor or a growth factor antagonist improves cell attachment to or growth of cells in the implants or of the surrounding tissue or it accelerates differentiation and migration of relevant cells in the implant or in the surrounding tissue and said use increases the successful regeneration, reconstruction and replacement of lost and worn out tissues. Without wishing to be bound by theory, it is believed that as a result of binding between said VHH and said growth factor or said antagonist, the balance between factors that stimulate and factors that inhibit cell proliferation, cell differentiation, cell maturation, cell death and the formation of a functional organ cell growth is altered such that a better regeneration is achieved.

The integration of a functionalized VHH in appropriate architectural biomaterials is a powerful strategy to manipulate cell attachment, growth, differentiation and migration, and to increase the successful regeneration, reconstruction and replacement of lost and worn out tissues.

These VHHs serve as a powerful tool to improve the regenerative capacity of an implant. VHH can improve the structure of an implant by the incorporation of bioactive factors such as growth factors or growth factor antagonists which are ideally released in a time and space specific manner to improve tissue formation. More in particular, the functionalization of the VHHs allows them to control the presence of growth factors and/or growth factor antagonists in time and space. Scaffolds play a critical role in tissue engineering: they provide initial support to the developing tissue and create an optimal microenvironment in which undifferentiated stem cells or tissue progenitor cells or tissue specific cells can reconstitute a functional tissue unit.

Proper incorporation of the VHHs in these scaffolds requires the introduction of modifications that allow the positioning and attachment of the VHHs to the scaffold material without interfering with its biological activity, i.e. the binding of a respective growth factor or growth factor antagonist. The present invention describes methods for the introduction of such modifications creating functionalized VHHs. It is contemplated that conventional antibodies may also be functionalized for use for the preparation of a medicament for the treatment of a patient in need of an implant.

The present invention therefore provides a VHH which binds to a growth factor or an antagonist thereto. Said VHH is preferably used for the preparation of a medicament for the treatment of a patient in need of an implant.

Said growth factor or said antagonist thereto may be derived from any vertebrate species. Preferably, said species is human.

Spatial Organisation of the VHHs on the Materials

VHHs according to the invention can up-regulate the concentration of growth factors in the area where cells have to be enriched and/or have to proliferate. This is achieved by the presence VHHs binding these growth factors in that area, either as free VHHs or preferably as immobilized VHHs. To down regulate the concentration of antagonists of cell proliferation or differentiation a different approach has to be followed. In that case the VHHs binding these antagonists should be present in the vicinity of the area of interest, but not in that area itself. Such a spatial separation can be achieved using microcontact printing of VHHs using predesigned stamps. These stamps can be used to introduce micropatterns of different VHHs on a material surface relevant for tissue engineering and implantation in patients, for example using the methodology as described in Thery and Piel, Cold Spring Harb. Protoc. 2009(7) or techniques alike for introducing micro- or nanopatterns of proteins on a surface.

Methods to Obtain VHHs

Said VHH according to the invention may be derived from any immunoglobulin naturally devoid of light chains, such that the antigen-binding capacity and specificity is located exclusively in the heavy chain variable domain.

Preferably, the heavy chain variable domains may be obtained from camelids (as described in WO 94/4678), especially Lamas (for example Lama Glama, Lama Vicugia or Lama Paccos) or from Camelus (for example Camelus dromedarius or Camelus bactrionus). In another embodiment, said VHH is obtained from a cartilaginous fish.

In a preferred embodiment, said library is an immunized library. In another preferred embodiment said library is a non-immunized library. In preferred embodiments, said VHHs are obtained by immunization of a camelid or cartilaginous fish, with said growth factor or an antagonist thereto and subsequently isolating said protein.

In another preferred embodiment, said VHHs are obtained using antibody producing eukaryotic cells, preferably mammalian cells or yeasts, most preferably *Saccharomyces cerevisiae* or *Pichia pastoris*. Preferred cells comprise isolated B cells from sources of lymphoid cells or cell lines derived from B cells. Suitable sources include lymphoid cells preferably from peripheral blood lymphocytes, bone marrow cells and spleen cells. Methods for producing VHHs using B cells or cell lines are well known in the art. Advantageously hybridomas may be used for generating monoclonal antibodies. Techniques will be familiar to those skilled in the art.

In another preferred embodiment, said VHHs are produced using eukaryotic or prokaryotic production systems. Preferred production systems comprise *E. coli*, yeast, or filamentous fungi.

In a preferred embodiment, said production system is a eukaryotic production system. An advantage thereof is that folding of the protein results in proteins that are more suitable for treating a mammal. Moreover, eukarotic cells often carry out desirable post translational modifications like mammalian cell do.

Production of VHH in filamentous fungi is preferably performed as described by (Joosten et al., J Biotechnol 120:347-359 (2005).

A preferred method for producing VHHs in *Saccharomyces cerevisiae* is according to the method as described by Frenken et al. (2000) J Biotechnol 78:11-21. Another preferred method of VHH production is by yeast expression host *Pichia pastoris* as described by Rahbarizadeh et al. (2006) J Mol Immunol 43:426-435.

In a preferred embodiment, said VHH comprises a potential N-linked glycosylation site. An advantage thereof is that this causes an increase in the production levels in yeast. Another advantage is that glycosylation sites can be advantageously used to bind a VHH to an implant through chemical cross linking with carbohydrates in the implant or can be used as an anchor of VHH in a dense polymer network as observed in hydrogels. In a preferred embodiment, said VHH comprises a glycosyl group attached at one of the VHH's short loops present at the opposite site of the antigen binding domain of the VHH. An advantage of the presence of a glycosyl group is that this results in a slower release of the VHH when it is incorporated in a transplant.

Alternatively, a naturally occurring VHH domain against said growth factors or antagonists or said implant can be obtained from non-immunized libraries of Camelid VHH sequences, for example by screening such a library against the antigen or at least one part, fragment, antigenic determinant or epitope thereof using one or more screening techniques known per se. Such libraries and techniques are for example described in WO99/37681, WO 01/90190, WO 03/025020 and WO 03/035694. Alternatively, improved synthetic or semi-synthetic libraries derived from non-immune VHH libraries may be used, such as VHH libraries obtained from naïve VHH libraries by techniques such as random mutagenesis and/or CDR shuffling, as for example described in WO 00/43507.

Yet another technique for obtaining VHH sequences directed against said growth factor or antagonists therefore or said implant involves suitably immunizing a transgenic mammal that is capable of expressing heavy chain antibodies (i.e. so as to raise an immune response and/or heavy chain antibodies directed against), obtaining a suitable sample from said transgenic mammal (such as a blood sample, or sample of B-cells), and then generating VHH sequences directed against starting from said sample, using any suitable technique known per se. For example, for this purpose, the heavy chain antibody-expressing mice and the further methods and techniques described in WO 02/085945 and in WO 04/049794 can be used.

In another preferred embodiment, said VHHs may conveniently be prepared by a method which does not require the donor previously to have been immunised with the target antigen. Preferably, said method comprises the use of a non immunized library as described in EP1934611 A2.

In a preferred embodiment, the framework regions of the VHH domains may conveniently be derived from a non immunized library of VHH domains. This allows the natural variability in these sequence segments to be reflected in the expression library. Such methods are well known in the art and described for instance in EP1934611 A2.

A particularly preferred class of VHH of the invention comprises VHH with an amino acid sequence that corresponds to the amino acid sequence of a naturally occurring VHH domain, but that has been 'humanized' as explained in EP1934611 A2.

Other suitable ways and techniques for obtaining the VHH of the invention and/or nucleic acids encoding the same, starting from naturally occurring VHH sequences, will be clear to the skilled person, and may for example comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a VHH of the invention or a nucleotide sequence or nucleic acid encoding the same.

The VHH of the invention may be generated in any manner known per se, which will be clear to the skilled person. Generally, this will involve at least one step of selecting VHH which binds to a growth factor or an antagonist thereto or which binds to an implant, and preferably also at least one further step of selecting (i.e. from the VHH thus selected) VHH that are capable of immunoprecipitating a cognate antigen and preferably a further step of selecting a VHH that is capable of stimulating growth of a cell and/or of improving attachment of an implant in a host. The first selection step can be performed in any manner known per se for selecting VHH or antibodies against a desired antigen, such as the techniques reviewed by Hoogenboom, Nature Biotechnology, 23, 9, 1105-1116 (2005), the so-called SLAM technology (as for example described in EP 0 542 810). The subsequent step(s) can generally be performed using any suitable in vitro, cell-based or in vivo assay (depending on the specific growth factor or antagonist thereto or material of an implant) and suitable assays will be clear to the skilled person based on the disclosure herein.

Typically in selections starting with an immune library the number of phages is reduced from $10^7$ to $10^4$; whereas in selections starting with a non-immunized library the number of phages is reduced from about $10^9$ to $10^4$. The selection is based on binding of the phage, (or of a yeast in a yeast display) to the antigen of choice. In the subsequent steps, consisting of DNA finger printing of the selected VHH genes, production in a production system, preferably *E. coli*, and a lower eukaryote to evaluate the folding properties of the selected VHH in vivo, the number of positive phages is generally reduced from $10^4$ to $10^2$. The screening on in vivo folding properties of the selected VHHs selects for their functionality in- and outside cells. It has been found that there is a strong correlation between correct folding in vivo and the refolding of VHHs in vitro. After this screening typically 20-50 VHHs remain suitable candidates and from these candidate VHHs the nucleotide sequences are determined, which also provide the amino acid sequences. Preferably, the thus screened positive VHHs are then tested for desired property, including affinity and/or specificity for its target and/or its ability to immunoprecipitate cognate antigens and preferably also for its ability stimulate growth of cells and even more preferably to improve attachment of an implant in a host. The final screening process typically reduces the number of candidate VHHs to less than 20% of the VHHs for which the amino acid sequence have been determined.

In a preferred method for VHH-selection from libraries, VHH selection comprises phage display technology as described in EP1934611 A2.

Growth Factor Antagonists

In a preferred embodiment, said antagonist is a BMP antagonist, preferably Noggin, Gremlin, a Wnt-antagonist, preferably Dkk1, FrzB, a dual antagonist of BMP and Wnt, preferably Cerberus or Sclerostin. In a highly preferred embodiment, said VHH which binds to sclerostin comprises at least one of the sequences as listed in Table 1

TABLE 1

| VHHs that bind to sclerostin | |
| --- | --- |
| Sost-VHHs | Sequence |
| VHH-S-A6-1 | EVQLVESGGGLVQAGGSLRLSCAASGRTFSRDVMGWFRQAPGKVREVVG SITWSGGSTYYADSVKGRFTISRDNAKNTMYLQMNSLKPEDTGVYYCAVA ELGSTYNDWGQGTQVTVSS (SEQ ID NO: 3) |
| VHH-S-D7 | EVQLVESGGGLVQAGGSLRLSCAGSGFAFDDYAIGWFRQGPGKEREGVA CISGKDGSTYYTDSVKARFTISSENAKNTAYLQMNNLKPEDTGRYFCVAD PDGGCDSFTGATMMGYWARGTQVTVSS (SEQ ID NO: 4) |
| VHH-S-H12 | EVQLVESGGGLVQAGGSLRLSCAASGRTFSRDVMGWFRQAPGKVREVVG SIKWSDANTYYADSVKGRFTISRDNAKNTMYLQMNSLKPEDTGVYYCAA AIIGGTYNDWGQGTQVTVSS (SEQ ID NO: 5) |
| VHH-S-C3 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 6) |
| VHH-S-C10 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 7) |
| VHH-S-B1 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 8) |
| VHH-S-F9 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 9) |
| VHH-S-G1 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 10) |
| VHH-S-G5 | EVQLVESGGGLVQAGGSLRLSCAASGSIFSILTMGWYRQAPGRQREMVAT ITTSGGLTNYTDSVKGRFSISRDNNKNTVYLQMNSLKPEDTAVYYCNAAM VGGGVGLGRRPSFSYWGQGTQVTVSS (SEQ ID NO: 11) |
| VHH-S-E11 | EVQLVESGGGLVQSGGSLRLSCAASGRTFSTDFMGWFRQAPGKEREFVAT IDWRSGSAGYADSVQGRFTISKDNAKNTVYLQMMNLQPGDTGVYYCAAQ MIGASSYGYWGRGTQVTVSS (SEQ ID NO: 12) |
| VHH-S-D7 | EVQLVESGGGLVQAGGSLRLSCAGSGFAFDDYAIGWFRQGPGKEREGVA CISGKDGSTYYTDSVKARFTISSENAKNTAYLQMNNLKPEDTGRYFCVAD PDGGCDSFTGATMMGYWAQGTQVTVSS (SEQ ID NO: 13) |
| VHH-S-H12 | EVQLVESGGGLVQAGGSLRLSCAASGRTFSRDVMGWFRQAPGKVREEVG SIKWSDANTYYADSVKGRFTISRDNAKNTMYLQMNSLKPEDTGVYYCAA AIIGGTYNDWGQGTQVTVSS (SEQ ID NO: 14) |

TABLE 1-continued

VHHs that bind to sclerostin

| Sost-VHHs | Sequence |
|---|---|
| VHH-S-E11 | EVQLVESGGGLVQSGGSLRLSCAASGRTFSTDFMGWFRQAPGKEREFVAT IDWRSGSAGYADSVQGRFTISKDNAKNTVYLQMNSLKPEDTGVYYCAAQ MIGASSYGYWGRGTQVTVSS (SEQ ID NO: 15) |
| VHH-S-A6-2 | EVQLVESGGGLVHAGGSLRLSCAASGFTFSSYAMSWVRQAPGKGPEWVS HINSGGGSTSYADSVKGRFTISRDNAKNTLYLQMNSLKPEDTAVYYCAKL REGADYSGSYYYLYEYDYWGQGTQVTVSS (SEQ ID NO: 16) |

In another preferred embodiment, said VHH which binds to BMP6 and/or BMP 7 comprises at least as one of the sequences as listed in Table 2:

TABLE 2

VHH that bind to BMPs

| BMP-VHHs | Sequence |
|---|---|
| VHH-6-A1 | EVQLVESGGGLVQAGGSLTLSCAASEIISSINAMGWYRQAPGKQRELVALI GSGGTTKYGDCAKGRFTISRDNAKNTVTLQMNSLKPEDTAVYYCYVHDYD HKAWGQGTQVTVSS (SEQ ID NO: 17) |
| VHH-6-A4 | EVQLVESGGGLVQAGGSLTLSCAASEIISSINAMGWYRQAPGKQRELVALI GSGGTTKYGDCAKGRFTISRDNAKNTVTLQMNSLKPEDTAVYYCYVHDYD HKAWGQGTQVTVSS (SEQ ID NO: 18) |
| VHH-6-C1 | EVQLVESGGGLVQAGGSLRLSCAASGRTFSSYGMWFRQAPGKERDFVAA VSRSGGNTYYTASVKGRFTISRDNAKNTMYLQMNSLKPEDTAVYYCAAGR WESGSRLGSTWYGERTYDYWGQGTQVTVSS (SEQ ID NO: 19) |
| VHH-6-C2 | EVQLVESGGGLVQVGGSLRLSCAASGRTSSMYSMGWFRQAPGKEREFVAA IGWRFGEKYYTNSVKGRFTISRDGAENTNTVYLQMNSLKPDDTAVYYCAA DPDDASQYYSDWMKGYGMDYWGKGTLVTVSS (SEQ ID NO: 20) |
| VHH-6-D6 | EVQLVESGGGLVQAGGSLRLSCAASGRTFSSYGMGWFRQAPGKERDFVAA VSKSGGSTYYTASVKGRFTVSRDNAKNTVYLQMNSLKPEDTAVYYCAAGR WESGSRPGSTWYGERTYDYWGQGTQVTVSS (SEQ ID NO: 21) |
| VHH-6-G1 | EVQLVESGGGLVQAGGSLRLSCAASRRISGIYAMGWYRQSPGKERELVAAI TTSDHTNYADFVKGRFTISRDKVNNTVYLEMNTLKPEDTAVYYCKQSAWG RNDYWGQGTRVTVSS (SEQ ID NO: 22) |
| VHH-6-G4 | EVQLVESGGGLVQAGGSLKLSCAASRRISGIYAMGWYRQTPGKERELVAAI TTSDHTNYADFVKGRFTISRDKVNNTVYLEMNTLKPEDTAVYYCKQSAWG RNDYWGQGTRVTVSS (SEQ ID NO: 23) |
| VHH-6-F2 | EVQLVESGGGFVQAGGSLRLSCAASGSIFSINAMGWYRQAPGKQRELVAAI TSGGSTNYADSVKGRFTISRDNAKNTLYLQMNSLKPEDTAVYYCSAVTILL TSGGWGSGNDYWGQGTQVTVSS (SEQ ID NO: 24) |
| VHH-6-H6 | EVQLVESGGGLVQAGGSLRLSCAASGRTFSSYAMGWFRQAPGKERDFVAA ISWSGGSTYYTGSVKGRFNISRDNAKNTVYLQMNSLKPEDTAVYYCAGGP RSAYYDDYGYDYWGQGTQVTVSS (SEQ ID NO: 25) |
| VHH-6-H1 | EVQLVESGGGLVQAGGSLRLSCAASGSIFSIVSMGWYRQVPGKQRELVAAI TSAGSTNYGDSAKGRFTISRDNAKNTVYLQMNSLKPEDTAVYYCNSYGLG YPGDYGIDYWGKGTLVTVSS (SEQ ID NO: 26) |
| VHH-7-B8 | EVQLVESGGGLVRAGGSLRLSCAASGRTFSGYVAGWFRQAPGKEREFVAAI SWSGITYYGDSVKGRFTIARDNSKNGVYLQMNSLKPEDTAVYYCGAGKGY YKDYRGYDYWGQGTQVTVSS (SEQ ID NO: 27) |
| VHH-7-A11 | EVQLVESGGGSVQAGGSLRLSCAASRRISGIYAMGWYRQSPGKERELVAAI TTSDHTNYADFVKGRFTISRDKVNNTVYLEMNTLKPEDTAVYYCKQSAWG RNDYWGQGTRVTVSS (SEQ ID NO: 28) |
| VHH-7-F11 | EVQLVESGGGLVQAGGSLRLSCAASGRTFSGYVAGWFRQAPGKEREFVAA SSWSGITYYGDSVKGRFTISRDNAKNTVYLQMNSLKPEDTAVYYCGAGKG YYKDYRGYDYWGQGTQVTVSS (SEQ ID NO: 29) |

TABLE 2-continued

VHH that bind to BMPs

| BMP-VHHs | Sequence |
|---|---|
| VHH-7-H9 | EVQLVESGGGLVQAGGSLRLSCAASGSAFSINAMGWYRQGPGKQRTLVARI<br>TSGGSTNYADSVKGRFTISRDNAKNTVYLQMNSLKPEDTAVYYCYAVHSK<br>LSTTGWGTIGDYWGQGTQVTVSS (SEQ ID NO: 30) |
| VHH-7-G7 | EVQLVESGGGLVQAGGSLRLSCAASGFTFDDYIIGWFRQAPGKEREGISCIS<br>SSDGSTYYADSVTGRFTISSDNAKNTVYLQMNSLKPEDTAVYYCAAHAKW<br>PYGTYSFRRCRRASFDSWGQGTQVTVSS (SEQ ID NO: 31) |
| VHH-7-H11 | EVQLVESGGGLVQAGGSLRLSCAASGRTFSGYVAGWFRQAPGKEREFVVA<br>LSWSGITYYGDSVKGRFTISRDNGKNTVYLQMNSLKPEDTAVYYCGAGKG<br>YYKDYRGYDYWGQGTQVTVSS (SEQ ID NO: 32) |
| VHH-7-H12 | EVQLVESGGGLVQAGGSLRLSCAASGRTFSGYVAGWFRQAPGKEREFVAAI<br>SWSGITYAGDSVKGRFTISRDNAKNTVYLQMSSLKPEDTAVYYCGAGKGYY<br>KDYRGYEYWGQGTQVTVSS (SEQ ID NO: 33) |

In a preferred embodiment, said VHH which binds to DKK1 comprises at least as one of the sequence as listed in Table 3:

TABLE 3

VHH that bind to DKK1

| DKK1-VHHs | Sequence |
|---|---|
| VHH-D-B7 | EVQLVESGGGLVQAGGSLRLACAASGRTFSNYRMGWFRQAPGQEREFV<br>AAISGSGSFTYYADSVKGRSTISRDNAKNTVYLQMNSLKPEDTAVYYCG<br>AGVHLGAATSYTRYDFWGQGTQVTVSS (SEQ ID NO: 34) |
| VHH-D-C9 | EVQLVESGGGLVQPGGSLRLSCVVSGFTISNYGMSWVRQAPGKGPEWE<br>WVSAINSGGDSTRYADSVKGRFTISRDNAKNTLYLQMNSLKPEDAAVYF<br>CTREKTAYYCSGSGCYDPRYEFDYWGRGTQVTVSS (SEQ ID NO: 35) |
| VHH-D-D4 | EVQLVESGGGLVQAGDSLRLSCAASGRSISLYAMAWFRQAAGKEREFVA<br>AINWSGGSTRYADSVKGRFSISRDTAKNTVYLTMNSLKPEDTAVYYCAT<br>DSSTTVVFYSSSNSLRYWGQGTQVTVSS (SEQ ID NO: 36) |
| VHH-D-F6 | EVQLVESGGGLVQAGGSLRLSCAASGSTGAMAWFRQAPGKERDLVASIS<br>RSGVSTYYADSVKVRFTISRDNAKNTVFLQMNNLKPEDTGVYYCAAGPT<br>FRQSRATYTDWGQGTQVTVSS (SEQ ID NO: 37) |
| VHH-D-G5 | EVQLVESGGGLVQAGGSLRLSCAASGRALSRSPMAWFRQAPGKEREFV<br>VHWISGSTYYADSVKGRFTTSRDNAENTVYLQMNSLKPEDTAVYYCAAG<br>FAPDTPSIFTSPRTYYYWGQGTQVTVSS (SEQ ID NO: 38) |
| VHH-D-H7 | EVQLVESGGGLVQAGGSLRLSCAASGSTGAMAWFRQAPGKERDLVASIS<br>RSGVSTYYADSVKVRFTISRDNAKNTVFLQMNNLKPEDTGVYYCAAGPT<br>FRQSRATYTDWGQGTQVTVSS (SEQ ID NO: 39) |
| VHH-D-B12 | EVQLVESGGGLVQPGGSLRLSCAASGFTFSSYAMSWVRQAPGKGLEWV<br>SAINSGGGSTSYADSVKGRFTISRDNAKNTLYLQMNSLKPEDTAVYRCA<br>KYYEADPAKNEYDYWGQGTQVTVSS (SEQ ID NO: 40) |
| VHH-D-A7 | EVQLVESGGGLVQAGGSLRLSCAASGSIVTFNPMGWYRQAPGNQRELV<br>ASITSGGGANYVDSVKGRFTISVDSAKNTVYLQMNSLKPEDTAVYYCNA<br>DIFSSSRLSWDNYWGQGTQVTVSS (SEQ ID NO: 41) |

VHH Binding to an Implant

The invention further provides a VHH which binds to a biomaterial. These VHH can suitably be used as a linking protein to bind a biomolecule to a biomaterial. Said VHH which binds to a biomaterial is therefore very suitable for binding the VHH according to the invention to an implant.

The inventors have surprisingly found that it is possible to make VHH which bind to biomaterials. This is surprising, because biomaterials are selected for their biocompatibility which requires that they must be non-immunogenic. Raising conventional antibodies against biomaterials is therefore impossible. Despite this, the inventors have produced VHHs which bind with a biomaterial with a good affinity. Such VHHs can be produced using the methods to produce and select VHHs as described herein. In a preferred embodiment, said VHH comprises the amino acid sequence selected from the sequences as listed in Table 4, Table 5 and Table 6.

Fusion Proteins Comprising at Least Two VHHs

Further provided is a fusion protein comprising at least two VHHs, wherein at least one VHH is a VHH which binds to a growth factor and/or an antagonist thereto according to the invention and/or at least one VHH is a VHH which binds to an implant according to the invention. Herein, said fusion proteins are also referred to as "bivalent", "bihead" or "biparatopic VHHs". Fusion proteins comprising 3 VHHs are also referred to as "trivalent" or "trihead". The prefix "hetero" in conjunction with bihead or bivalent VHH as used herein, is used to indicate that said fusion protein comprises 2 different VHHs, whereas the prefix "homo" in this context is used to indicate that the VHHs in said fusion protein are the same. In a more preferred embodiment said first VHH binds to a first epitope and said second VHH binds to a second epitope of the same molecule present in said implant. In some preferred embodiments, said fusion protein is a multimer composed of polymerized monomers, wherein said monomers comprise said fusion protein or a VHH according to the invention. Said multimer is herein also referred to as "multivalent VHH". Preferably, said multimer comprises 4 monomers or less.

In a preferred embodiment, said fusion protein comprises a bivalent of at least two VHHs binding to said growth factor or said antagonist, preferably wherein said at least two VHHs have an affinity for the same epitope, and wherein one of said VHHs is functionalized (see FIG. 6b). An advantage thereof is that different VHHs according to the invention are linked together to broaden the range of growth factors that can be bind to said implant. In a preferred embodiment, said fusion protein further comprises a VHH which binds to said implant (FIG. 6d). An advantage thereof is that said VHH has an affinity for said implant. In a preferred embodiment of said fusion protein, said fusion protein comprises 2 VHHs binding to said implant (FIG. 6f). An advantage thereof is that the affinity for said implant is further increased.

In another preferred embodiment, said fusion protein comprises one VHH which binds to said growth factor or antagonist and one VHH which binds to said implant (FIG. 6c). An advantage thereof is that this fusion protein can be attached to an implant and has an affinity for a growth factor or antagonist. In a preferred embodiment, said fusion protein comprises two VHHs which bind to said implant (see FIG. 6e). An advantage thereof is that said fusion protein has an increased residence time in said implant.

In some preferred embodiments of the fusion proteins according to the invention, at least one functional group is added to said fusion protein to further increase the affinity for said implant.

By selecting VHHs with different affinities to said implant and by constructing biheads or monoheads of VHHs according to the invention, a skilled person is able to manipulate the residence time of the VHHs, and thus growth factor(s) or antagonist(s), on the implant according to the desired or the necessary time.

Said fusion protein may be formed by fusing VHHs, preferably VHHs according to the invention and preferably VHHs which are selected based on affinity for a growth factor, antagonist or implant using a non-immunized VHH library as known in the art and described herein, using any methods known in the art. For example, they may be fused by chemical cross-linking by reacting amino acid residues with an organic derivatising agent such as described by Blattler et al, Biochemistry 24, 1517-1524; EP294703.

Alternatively, the single domain antibody may be fused genetically at the DNA level i.e. a polynucleotide construct formed which encodes the complete polypeptide construct comprising one or more anti-target single domain antibodies. A method for producing bivalent or multivalent VHH polypeptide constructs is disclosed in PCT patent application WO 96/34103.

Another preferred way of preparing said fusion protein is via the genetic route by linking a VHH antibody coding sequences either directly or via a peptide linker. The linker may comprise several amino acids, e.g. up to 5, 10, 25, or even 100. In a preferred embodiment, the linker comprises the sequence GGGGS (SEQ ID NO:42) or 1-10 repeats of said sequence, For example, the C-terminal end of the VHH antibody may be linked to the N-terminal end of the next single domain antibody. This linking mode can be extended in order to link additional single domain antibodies for the construction and production of tri-, tetra-, etc. functional constructs According to one aspect of the present invention, said VHHs are linked to each other directly, without use of a linker. Contrary to joining bulky conventional antibodies where a linker sequence is needed to retain binding activity in the two subunits, polypeptides of the invention can be linked directly thereby avoiding potential problems of the linker sequence, such as antigenicity when administered to a human subject, instability of the linker sequence leading to dissociation of the subunits.

In a preferred embodiment, said fusion protein comprises genetic fusions of two or three VHHs that either recognize different antigens or the same repeating antigen to increase functional affinity. Methods for preparing said fusion proteins are described in EP1934611 A2.

Protein Complex

Further provided is the use of a protein complex comprising a VHH which binds to a growth factor or an antagonist thereto according to the invention and said growth factor or said antagonist. Said protein complexes can suitably be used in the preparation of said implants.

Improvements of the CDRs of the Selected VHHs.

Maturation of antibodies from their V(D)J gene is not a straight upwards process, but rather a road with much ups and downs. Maturations are certainly not restricted to CDRs, also nucleotide sequences that encode the frame works are often mutated. This can result in many mutations in the frame work that do not contribute to improved binding capacity of the VHHs against their cognate antigens neither to better physical properties of the VHHs.

We have a data base of nearly 2000 nucleotide sequences and the amino acids derived from these sequences encoding VHHs and we determined which amino acids are key residues for the proper folding or refolding of VHHs, and which amino acid have the lowest entropy variability [E.V.] and therefore contribute to the stability of the molecule (Lutje Hulsik, Ph. D. Thesis 2009). Moreover we have determined the sequence of the germ line V-, D- and J-genes of Lama glama genome and therefore, we are able to reconstitute the sequence of the selected VHHs from the V(D)J combinations in details, and consequently predict which mutations in the frame work may reduce its overall performance.

In a preferred embodiment, CDRs of the selected VHHs are improved to achieve a higher affinity. Methods to improve CDRs are known to the skilled person and are described in EP1934611 A2 or (Rajpal et al. Proceedings of the National Academy of Science. 102-24; 8466-8471 (2005)).

Comparison of the germ line V(D)J genes combinations and the matured VHHs show at nucleotide and amino acids level exactly the maturation of the CDRs. This in combination with our large data base and information at atomic level of the interaction between antigens and their cognate VHHs provided substantial information which amino acids of CDRs may play important roles in the interactions between the selected VHHs and sclerostin, BMP6, BMP7 or Dkk1, respectively. Using this information we carried out an alanine scan of the CDRs (Cunningham and Wells. Science.244-4908; 1081-1085 (1989)). Subsequently we used a semi rational approach (Rajpal et al, Protein Sci. 7, 9-1868-1874, 1998) to design changes of the amino acid sequences of CDRs. In attempts to improve the binding affinity and specificity of the selected VHHs towards cognate antigens, we will carry an Ala-scan of the CDRs. Based on the information gained from the reconstitution of the maturation process from the germ line V(D)J genes, and based on the knowledge gained from the interaction between VHHs and their antigens already available in the large data base, we will design changes of the amino acid sequences of the CDRs to improve the binding properties of the VHHs to their cognate antigens.

Binding of a Functional Group to a VHH

Further provided is a VHH according to the invention which is functionalized. VHHs according to the invention can be functionalized to bind to said implant, more preferably the scaffolds of said implant. Functionalization is preferably achieved by adding a functional group to the VHH (See FIG. 6a). Alternatively, functionalization may be achieved by inserting the nucleic acid sequence encoding a peptide sequence which has affinity for an implant into the nucleic acid encoding the VHH. Preferably, said peptide sequence comprises the amino acid sequence selected from the group consisting of the amino acid sequences VTKHLNQISQSY (AP1) (SEQ ID NO:1) and APWHLSSQYSRT (AP2) (SEQ ID NO:2), which bind to implants containing hydroxyapatite. Preferably said peptide sequence is grafted into CDR3 by replacing the original CDR3 sequence.

In a preferred embodiment, said at least one functional group comprises a peptide having affinity to said implant. Preferably, said at least one functional group comprises at least one cysteine, or at least one methionine. These amino acids can be coupled to ligands present in said implant through disulfide bonds. In another preferred embodiment, said functional group comprises an unnatural amino acid. Preferably, said unnatural amino acid comprises a reactive group, such as alkyn or azide groups, which react with high efficiency and specificity to form covalent linkage with compounds containing azide or alkyn groups, respectively, as described in Zhang et al. Biochemistry 42-22. 6735-6746 (2003).

In another preferred embodiment, said at least one VHH has a glycosylation sequence present or introduced in any of the loops 1, 2, 3 and 5, preferably loops 2, 3 and 5, most preferably loops 2 and 3.

In one embodiment, said functional group comprises a His6 tag. An advantage thereof is that it enables coupling of VHHs to metal surfaces, in particular a Nickel surface.

In a preferred embodiment, said functional group comprises a peptide derived from a CDR of the VHH which binds to an implant. Preferably, said CDR comprises the CDR3 of VHH. An advantage thereof is that said VHH comprising said functional targets said VHH to said implant. Preferably, the peptide is integrated at the place normally occupied by CDR3. An example of grafting a peptide sequence on the VHH scaffold is given in Table 8.

The VHH scaffold was chosen for its stability and high secretion capacity. The AP1 sequence was grafted into CDR3 by replacing the original CDR3 sequence. The resulting sequence is depicted in Table 8.

In another preferred embodiment, said VHHs are chemically linked to said implant in a non-directed manner by using NHS(N-hydrosuccinimde chemistry). An advantage thereof is that all amine groups in the VHH may be involved in the binding, resulting in a better binding.

The invention further provides for the use of a VHH according to the invention, a fusion protein according to the invention or a protein complex according to the invention or a VHH which binds to an implant according to the invention for functionally mimic a biologically active agent. Preferably said biologically active agent comprises a protein of the extracellular matrix (ECM) or another secreted protein such as a growth factor, a cytokine or a morphogen, thereby enhancing tissue growth, generation or functioning.

Further provided is the use of a VHH according to the invention, a fusion protein according to the invention or a protein complex according to the invention or a VHH which binds to an implant according to the invention as a tissue engineering aid to load a biological tissue or an implant with a growth factor that modulates, in particular stimulates, formation of new biological tissue or growth of existing tissue, in vivo or in vitro.

A VHH can be used as a tissue engineering aid to load a biological tissue or an implantable material with a biologically active agent that contributes to a modification of existing biological tissue. Such agent may then gradually, or even in a controlled manner, be released and exert its stimulating effect. A VHH can be used as a tissue engineering aid to locally sequester a biologically active agent. The VHH may thus inactivate a biologically active agent that has an inhibitory effect on the tissue repair. A VHH may also be used to attract a biologically active agent with a beneficial effect from the body fluid to an implanted biomaterial, thereby locally causing an increase in the concentration of the agent. For example, a VHH with BMP binding properties can be used to attract BMP into a bone prosthesis, thereby stimulating osteogenesis.

Further, the VHH according to the invention, such as in the form of the above described medicament, may be used in a method of engineering tissue, comprising administering the VHH to a biomaterial, such as an implanted biological tissue or other biomaterial, in an effective amount to bind a tissue modulating biologically active agent to the VHH. The administration may very suitably be by injection.

Implants

Further provided is an implant comprising a functionalized VHH according to the invention, a fusion protein according to the invention or a protein complex according to the invention. Further provided is a method for the preparation of an implant comprising steps of loading said implant with a functionalized VHH according to the invention, a fusion protein according to the invention or a protein complex according the invention.

Preferably, said implant is loaded with said VHH by chemical coupling of said VHH to a molecule present in said implant or a part or a compound thereof. In a preferred embodiment, said VHH is chemically coupled to the said implant or said part or said compound thereof through N-hydroxysulfosuccinimide (NHS)-chemistry.

In another preferred embodiment, said chemical coupling is carried out by cross linking said functional group present said implant or said part or said compound thereof in a VHH according to the invention.

In another preferred embodiment, said implant or said part or said compound thereof is loaded with a fusion protein or a multimer according to the invention comprising at least one VHH which binds to a molecule present in said implant by contacting said fusion protein or said multimer with said molecule present in said implant resulting in binding between said fusion protein or multimer and said molecule.

In another embodiment, said compound of said implant is a compound for a coating, preferably a calcium phosphate coating. Loading of said implant is suitably carried out by dissolving said VHH according to the invention in a solution for the preparation of said coating. Preferably, said solution comprises calcium phosphate, preferably in a concentration wherein saturation of calcium phosphate occurs. A solid component of said implant, preferably comprising a biomaterial, preferably titanium is incubated with said solution wherein said VHH is dissolved long enough to let calcium phosphate precipitate on said component. Preferably, the bioactivity of said VHH present in said coating is checked, preferably by incubating said coating with the respective ligand which is bound by said VHH (this can be either a growth factor or an antagonist for said growth factor) and measuring the binding of said ligand to said coating.

In another embodiment, said compound of said implant is a compound for a coating, preferably a calcium phosphate coating. Loading of said implant is suitably carried out by dissolving said protein complex according to the invention or the precursors for making said protein complex in a solution for the preparation of said coating. Preferably, said solution comprises calcium phosphate, preferably in a concentration wherein saturation of calcium phosphate occurs. A solid component of said implant, preferably comprising a biomaterial, preferably titanium is incubated with said solution wherein said protein complex according to the invention or the precursors for making said protein complex is dissolved long enough to let calcium phosphate precipitate on said component. Preferably, the release of the growth factor or antagonist is determined, preferably using immunodetection.

In another preferred embodiment, said implant is loaded with the VHH according to the invention, the protein complex or the fusion protein according to the invention by immobilization in membranes of synthetic polymers. Said immobilization can suitably be performed by dissolving said VHH, protein complex or fusion protein in an appropriate volatile solution comprising a synthetic polymer, preferably polyactive. Using solvent casting an ultrathin membrane is prepared as described in U.S. Pat. No. 4,132,824.

In another preferred embodiment, said implant is loaded with the VHH, the protein complex or the fusion protein according to the invention by immobilization in electrospun fibers. Said immobilization can suitably be performed by dissolving said VHH, protein complex or fusion protein in an appropriate volatile solution comprising a synthetic polymer, preferably polyactive. Using an electrospinning device as described in U.S. Pat. No. 6,616,435, fibers are spun with a diameter in the nanometer range.

In another preferred embodiment, said implant is loaded with the VHH, the protein complex or fusion protein according to the invention by capturing said VHH, protein complex or fusion protein in a hydrogel network. In this embodiment, unglycosylated and glycosylated VHH, protein complex or fusion protein as described earlier are dissolved in PBS or an equivalent thereof with a solution of dextran-tyramide conjugate, at a concentration of typically 10% wt with a molecular weight of typically 14 kD and a degree of substitution of 10. The degree of substitution is defined as the number of tyramide residues per 100 anhydroglycose rings of dextran. Subsequently this mixture is incubated with $H_2O_2$ and Horseradish peroxidise, thereby catalyzing the crosslink reaction between the tyramide residues conjugated to dextran.

In another preferred embodiment, said implant is loaded with the VHH, the protein complex or fusion protein according to the invention by crosslinking said VHH, protein complex or fusion protein to the free $NH_2$ groups of a polymer, preferably polyaminoamide, which is comprised in said implant. This can be done by standard chemistry used for coupling of cysteines, lysines or methionines to free $NH_2$ groups. In another preferred embodiment, coupling is effectuated by using a peptide bound to said VHH, protein complex or fusion protein, as described herein.

In another preferred embodiment, said implant is loaded with the VHH, the protein complex or fusion protein according to the invention by coupling a glycosyl group present therein to free $NH_2$ groups of the polyamino amide using carbohydrate chemistry as known in the art.

Preferably, said implant is an injectable fluid that can be administered intravenously or locally at the site where tissue is to be engineered.

According to the invention, said growth factor or said antagonist thereto is derived from any species. Examples of species relevant to the invention include as rabbits, goats, mice, rats, cows, calves, camels, llamas, monkeys, donkeys, guinea pigs, chickens, sheep, dogs, cats, horses, and preferably humans.

Examples

Raising Llama Antibodies to Bone Morphogenic Growth Factors and Wnt Antagonists

Llamas were immunized with bone mophogenic proteins: BMP-6 (R&D systems cat.#507-BP/CF), BMP-7 (R&D system cat.#354-BP/CF), SOST (R&D systems cat.#1406-ST/CF) and DKK1 (R&D systems cat.#5439-DK/CF). The proteins were mixed with the adjuvant Stimune and injected intramuscularly. The immunization scheme consisted of a priming immunization (at day 0) followed by 3 boosts (at days 14, 28 and 35). The immune response was measured in the serum taken up at day 28 and compared to day 0.

The immunizations were approved by the local animal welfare committee.

Construction of Variable Domains of Heavy Chain Llama Antibody Library

When the titer of the heavy chain antibodies increased at day 28, peripheral blood lymphocytes (PBLs) were isolated from 150 ml blood taken up at day 43. Total RNA was isolated from these PBLs using phenol-chloroform-isoamylalcohol method. RNA was converted into cDNA using SuperscriptIII® (Invitrogen). IgG binding domains were amplified with PCR using primers annealing at the signal sequence of the IgGs and the hinge region. The ~700 bp fragments corresponding to the antigen binding domain of the heavy chain antibodies (VHH) was excised from gel, and the SfiI restriction site was introduced at the 5' by a nested PCR-step to facilitate cloning into the display vectors.

The purified 700 bp fragment was digested with BstEII (a restriction site found in the hinge region of heavy chain antibodies) and SfiI, and the resulting 400 bp antigen-binding fragment of the heavy chain antibodies were cloned in a phage-display plasmid.

The plasmids were transferred to *Escherichia coli* strain TG1. A transformation efficiency of $10^8$, which also represents the diversity in the library, was generally obtained.

*E. coli* TG1 was used for the production of phages and for the infection by selected phages. Furthermore, *E. coli* TG1 was used for the production of selected VHH-monoheads and biheads.

Selection of VHH Recognizing Bone Morphogenic Proteins. Bacterium Strain and Cultivation Conditions

*Escherichia coli* strain TG1 was used for the maintenance of the plasmids, infection by the phages and expression of proteins. *E. coli* TG1 was grown in LB or 2×YT medium supplemented with glucose and antibiotics as indicated. VHH-phages were rescued by incubation of the phages with log-phase *E. coli* TG1 at 37° C. for 30 min (static conditions), followed by incubation in the presence of selection (ampicillin) overnight at 37° C. (shaking). Phages were produced from *E. coli* TG1 containing phagemids with VHH genes fused to M13 gene3, by infection of log-phase bacteria with the helper phage VCSM13 (Stratagene, La Jolla, Calif., USA)

for 30 min at 37° C. (static conditions), followed by incubation in the presence of both ampicillin and kanamycin overnight at 37° C. Produced phages were isolated by PEG precipitation of the culture supernatant.
Phage Display Four wells of a MaxiSorb® plate were coated with decreasing concentrations of the different proteins (BMPs, SOST or DKK1). Typical concentrations for the first round selections were 5 µg, 2 µg, 0.2 µg and 0 µg). After washing and blocking the wells with 4% Marvel (dried skimmed milk, Premier International Foods, Coolock, UK) in phosphate buffered saline (PBS), 100 µl of a 2% Marvel solution containing ~$10^{10}$ phages from the dedicated VHH-immune libraries were added to each well and incubated at room temperature for 2 h. The wells were then washed for 15 times with PBS containing 0.05% tween -20 (PBST) (the 5th, 10th and 15th wash steps were done for 10 min) and 3 times with PBS. Bound phages were eluted from the wells with 100 mM triethylamine (TEA) and neutralized with 1M Tris -HCl pH 7.5. DNA information of the selected phages was rescued by infection of E. coli TG1 strain and subsequent selection for ampicillin resistance. The number of eluted phages was determined by plating serial dilutions of the different infections. Phages were produced from the outputs that showed the highest enrichment factors and used for the screening of monoclonal phages, or as input for the second round of selection.

Phagemid containing E. coli TG1 were infected with the helper phage VCSM13 and phage particles were produced overnight in medium containing both ampicillin and kanamycin and no glucose. These phages were precipitated with PEG and used in the 2nd round selection. In the second round of selection, four wells were coated with decreasing concentrations of the different Proteins (BMPs, SOST or DKK1) at concentrations of 2 µg, 0.5 µg, 0.1 µg and 0 µg) in 100 ml PBS, overnight at 4° C. After washing and blocking the wells with 4% Marvel, ~$10^9$ phages from the first round were added to each well in the presence of 2% Marvel and incubated for 2 h at room temperature. The wells were then washed with PBST and PBS as indicated in first round. Bound phages were eluted as indicated for the first round selection.

Several phages from the first and second rounds were tested for binding to the different proteins (BMPs, SOST or DKK1) in a solid phase ELISA using phage particles. Moreover, DNA information of the selected VHHs were subcloned into a plasmid containing C-terminal Myc and His tags. VHH proteins were produced and purified from the periplasm via the C-terminal His-tag. Binding affinity and specificity of the selected VHH was tested in a solid phase ELISA. Furthermore, the ability of the selected VHH to immunoprecipitate cognate antigens was tested using purified proteins.
Phage and VHH Solid Phase ELISA MaxiSorb plate wells were coated overnight at 4° C., with the antigens in PBS. After blocking of the wells with 4% marvel in PBS, they were incubated with VHH or VHH-fused to M13 phages in the presence of 2% Marvel. The wells were washed with PBS-tween, and bound phages were detected by incubation with a mouse Monoclonal antibody against M13 phage coupled to HRP. Bound VHH were detected by incubation with a rabbit anti-VHH polyclonal serum and a goat anti-rabbit coupled to HRP. The amount of HRP was developed by the addition of OPD. The reactions were stopped by the addition of H2SO4 and measured at 490 nm.
Construction of Homo- and Heterobiheads Recognizing One or Two Different Bone Morphogenic Proteins a. PCR was used to amplify the VHH sequences. Different primers sets were designed to amplify the VHH, which will be located at the N terminus and the VHH, which will be located at the C terminus of the bihead. The primers at the 3' of the N-terminal VHH and at the 5' of the C-terminal VHH, may encode a flexible sequence (GS-linker) represented by a repeat of the pentapeptide 'Gly-Gly-Gly-Gly-Ser' (SEQ ID NO:42). These same primers contain a unique restriction site (BamHI). After PCR amplification, the generated fragments were digested with a unique N-terminal restriction site (SfiI) and BamHI for the VHH that will be located at the N terminus, and with BamHI and a unique C-terminal restriction site (BstEII) for VHH that will be located at the C terminus. The fragments are ligated into an expression vector, which was digested with SfiI and BstEII. The VHH-bihead constructed in this way will be produced in E. coli after IPTG induction. The formed bihead will be secreted into the periplasm due to the presence of a PelB-signal sequence.

The VHH-combination described above may consist of the same VHH (homo-biheads) or of distinct VHH (hetero-biheads). When the VHH sequence of interest contain an internal BamHI restriction site, this site should be removed beforehand. Alternatively, primers containing different restriction sites (BspEI) were designed.

b. Similar to the example described under a, a heterobihead consisting of VHH binding to two different bone morphogenic proteins. The position of the VHH at the N or the C termini, and the length of the GS-linker will be optimized for the various purposes.

c. Similar to the example described under a, a heterobihead consisting of a VHH binding a bone morphogenic protein and a VHH binding to the scaffold of the implant material. The position of the VHH at the N or the C termini, and the length of the GS-linker will be optimized for the various purposes.
Biological Assays
KS483

KS483 mouse progenitor cells were cultured in α-MEM (Gilbco) supplemented with 10% fetal bovine serum (FBS; Cambrex), 100 U/ml penicillin (Gilbco) and 100 µg/ml streptomycin (Gilbco) and were incubated at 37° C. in humidified atmosphere and 5% $CO_2$. To perform differentiation assays cells were seeded with a seeding density of 10 000 cells/cm2 (day 0). Upon reaching confluence (4 days elapsed), cells were culture for 3 days stimulated with ascorbic acid (50 µg/ml) and recombinant human BMP-6 (100 ng/ml; R&D Systems) in the presence or absence of VHHs directed against BMPs. Cells were also cultured in the presence of BMP-6 and Wnt antagonists (rh-SOST or rh-DKK1; R&D Systems) in the presence or absence of VHHs selected against SOST or DKK1, respectively. VHHs and respective antigens (BMP-6, BMP-7, rh-SOST, rh-Dkk1) were pre-incubated in phosphate-buffered saline (PBS; Gilbco) for 1 h prior to stimulation. The VHHs concentrations tested range 1 µg/ml to 10 ng/ml. At the end of the culture (day 7), cells were washed with PBS and lysed with CDPStar lysis buffer (Roche). To evaluate alkaline phosphatase activity (ALP), lysate was added to CDPStar reagent (Roche) and luminescence was measured using Vector Microplate Luminometer. Luminescence units obtained were corrected with DNA content. DNA concentration was determined via proliferation assay according to manufacturer's protocol (CyQuant Cell Proliferation Assay Kit; Invitrogen).
KS483 Transient Transfection—Wnt reporter KS483 cells are transiently transfected with a Wnt-responsive promoter reporter (TBE) construct as previously described (Wnt but not BMP signaling is involved in the inhibitory action of sclerostin on BMP-stimulated bone formation (van Bezooijen R L, Svensson J P, Eefting D, Visser A, van der Horst G, Karperien M, Quax P H, Vrieling H, Papapoulos S E, ten Dijke P, Lowik C W. J Bone Miner Res. 2007 January; 22(1):19-28.) Transiently transfected cells are stimulated with recombinant Wnt3a in the presence of the Wnt-antagonists Dkk1 or sclerostin in the presence or absence of a dose range of VHH and 24 hours later luciferase reporter activity is measured.

HEK293 WntDual

HEK293 cells stably transduced with a Wnt-responsive promoter reporter lentiviral construct were stimulated with recombinant Wnt3a in the presence of the Wnt-antagonists Dkk1 or sclerostin in the presence or absence of a dose range of VHH and 24 hours later luciferase reporter activity is measured.

X.1. Improvements of Frame Works of Selected VHHs

We used the data base and the comparison to the germ line sequences to determine potential improvement sites in the frame work sequences and used site directed mutagenesis to improve these frame works.

a. Improvement of the frameworks of VHHs recognizing Sclerostin (Table 1):

In VHH-S-D7 we replaced R in FW4 (110) into Q

In VHH-S-A6-1 (and similar VHHs, see table 1) we introduced mutation V47E;

In VHH-S-H12 we introduced mutation V47E

In VHH-S-E11 (and similar VHHs) we introduced the mutations M84N N85S, Q87K and G89E either as individual mutations or combinations thereof;

In VHH-S-B1 (and similar sequences) we replace the typical VH sequences KGPEW (SEQ ID NO:43) into the typical VHH sequences KEREL (SEQ ID NO:44) and KQREL (SEQ ID NO:45). In VHH-S-G5 we introduced mutation SL 19/20 into RL.

b. Improvement of the frameworks of VHHs recognizing BMP6, 7 (Table 2):

In VHH-6-A1 we introduced the mutations T19R and L50A and [C63S and A64V] either as individual mutations or combinations thereof; In VHH-7-G7 we introduced the mutations V49A and S51R either individual or in combination with each other;

In VHH-7-H9 we introduced the mutation R50A

In VHH-6-C2 we introduced the deletion of the insert EN (761,b);

In VHH-7-A11 we introduced the mutation S11L and replaced KVH [74-76] into NAK c. Improvement of the frameworks of VHHs recognizing DKK1 (Table 3)

In VHH-D-B7 we introduced the mutations Q43K and S68F either individual or in combination with each other;

In VHH-D-C9 we introduced the deletion of the insert EW [47a,b];

In VHH-D-D4 we introduced the mutation R59Y;

In VHH-D-G5 we replaced the sequence VH [50,51] into VAAIS and introduced the mutation P33A;

In VHH-D-C1 (and similar sequences) we introduced the mutation V66G.

X.2 Improvements of the CDRs of the Selected VHHs.

Comparison of the germ line V(D)J genes combinations and the matured VHHs show at nucleotide and amino acids level exactly the maturation of the CDRs. This in combination with our large data base and information at atomic level of the interaction between antigens and their cognate VHHs (Lutje Hulsik, Ph. D. Thesis 2009) provided substantial information which amino acids of CDRs may play important roles in the interactions between the selected VHHs and sclerostin, BMP6, BMP7 or DKK1, respectively. Using this information we carried out an alanine scan of the CDRs. Subsequently we used a semi rational approach (Rajpal et al, Protein Sci. 7, 9-1868-1874, 1998) to design changes of the amino acid sequences of CDRs. In an attempt to improve the binding affinity and specificity of the selected VHHs towards cognate antigens, we will carry an Ala-scan of the CDRs. Based on the information gained from the reconstitution of the maturation process from the germ line V(D)J genes, and based on the knowledge gained from the interaction between VHHs and their antigens already available in the large data base, we will design changes of the amino acid sequences of the CDRs to improve the binding properties of the VHHs to their cognate antigens.

Coupling of a VHH to a Ligand

The VHHs selected against the different targets show binding specificities to the cognate antigens, in addition to the modulation of their biological functions. To concentrate the effects of the VHHs to spatially restricted regions, VHHs should be coupled to a ligand to target and reside to a specific spot. VHHs may be coupled to a ligand by extension of the gene encoding the VHH with an additional stretch of nucleotides encoding a peptide/protein with the property to bind to a certain surface. A well known example is the His6 tag that ensures coupling of VHHs to metal surfaces, in particular a Nickel surface. Another way of coupling a VHH to a ligand is by the extension of the C terminus of VHHs with a short peptide containing additional Cys residues. These Cys residues can be coupled covalently to any other compound carrying a free SH group. A third way to couple a VHH to a ligand is by extending the C terminus with unnatural amino acids (Zhang et al. Biochemistry 42. 22. 6735-6746 (2003)). Such unnatural amino acids carry a reactive group, such as alkyn or azide groups, which react with high efficiency and specificity to form covalent linkage with compounds containing azide or alkyn groups, respectively. A fourth way to couple a VHH to a ligand is by inclusion of an N-linked glycosylation site.

VHHs that recognize any of the above mentioned surfaces according to methods described earlier by us can be selected from non-immunized llama libraries. Genetic coupling of a VHH recognizing such a surface and a VHH involved in biological processes relevant for tissue engineering provide hetero-biheads that are very suitable to influence locally concentrations of proteins or other biological material involved in tissue engineering. Coupling of peptides derived from the CDRs of VHHs involved in binding to the above mentioned surfaces may be sufficient to target and localize the VHHs to the desired spots.

As an example, VHHs specific to BMP-6 and BMP-7 can be immobilized to the SPR sensorchip CM5 through NHS chemistry. The immobilized VHHs could still bind the specific target molecules with high affinity and specificity.

VHH Immobilized in Calcium Phosphate Coatings

VHH can be dissolved in a saturated calcium phosphate solution. Titanium implants of 1 $cm^2$ can be incubated with the saturated solution under conditions that allow calcium phosphate precipitation on the titanium surface. The presence of the VHH in the coatings can be determined. In addition, the bioactivity of the VHH can be determined by incubating the coating with the respective VHH ligand and measuring the binding of the ligand to the coating.

In another example, VHH in combination with the respective ligand can be dissolved in a saturated calcium phosphate solution and the protein complex can be co-precipitated in the phosphate coating on a titanium surface. The release profile of the ligand over time can be determined using ELISA.

VHH Immobilized in Membranes of Synthetic Polymers

VHH and polyactive can be dissolved in an appropriate volatile solution. Using solvent casting an ultrathin membrane can be prepared. The incorporation of the VHH in the membrane can be determined using atomic force microscopy. In addition, bioactivity of the VHH can be determined by incubation of the membrane with the appropriate ligand and binding characteristics can be determined. Likewise, VHH in complex with the appropriate ligand and polyactive can be dissolved in an appropriate volatile solution. Using solvent casting an ultrathin membrane can be prepared. The incorporation of the VHH complexed with its ligand can be determined using atomic force microscopy. The release profiles of the ligand from the membrane can be determined over time using ELISA. The biological activity of the functionalized membrane can be determined by incubating with human mesenchymal stem cells.

VHH Immobilized in Electrospun Fibers

VHH and polyactive can be dissolved in an appropriate volatile solution. Using an electrospinning device with a field strength of 15 kV and a distance of 10 cm, fibers with a diameter in the nanometer range or spun. The thickness of the fibers can be determined using Scanning Electron Microscopy. Bioactivity of the VHH can be determined by incubation of the fibers with the appropriate ligand and binding characteristics can be determined. Similarly, electrospun fibers can be produced using a solution of polyactive and VHH complexed with the appropriate ligand. Fiber characteristics can be determined using Scanning Electron Microscopy. The release profile of the ligand can be determined using ELISA. Bioactivity of the fibers can be examined using cell culture experiments with human mesenchymal stem cells.

VHH Captured in a Hydrogel Network

Unglycosylated and glycosylated VHH can be dissolved in PBS and mixed with a 10 wt % solution of a dextran-tyramide conjugate with a molecular weight of 14 kD and a degree of substitution of 10. The latter is defined as the number of tyramide residues per 100 anhydroglycose rings of dextran. The mixture can be incubated with $H_2O_2$ and Horseradish peroxidase, which catalyze a crosslinking reaction between the tyramide residues conjugated to dextran. The release of the VHH over time out of the gel can be measured using ELISA. Similarly, both types of VHH can be captured in the hydrogel complexed with the respective ligand. The release characteristics of the ligand and the VHH can be determined using ELISA. The biological performance can be measured in gels in which also cells can be captured during the cross linking reaction. The effect on tissue formation in culture can be determined.

VHH Captured by Covalent Attachment to a Poly(Amino Amide)

A sheet of poly(amino amide) can be prepared and the number of free $NH_2$ groups available for cross linking reactions can be determined. VHH can be coupled to this sheet by standard chemistry used for coupling of cysteines, lysines or methiones to free $NH_2$ groups in the polymeric sheet. The ligand binding characteristics of the VHH immobilized to the sheet can be determined. In addition, the sheet coated with VHH is incubated with mesenchymal stem cells and differentiation characteristics of the polymer can be assessed.

In addition, VHH can be coupled to the polymer sheet using a peptide as a linker. This peptide may contain a lysine, a cysteine or a methione or an unnatural amino acid which is used for coupling to the polymer. The binding characteristics and biological activity of the prepared polymer sheets can be assessed as described.

Finally, a glycosylated VHH can be coupled to the free $NH_2$ groups of the poly(amino amide) sheet using carbohydrate chemistry.

VHHs According to the Invention which Bind to an Implant

VHHs according to the invention which bind to an implant were made. These VHHs are directed against the different biomaterials utilized in tissue engineering and were in this experiment selected from the group consisting of hydroxyapatite (HA), Titanium (Ti) and Titanium coated with calcium-phosphate (Ti-CA). The VHHs were selected by phage display using a non-immune VHH-phage library. Two rounds of panning selection were needed to yield a good enrichment of binding phages. After screening, few VHHs were found to bind the biomaterials with reasonable affinity.

Optimalisation of the Material-Binding Sequences of VHHs According to the Invention which Bind to Biomaterials Inspection of the sequences of the VHHs binding to Ti and HA revealed that some of these sequences are not optimal in respect to physical and/or proteolytic stability and for production in microorganisms. We have found that VHHs having a FW4 that contains at position 107 a K and position 110 a L are less stable and produced at a much lower level compared to the ones where Q's are present at both positions. Consequently we have changed the sequence of MG6 by the mutations K107Q and L107Q. In VHH MG6, we have replaced the C50 and C97 residues by either A or S on these positions to improve stability. Moreover we noticed that during the maturation process the sequence very characteristic for Llama heavy chain antibodies, KEREF (43-47) (SEQ ID NO:46), present in a sub set of the V-genes encoding VHHs was mutated into KVREL (sequence MA7) (SEQ ID NO:47) which reduced the production rate and increases the tendency of this VHH to aggregate and the sequence KQREL (43-47) (SEQ ID NO:45) was mutated into QQREL (MG12) (SEQ ID NO:48) which is also less optimal. Consequently we replaced these sequences with the original germ line sequences. Finally also the amino acid residues I and T on position 109 of MA7 and MG7 respectively were mutated back to T. The optimized VHH sequences for binding to different biomaterials are listed in Tables 4-6.

TABLE 4

VHH binding hydroxyaptite biomaterials

| HA-VHHs | Sequence |
|---|---|
| VHH-MG6 | QVQLQESGGGLVQPGGSLRLSCSASGFSLDIYAIGWFRQAPG KEREGVSCINSSGSSTYYADSVKGRFTISRDNAKNTIYLQMN SLKPEDTAVYYCATGGCSPFGGVAGVKDYWGQGTQVTVSS (SEQ ID NO: 49) |
| VHH-MG7 | QVKLEESGGGLVQAGGSLRLSCAASGRTFSTYSMGWFRRAPG KEREFVAAISWSGGTTRYTNSVKGRFTISKDNFGNTVYLQMN NLKPEDTAVYYCATRYSYSTTPEEYDLWGQGNQVTVSS (SEQ ID NO: 50) |

TABLE 5

VHH binding Titanium biomaterials

| Ti-VHHs | Sequences |
|---|---|
| VHH-MA7 | QVQLQESGGGLVQAGGSLRLSCVASGGTFSGYAMAWFRQR PGKVREFVATISRSAASTDYADSVKGRFTISRDNAKNTVY LQMNSLKPEDTAVYYCAAKLGVTSFYRSTYSYWGQGIQVTVSS (SEQ ID NO: 51) |

TABLE 6

VHH binding Titanium-$Ca^{2+}$-phosphate or Titanium-$Ca^{2+}$-phosphate coated biomaterials

| Ti-CA-VHHs | Sequences |
|---|---|
| VHH-MG12 | QVQLQESGGGLVQPGGSLRLSCVASGNIFSISAMGWYRQA PGQQRELVASMTNEGNTNYADSVKGRFTISRDNAKNTVYL QMDSLKPEDTAVYYCNAYYYYNEYDPDSDAMDYWGKGTLV TVSS (SEQ ID NO: 52) |

TABLE 7

Examples of fusion proteins "F" according to the invention binding to growth factors or growth factor antagonists (abbreviated "GR") and biomaterials (abbreviated "MA")

| BMP6-MA | Sequences |
|---|---|
| 6F2-MG7 | EVQLVESGGGFVQAGGSLRLSCAASGSIFSINAMGWYRQAPGKQRELVAA ITSGGSTNYADSVKGRFTISRDNAKNTLYLQMNSLKPEDTAVYYCSAVTIL LTSGGWGSGNDYWGQGTQVTVSSGGGGSEVQLVESGGGLVQAGGSLRLS CAASGRTFSTYSMGWFRRAPGKEREFVAAISWSGGTTRYTNSVKGRFTIS KDNFGNTVYLQMNNLKPEDTAVYYCATRYSYSTTPEEYDLWGQGNQVTV SS (SEQ ID NO: 53) |
| BMP7-MA | Sequences |
| 7G7-MG12 | EVQLVESGGGLVQAGGSLRLSCAASGFTFDDYIIGWFRQAPGKEREGISCI SSSDGSTYYADSVTGRFTISSDNAKNTVYLQMNSLKPEDTAVYYCAAHAK WPYGTYSFRRCRRASFDSWGQGTQVTVSSGGGGSEVQLVESGGGLVQPG GSLRLSCVASGNIFSISAMGWYRQAPGQQRELVASMTNEGNTNYADSVKG RFTISRDNAKNTVYLQMDSLKPEDTAVYYCNAYYYYNEYDPDSDAMDYW GKGTLVTVSS (SEQ ID NO: 54) |
| DKK-MA | Sequences |
| DD4-MG7 | EVQLVESGGGLVQAGDSLRLSCAASGRSISLYAMAWFRQAAGKEREFVAA INWSGGSTRYADSVKGRFSISRDTAKNTVYLTMNSLKPEDTAVYYCATDS STTVVFYSSSNSLRYWGQGTQVTVSSGGGGSEVQLVESGGGLVQAGGSLR LSCAASGRTFSTYSMGWFRRAPGKEREFVAAISWSGGTTRYTNSVKGRFT ISKDNFGNTVYLQMNNLKPEDTAVYYCATRYSYSTTPEEYDLWGQGNQV TVSS (SEQ ID NO: 55) |
| Sost-MA | Sequences |
| SA6-MG6 | EVQLVESGGGLVQAGGSLRLSCAASGRTFSRDVMGWFRQAPGKVREVVG SITWSGGSTYYADSVKGRFTISRDNAKNTMYLQMNSLKPEDTGVYYCAVA ELGSTYNDWGQGTQVTVSSGGGGSEVQLVESGGGLVQPGGSLRLSCSAS GFSLDIYAIGWFRQAPGKEREGVSCINSSGSSTYYADSVKGRFTISRDNAK NTIYLQMNSLKPEDTAVYYCATGGCSPFGGVAGVKDYWGQGTQVTVSS (SEQ ID NO: 56) | according to the invention was effectively competed by the monospecific VHH according to the invention which binds to a biomaterial. About 50% competition was found. No difference in competition was noticed between 1 μg and 5 μg of the VHH according to the invention which bind to biomaterials. This result confirms the binding of the fusion proteins according to the invention to biomaterials according to the invention through the VHHs binding to biomaterials. Sequences of preferred embodiments of the fusion proteins according to the invention are listed in Table 7. These contain the unit GGGGS (SEQ ID NO:42) as a linker. It is to be noted that this unit may be repeated. In effect, the linking unit will then be $(GGGGS)_n$ in which n is an integer, preferably from 0 to 10.

VHH Fusion Proteins According to the Invention

The VHHs according to the invention binding to the growth factors and/or the growth factors inhibitors were fused to VHHs according to the invention binding to biomaterials. The resulting fusion proteins according to the invention were tested for the simultaneous binding of the materials and the respective antigen. Similar amount of growth factor was bound to the fusion protein according to the invention when compared to the monovalent VHH according to the invention which binds to the growth factors and/or the growth factors inhibitor (FIG. 7A), indicating that the fusion between a VHH according to the invention which binds to a growth factors and/or a growth factors inhibitor and a VHH according to the invention which binds to a biomaterial is not detrimental to its capacity to bind to a growth factor and/or growth factors inhibitor.

Figure 7:
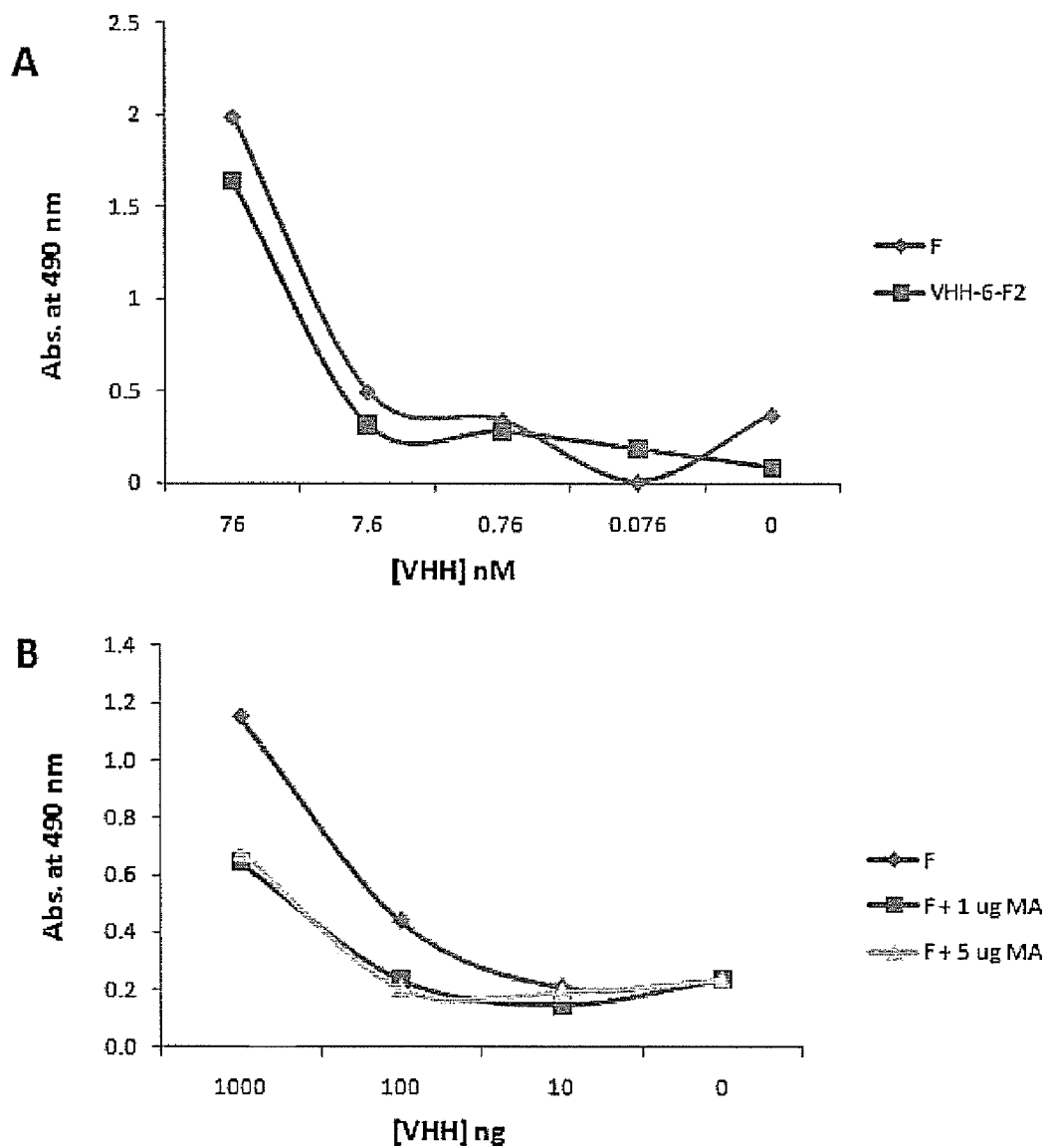
FIG. 7 shows the binding properties of the fusion proteins according to the invention which bind to a growth factor or growth factor inhibitor and to a biomaterial. Fusion proteins according to the invention are composed of the VHH according to the invention binding to a growth factor (indicated in the figure as "VHH-6-F2") and a VHH binding to a biomaterial (indicated in the figure as "MA"). This figure displays the binding results of fusion proteins and VHHs which bind to hydroxyapatite as biomaterial and BMP6 as growth factor, but similar results were obtained when fusion proteins and VHHs against Titanium and Titanium coated with calcium-phosphate were used as biomaterials. The fusion proteins (indicated in the figure as "F") were constructed by genetic fusion of a VHH binding to BMP6 and a VHH binding to hydroxyapatite. To achieve binding to the growth factor BMP6 (FIG. 7A), 100 ng of BMP6 was coated into wells of a MaxiSorb® plate. Serial dilutions of the VHH which binds to BMP6 (VHH-6-F2) and fusion proteins according to the invention (F) were added to the wells. Bound VHHs (VHH-6-F2) and fusion proteins (F) were detected with labelled polyclonal antibodies. Detection of the labelled antibodies at 490 nm revealed that both VHH-6-F2 and the F fusion protein are bound in equal amounts, indicating that fusion between monospecific VHHs according to the invention does not affect the binding properties of the VHH which binds to a growth factor.

The fusion proteins according to the invention were also found to bind to biomaterials in a dose-response manner (FIG. 7B). Furthermore, the binding of the fusion proteins Functionalized VHHs According to the Invention Using AP1 or AP2

VHHs directed against BMP7 (G7) or BMP6 (H6) were fused to AP1 and AP2 (bold), respectively. Sequences thereof are displayed in Table 8. AP1 and AP2 are peptides which bind with high specificity to hydroxyapatite. A consensus sequence for metalloproteases (underlined in Table 8) was introduced into the sequence, to liberate the VHH from HA materials if desired. The VHH construct contained further a FLAG tag (italic) for detection and His6 tag for purification purposes. AP1 sequence was grafted into the CDR3 of a VHH scaffold (AP1-graft) by replacing all CDR3 amino acids with the AP1 peptide. The sequences of the functionalized VHHs using AP1 or AP2 are listed in Table 8.

Figure 8:
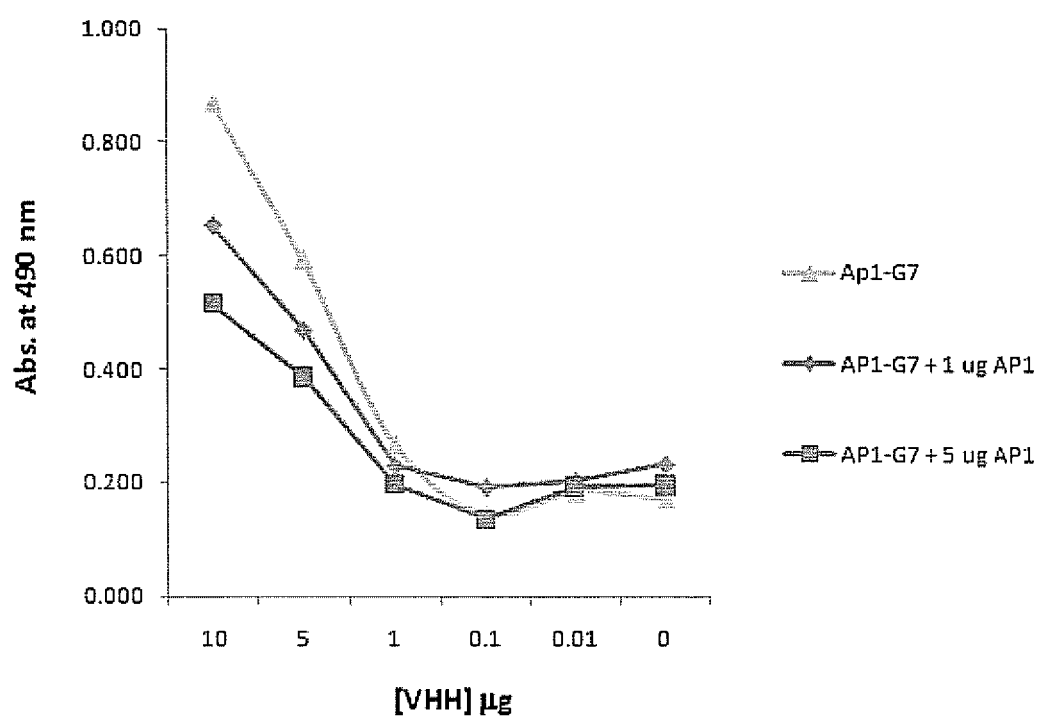
FIG. 8 shows the effectiveness of binding between a functionalized VHH according to the invention (functionalized with a c-terminal peptide) and hydroxyapatite as described in the examples. For this experiment, a VHH was fused to AP1 peptide (with amino acid sequence VTKHLNQISQSY (SEQ ID NO:1)). Serial dilutions of the AP1-G7 VHH were added to three hydroxyapatite plates of a homogeneous size range (1 mm$^2$), which were treated with a 2% BSA blocking solution. AP1-G7 was added to hydroxyapatite plates in the absence or presence of 1 µg or 5 µg of the synthesized AP1. After washing, bound VHHs were detected with an anti-FLAG monoclonal antibody. A clear reduction of binding was observed with 1 µg of AP1, and considerably more reduction of binding was found with 5 µg of AP1.
Figure 9:
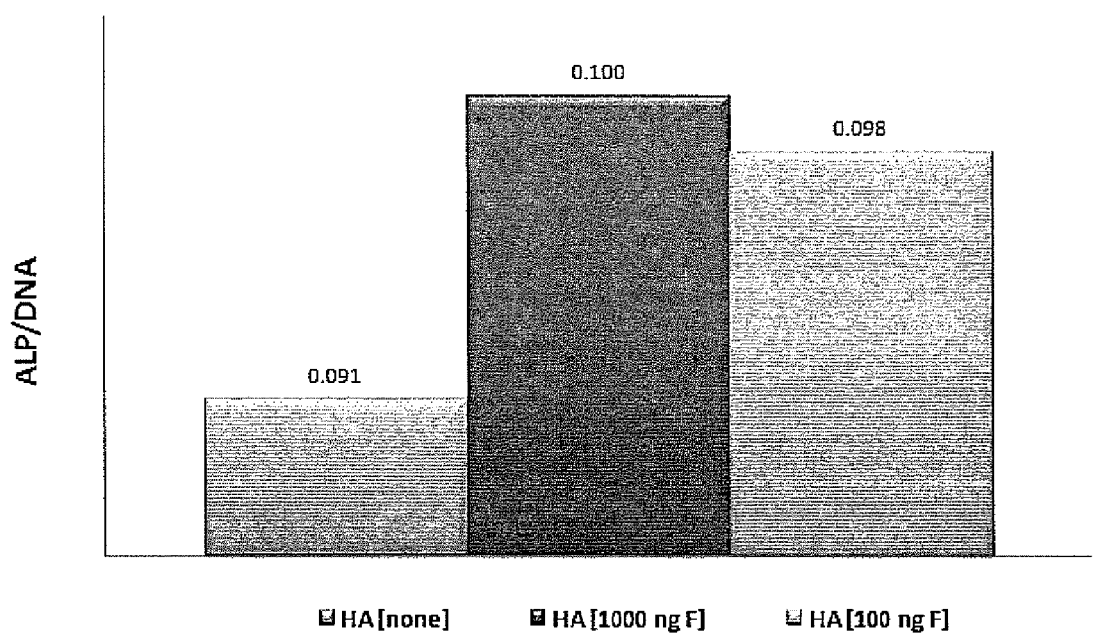
FIG. 9 shows the effect of a fusion protein according to the invention on ALP expression by KS483 cells cultivated on hydroxyapatite plates. KS483 cells are osteoblasts which express ALP during differentiation. Differentiation is a measure for tissue recovery after implantation. Therefore, high ALP expression is an indication of effectiveness of a treatment which is directed to recovery of a tissue after implantation. This figure shows that in the presence of the fusion protein F (which binds to hydroxyapatite and to BMP6) a higher ALP activity of KS483 cells is achieved than in the absence of the fusion protein F.
Figure 10:
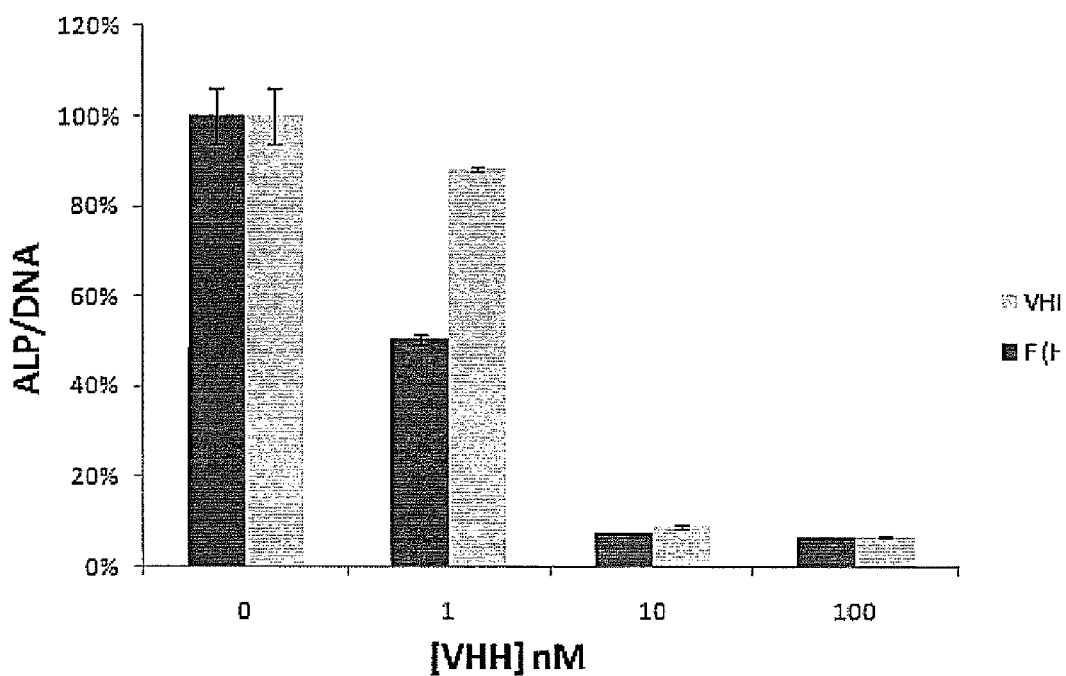
FIG. 10 shows a comparison of BMP6 antagonistic activities of a VHH according to the invention (VHH-6-H1, the second bars at 0, 1, 10 and 100 nM) binding to BMP6 and a fusion protein according to the invention (F/H1-H1) which is a fusion protein between two VHHs which bind to BMP6. This figure shows that the fusion protein is more effective in inhibiting alkaline phosphatase (ALP) activity than the VHH according to the invention with a single binding site for a BMP6 at a concentration of 1 nM. Inhibition was more evident at low concentrations.
Figure 11:
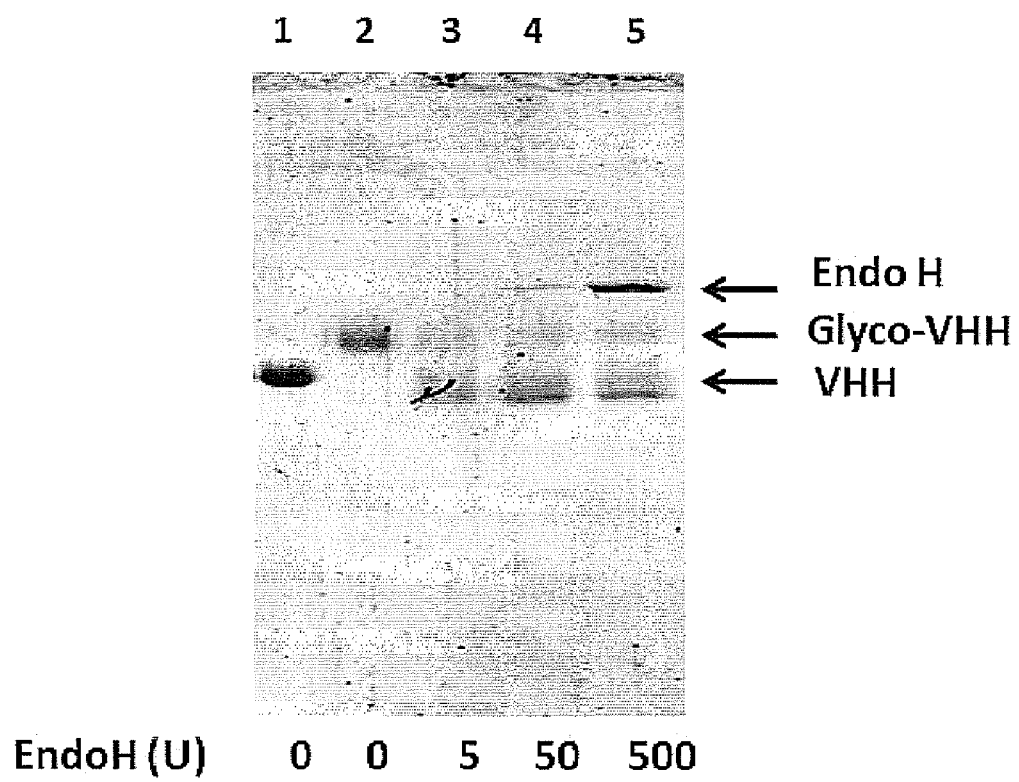
FIG. 11 shows the incorporation of a glycosylation site in a VHH according to the invention. A N-glycosylation site was introduced in loop 5 of VHH-7-G7 using site directed mutagenesis. When the mutated sequence was produced in yeast and analysed on 15% SDS-polyacrylamide gel (lane 2), its apparent molecular weight was higher than the same sequence expressed in *E. coli* (lane 1). To confirm the presence of N-linked glycosylation, yeast produced VHH was incubated with increasing concentrations of EndoH enzyme, which degrades N-linked sugars with high specificity. The apparent molecular weight of the VHHs shifted back to the position of the VHH expressed in *E. coli*, indicating that the glycosyl group was removed by EndoH.

VHHs According to the Invention Functionalized Using Peptides Binding to Hydroxyapatite (HA):

Peptides (12-mers) that showed affinity to HA were selected by phage display. The sequences of 2 of the selected peptides were fused to a VHH directed against a growth factor (Table 8). The resulting AP-VHHs were produced, purified and incubated with HA plates (FIG. 8). AP1 directed the binding of G7 to HA, since increasing concentrations of the free peptide AP1 (1 lag and 5 μg) competed for binding of the AP1-G7 in a dose response manner.

The VHH scaffold was chosen for its stability and high secretion capacity. The AP1 sequence was grafted into CDR3 by replacing the original CDR3 sequence. The resulting sequence is depicted in Table 8.

Biological Effects of Fusion Proteins According to the Invention which Bind to BMP6 and to HA on the ALP Activity in KS483 Cells KS483 cells were cultivated for 3 days in DMEM, 10% FCS on hydroxyapatite plates that were uncoated, coated with 1000 ng of F fusion protein or 100 ng of F fusion protein. Hydroxyapatite plates were coated with the VHHs as indicated, blocked with DMEM, 10% FCS, then incubated with 100 ng/ml BMP6 for 1 h at room temperature.

The hydroxyapatite plates were washed. Cells were seeded on hydroxyapatite plates in DMEM, 10% FCS and 200 μM ascorbic acid.

This resulted in differentiation of KS483 cells after washing out the BMP6 prior to cultivation of the cells.

After 3 day, cells were lyzed and ALP activity was measured using pNPP (Sigma Aldrich). ALP activity was corrected to the amount of DNA (ALP/DNA; indicated on top of the bars).

The amount of ALP corrected with DNA concentration was slightly higher in HA coated with F, compared to non-coated HA (FIG. 9). The effect on the cells was proportional to the amount of coated F biheads. Higher differentiations are expected when using VHH directed against and neutralizing antagonists of differentiation.

TABLE 8

Hydroxyapatite-specific peptides-functionalized VHHs

| BMP-AP | Sequences |
|---|---|
| AP1-G7 | EVQLVESGGGLVQAGGSLRLSCAASGFTEDDYIIGWERQAPGKEREGISCISSSDG<br>TYYADSVTGRFTISSDNAKNTVYLQMNSLKPEDTAVYYCAAHAKWPYGTYSFRR<br>RRASEDSWGQGTQVTVSSAAAGPQGIWGQAAA***VTKHLNQISQSY***VDA*DYKDDDD*<br>KSAAHHHHHHSAA (SEQ ID NO: 57) |
| AP2-H6 | EVQLVESGGGLVQAGGSLRLSCAASGRTESSYAMGWERQAPGKERDEVAAISWS<br>GSTYYTGSVKGRFNISRDNAKNTVYLQMNSLKPEDTAVYYCAGGPRSAYYDDYG<br>DYWGQGTQVTVSSAAAGPQGIWGQAA***APWHLSSQYSRT***VDA*DYKDDDDK*SAAH<br>HHHHHSAA (SEQ ID NO: 58) |
| AP1-graft | QVQLQESGGGLVQAGGSLRLSCTASGRISSSYDMGWERQAPGKEREEVAAISWSG<br>GTTDYADSVKGRFAISKDNAKNAVYLQMNSLKPEDTAVYYCAA***VTKHLNQISQS***<br>YWGQGTQVTVSS (SEQ ID NO: 59) |

Neutralizing BMP Effects of VHHs and Fusion Proteins According to the Invention on ALP Activity in C2C12 Cells To establish whether fusion proteins according to the invention having two binding sites (bihead) for a growth factor are more effective in inhibiting ALP activity than a VHH according to the invention which has a single binding site (monohead) for a growth factor, C2C12 cells were cultivated in DMEM, 10% FCS in the presence of 100 ng/ml of BMP6 and 200 μM of ascorbic acid. Monohead VHH-6-H1, bihead (F/H1-H1) or no VHH at all (set at 100%) were included at the indicated concentrations as shown in FIG. 10. After 3 days of growth, ALP and DNA contents were measured. ALP activity as shown herein was corrected to DNA content.

FIG. 10 clearly shows that the fusion proteins according to the invention are more potent in inhibiting BMP6 activity than VHHs according to the invention which bind to BMP6. This effect was more evident at low concentration of these VHHs.

VHH Provided with a Glycosyl Group According to the Invention

To facilitate integration of VHHs into materials made of polysaccharides such as dextran, a glycosylation site was introduced into a VHH directed against BMP7 (Table 10) using site directed mutagenesis (quick change mutagenesis, Stratagene). Mutated VHH was expressed in yeast S. cervesia and was found to migrate at higher apparent molecular weight (FIG. 11, lane 2). The presence of the glycosyl group was confirmed by digestion with the enzyme EndoH (New England Biolabs). By using increasing amounts of EndoH, more VHH was running at the position of the same VHH expressed in *E. coli*, which is unable to add glycosyl groups to proteins (FIG. 11, lanes 3-5).

Glycosylated VHH was tested for binding to cognate antigen and was found still to bind to BMP7, although with a reduced affinity, compared to the non-glycosylated VHH expressed in *E. coli*.

TABLE 9

| glycosylation | Sequences |
|---|---|
| VHH-7-G7 | EVQLVESGGGLVQAGGSLRLSCAASGFTFDDYIIGWFRQAPGKEREG<br>ISCISSSDGSTYYADSVTGRFTISSDNAKNTVYLQMNSLKPEDTAVYY<br>CAAHAKWPYGTYSFRRCRRASFDSWGQGTQVTVSS (SEQ ID NO: 60) |
| Glyco-VHH | EVQLVESGGGLVQAGGSLRLSCAASGFTFDDYIIGWFRQAPGKEREG<br>ISCISSSDGSTYYADSVTGRFTISSDNANNTVYLQMNSLKPEDTAVYY<br>CAAHAKWPYGTYSFRRCRRASFDSWGQGTQVTVSS (SEQ ID NO: 61) |

Figure 12:
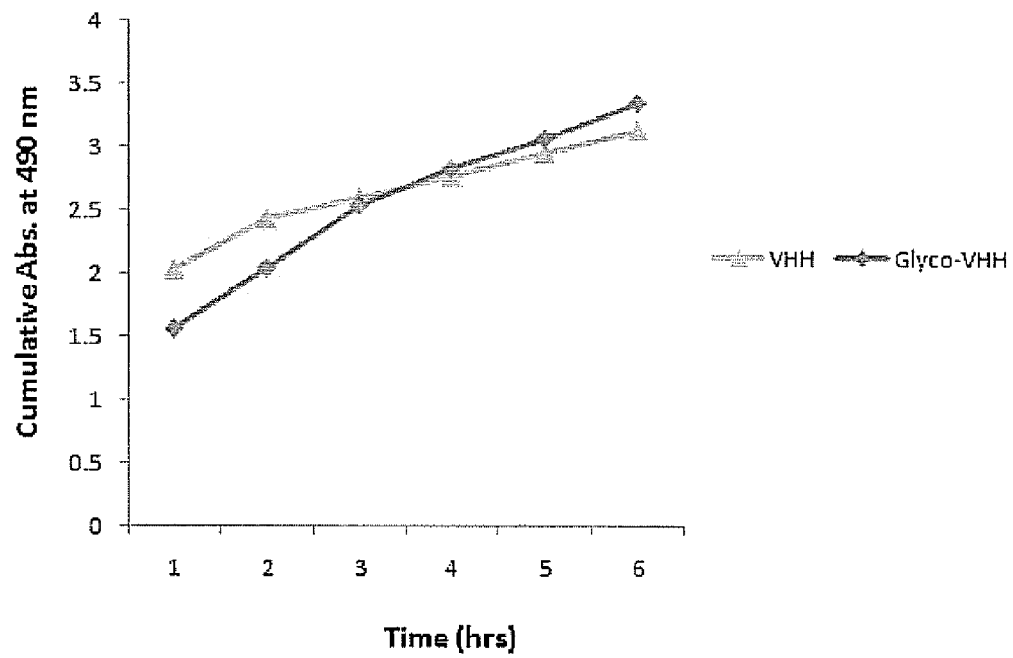
FIG. 12 shows VHH release from a dextran gel. ELISA signals obtained with undiluted PBS wash samples at the indicated time points were measured and added to the next time point. The resulting cumulative absorbance at 490 nm was represented in the graph.

Integration of the glycosylated VHH into a dextran-tyramine gel was assayed by gelating the dextran-tyramine polymers using peroxidase and $H_2O_2$ in the presence of glycosylated and non-glycosyalated VHH as described (R. Jin et al., Tissue Engineering Part A 2010). The gels were washed with PBS each hour and presence of VHHs in the PBS wash was detected in ELISA using a polyclonal antibody against VHH (FIG. 12).

Figure 6:
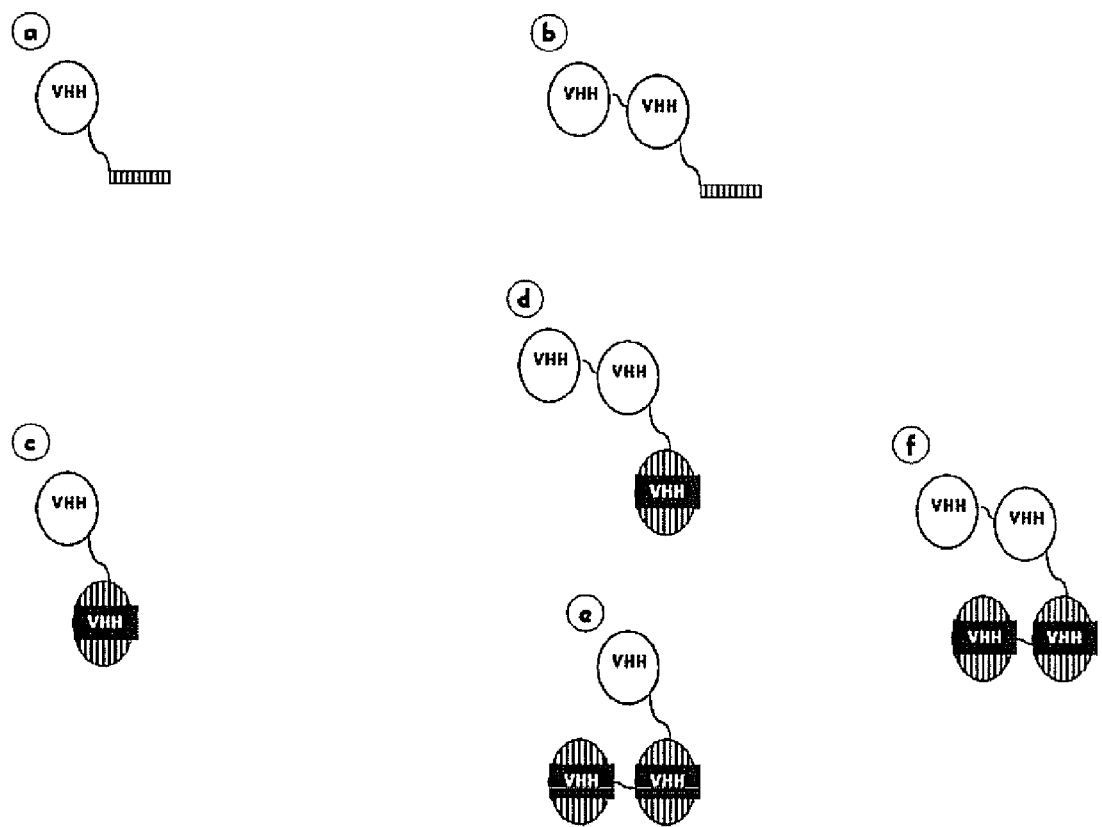
FIG. 6 shows an overview of the different VHH combinations to modify implants. VHHs according to the invention can be functionalized to bind to the scaffolds of the biomaterials. Functionalization is achieved by adding a linker to the VHH (a). The linker may contain Cys or Met residue, which will bind to the biomaterial directly via S—S bridges or amine groups. The linker may also contain unnatural amino acids (=modified Tyr and Lys residues, such as Tyr-azide and Tyr-alkyn), which show specific chemical coupling between the azide and alkyn groups. Alternatively, these residues will bind a peptide through S—S bridges, amine groups or the unnatural amino acids. The later peptide should have affinity to the scaffold of the biomaterials. Such peptide will be selected against the biomaterials using phage-peptide libraries. VHHs may also be chemically linked to biomaterials in a non-directed manner by using NHS(N-hydrosuccinimde chemistry). In this way all amine groups in the VHH may be involved in the binding (also residues that are important for binding to antigen). To increase the avidity to the growth factors, bivalents of the same VHH may be constructed (b). Different VHHs may be linked together to broaden the range of biomolecules (growth factors) that can be bind to the biomaterials. VHHs may also be selected against the biomaterials in the same way as was done for growth factors. For this purpose a non-immunized VHH library is preferred. The VHH binding to implant and the VHH binding to biomelcules are joined together in a biparatopic bihead (c). To increase the avidity and/or broaden the range of biomolecules that bind to the biomaterials a second VHH directed against biomolecules is inserted (d). To increase the residence time of the VHHs in the implant, an additional copy of the VHH directed against the biomaterials is added (e). Additional copies of both VHH directed against biomolecules and VHH directed against biomaterials may be included to increase residence time and increase avidity to and/or broaden the range of the biomolecules displayed on the implant (f). By selecting VHHs with different affinities to the biomaterials and by constructing biheads or monoheads of these VHH we will be able to manipulate the residence time of the VHHs, and thus biomolecules, on the implant according to the desired or the necessary time.

In the first 3 hours of the PBS washings of the dextran gel, more non-glycosylated VHH were released compared to the glycosylated VHH suggesting better entrapment of the glycosylated VHH in the hydrogel network. Furthermore, more glycosylated VHH was found in the PBS wash after the 3, indicating that more glycosylated VHHs were retained into the dextran gel compared to non-glycosylated VHH, confirming entrapment of the glucosylated-VHH in the gel (FIG. 6).

The invention claimed is:

1. A method to prepare a loaded implant comprising the step of loading said implant with a single heavy-chain variable domain antibody (VHH) wherein said VHH binds to bone morphogenic protein and which VHH comprises an amino acid sequence which binds to said implant which amino acid sequence is VTKHLNQISQSY (AP1) (SEQ ID NO:1) or APWHLSSQYSRT (AP2) (SEQ ID NO:2); and wherein said VHH comprises an amino acid sequence selected from the group consisting of SEQ ID NO:17 through SEQ ID NO:24 and SEQ ID NO: 31.

2. The method of claim 1, wherein said loading is performed using microcontact printing.

3. The method of claim 1 wherein the amino acid sequence which binds to said implant is to said VHH via a cysteine or methionine residue present in the last 10 amino acids of the C terminal end of said VHH, with the exception of the last amino acid.

4. The method of claim 1 wherein the implant comprises hydroxyapatite.

* * * * *